(12) United States Patent
Jove et al.

(10) Patent No.: US 9,345,682 B2
(45) Date of Patent: May 24, 2016

(54) INHIBITION OF STAT3 SIGNAL TRANSDUCTION FOR HUMAN CANCER THERAPY

(75) Inventors: Richard Jove, Tampa, FL (US); William Dalton, Tampa, FL (US); Said Sebti, Tampa, FL (US); Hua Yu, Tampa, FL (US); Richard Heller, Temple Terrace, FL (US); Mark Jaroszeski, Tampa, FL (US); Richard A. Gilbert, Tampa, FL (US); Andrew D. Hamilton, Guilford, CT (US)

(73) Assignees: University of South Florida, Tampa, FL (US); Yale University, New Haven, CT (US)

( * ) Notice: Subject to any disclaimer, the term of this patent is extended or adjusted under 35 U.S.C. 154(b) by 1119 days.

(21) Appl. No.: 11/512,049

(22) Filed: Aug. 28, 2006

(65) Prior Publication Data

US 2007/0060521 A1 Mar. 15, 2007

Related U.S. Application Data

(63) Continuation of application No. 09/492,764, filed on Jan. 27, 2000, now abandoned.

(60) Provisional application No. 60/117,600, filed on Jan. 27, 1999.

(51) Int. Cl.

| | |
|---|---|
| C07K 5/083 | (2006.01) |
| C07K 5/087 | (2006.01) |
| C07K 5/103 | (2006.01) |
| C07K 5/107 | (2006.01) |
| C07K 7/06 | (2006.01) |
| C07K 9/00 | (2006.01) |
| A61K 31/277 | (2006.01) |
| A61K 31/00 | (2006.01) |
| A61K 31/4155 | (2006.01) |
| A61K 31/428 | (2006.01) |
| A61K 31/4406 | (2006.01) |
| A61K 31/498 | (2006.01) |
| A61K 31/517 | (2006.01) |
| A61K 38/17 | (2006.01) |
| A61K 38/20 | (2006.01) |
| A61K 38/04 | (2006.01) |
| A61K 38/06 | (2006.01) |
| A61K 38/07 | (2006.01) |
| A61K 38/08 | (2006.01) |
| A61K 38/10 | (2006.01) |
| A61K 48/00 | (2006.01) |

(52) U.S. Cl.
CPC .............. *A61K 31/277* (2013.01); *A61K 31/00* (2013.01); *A61K 31/4155* (2013.01); *A61K 31/428* (2013.01); *A61K 31/4406* (2013.01); *A61K 31/498* (2013.01); *A61K 31/517* (2013.01); *A61K 38/1709* (2013.01); *A61K 38/208* (2013.01); *A61K 48/00* (2013.01); *G01N 2500/10* (2013.01)

(58) Field of Classification Search
None
See application file for complete search history.

(56) References Cited

U.S. PATENT DOCUMENTS

| | | |
|---|---|---|
| 4,853,380 A | 8/1989 | Schwartz |
| 4,946,778 A | 8/1990 | Ladner et al. |
| 5,045,316 A * | 9/1991 | Kaplan ......................... 424/400 |
| 5,159,694 A * | 10/1992 | Overath et al. ............ 435/298.2 |
| 5,290,551 A | 3/1994 | Berd |
| 5,716,622 A | 2/1998 | Darnell et al. |
| 5,731,155 A | 3/1998 | Schreiber et al. |
| 5,883,228 A | 3/1999 | Darnell et al. |
| 5,935,993 A | 8/1999 | Tang et al. |
| 5,972,598 A | 10/1999 | Chaudhary et al. |
| 5,976,835 A | 11/1999 | Darnell et al. |
| 6,130,087 A | 10/2000 | Srivastava |
| 6,159,694 A | 12/2000 | Karras |
| 6,235,873 B1 | 5/2001 | Bromberg et al. |
| 6,265,160 B1 | 7/2001 | Leonard |
| 6,426,366 B1 | 7/2002 | Novogrodsky et al. |
| 6,469,013 B2 * | 10/2002 | Uckun et al. ............... 514/266.3 |
| 6,602,709 B1 | 8/2003 | Albert et al. |

(Continued)

FOREIGN PATENT DOCUMENTS

| | | |
|---|---|---|
| CA | 2516685 | 2/2004 |
| WO | WO96/23813 * | 8/1996 |

(Continued)

OTHER PUBLICATIONS

Okabe et al (Leukemia Research, 1994, vol. 18, pp. 867-873).*

(Continued)

*Primary Examiner* — Karen Canella
(74) *Attorney, Agent, or Firm* — Fish & Richardson P.C.

(57) ABSTRACT

Signal Transducer and Activator of Transcription (STAT) proteins have a fundamental role cell signaling, and are activated by a large number of cytokines and growth factors. One member of the STAT family, STAT3, has a critical role in oncogenesis. The present invention relates generally to disruption of the pathway of STAT3 signaling in the treatment of human cancer. STAT3 activation is shown to be present in diverse tumor cell lines and tumors, to promote oncogenesis, to inhibit apoptosis, and to reduce sensitivity to chemotherapeutic agents. Inhibition of STAT3 signaling induces apoptosis specifically in tumor cell lines, and increases sensitivity to chemotherapeutic agents. The invention relates more particularly to methods, compositions, means of administering such compositions, and means for identifying such compositions for the inhibition of STAT3 intracellular signaling in the treatment of human cancers.

6 Claims, 31 Drawing Sheets

(56) References Cited

U.S. PATENT DOCUMENTS

Figure 1:
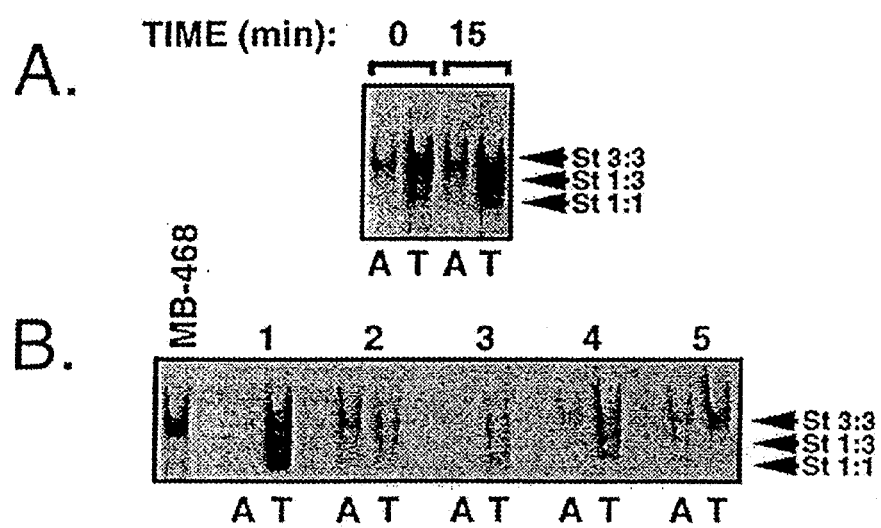

| | | | |
|---|---|---|---|
| 7,348,139 B1 | 3/2008 | Herman et al. | |
| 2009/0305297 A1* | 12/2009 | Hornbeck et al. | 435/7.1 |
| 2009/0325189 A1* | 12/2009 | Hornbeck et al. | 435/7.1 |
| 2011/0045603 A1* | 2/2011 | Guo et al. | 436/501 |

FOREIGN PATENT DOCUMENTS

| | | | |
|---|---|---|---|
| WO | WO97/03358 | * | 1/1997 |
| WO | WO 97/26328 | | 7/1997 |
| WO | WO 98/30688 | | 7/1998 |
| WO | WO 98/41090 | | 9/1998 |
| WO | WO 99/12558 | * | 3/1999 |
| WO | WO 99/28465 | | 6/1999 |
| WO | WO02/18572 | * | 3/2000 |
| WO | WO 00/44774 | | 8/2000 |
| WO | WO 02/18572 | | 3/2002 |
| WO | WO 02/20032 | | 3/2002 |
| WO | WO 2004/080394 | | 9/2004 |

OTHER PUBLICATIONS

Gordon (Methods in Enzymology, 1991, pp. 447-482).*
The abstract of Wasik et al (Leukemia and Lymphoma, Feb. 1998, vol. 28, pp. 551-560).*
Wadia and Dowdy, Advanced Drug Delivery Reviews, 2005, vol. 57, pp. 579-596).*
Johnson and Tracey, 'Peptide and Protein Drug Delivery', In: Encyclopedia of Controlled Drug Delivery, vol. 2, 1999, pp. 816-833).*
Joliot and Prochiantz, Nature Cell Biology, 2004, vol. 6, pp. 189-196.*
Sawada et al, Nature Cell Biology, 2003, vol. 5, pp. 352-357.*
Begley et al (BBRC, 2004, vol. 318, pp. 949-954).*
Garber et al (Journal of the National Cancer Institute, 2005, vol. 97, pp. 1026-1028).*
Sha et al (Molecular Cancer Therapeutics, 2007, vol. 6, pp. 147-153).*
Sandrock et al (Journal of Biotechnology, 2002, vol. 97, pp. 41-50).*
Chakraborty et al (Blood, Jan. 1, 1999, vol. 93, pp. 15-24).*
Bone et al (Journal of Biological Chemistry, 1997, vol. 272, pp. 14470-14476).*
Gerhartz et al (Journal of Biological Chemistry, 1996, vol. 271, pp. 12991-12998).*
Midoh et al, Plant and Cell Physiology (1996), 37(1), 9-18.*
Park et al, PNAS, 1996, vol. 93, pp. 13704-13708.*
"T-9142 Tyrphostin AG 490" [online]. LC Laboratories, [retrieved on Oct. 26, 2004]. Retrieved from the Internet: <URL: www.lclabs.com/PRODFILE/S-Z/T-9142.php4>.
Aftab et al., "Ras-independent transformation by v-Src," *Proc. Natl. Acad. Sci. USA*, 1997, 94:3028-3033.
Bowman et al., "Stat3-mediated Myc expression is required for Src transformation and PDGF-induced mitogenesis," *Proc. Natl. Acad. Sci. USA*, 2001, 98(13):7319-7324.
Coll et al., "Antitumor Activity of *bax* and *p53* Naked Gene Transfer in Lung Cancer: In Vitro and In Vivo Analysis," *Human Gene Therapy*, 1998, 9(14):2063-2074.
Frank et al., "Bystander Effect in the Adenovirus-mediated Wild-Type *p53* Gene Therapy Model of Human Squamous Cell Carcinoma of the Head and Neck," *Clin. Cancer Res.*, 1998, 4:2521-2527.
Garcia et al., "Constitutive activation of Stat3 by the Src and JAK tyrosine kinases participates in growth regulation of human breast carcinoma cells," *Oncogene*, 2001, 20:2499-2513.
Garcia and Jove, "Activation of STAT Transcription Factors in Oncogenic Tyrosine Kinase Signaling," *J. Biomed. Sci.*, 1998, 5:79-85.
Fukada et al., "Two Signals Are Necessary for Cell Proliferation Induced by a Cytokine Receptor gp130: Involvement of STAT3 in Anti-Apoptosis," *Immunity*, 1996, 5:449-460.
Johnson et al., "Overexpressed pp60$^{c-src}$ Can Induce Focus Formation Without Complete Transformation of NIH 3T3 Cells," *Mol. Cell. Biol.*, 1985, 5(5):1073-1083.

Keller and Ershler, "Effect of IL-6 Receptor Antisense Oligodeoxynucleotide on In Vitro Proliferation of Myeloma Cells," *J. Immunol.*, 1995, 154:4091-4098.
Khosravi-Far et al., "Activation of Rac1, RhoA, and Mitogen-Activated Protein Kinases Is Required for Ras Transformation," *Mol. Cell. Biol.*, 1995, 15(11):6443-6453.
Niu et al., "Overexpression of a Dominant-Negative Signal Transducer and Activator of Transcription 3 Variant in Tumor Cells Leads to Production of Soluble Factors That Induce Apoptosis and Cell Cycle Arrest," *Cancer Research*, 2001, 61:3276-3280.
Schwab et al., "Characterization of an Interleukin-6-Mediated Autocrine Growth Loop in the Human Multiple Myeloma Cell Line, U266," *Blood*, 1991, 77(3):587-593.
Tan et al., "Injection of Complementary DNA Encoding Interleukin-12 Inhibits Tumor Establishment at a Distant Site in a Murine Renal Carcinoma Model," *Cancer Res.*, 1996, 56:3399-3403.
Whalen et al., "Megakaryocytic Differentiation Induced by Constitutive Activation of Mitogen-Activated Protein Kinase Kinase," *Mol. Cell. Biol.*, 1997, 17(4):1947-1958.
U.S. Appl. No. 10/383,707, filed Mar. 7, 2003, Yu et al.
U.S. Appl. No. 13/380,020, filed Mar. 7, 2003, Yu et al.
Anderson et al., "Multiple myeloma: new insights and therapeutic approaches," *Hematology Am. Soc. Hematol. Educ. Program*, 2000, pp. 147-165.
Bowman et al., "STATs in Oncogenesis," *Oncogene*, 2000, 19:2474-2488.
Bowman and Jove, "STAT proteins and cancer," *Cancer Control*, 1999, 6:615-619.
Bowman et al., "Signal Transducers and Activators of Transcription: Novel Targets for Anticancer Therapeutics," *Cancer Control*, 1999, 6(5):427-435.
Bright et al., "IL-12 induced JAK-STAT pathway sin T lymphocytes: Regulation by tyrphostin," *J. Allergy Clin. Immunol.*, 1997, 99:S287.
Burger et al., "IL-6 induced proliferation of a myeloma cell line is accompanied by activation of the JAK/STAT pathway and inhibited by tyrphostin AG490," *Ann. Hematol.*, 1998, 77:S2.
Caldenhoven et al., "STAT3β, a Splice Variant of Transcription Factor STAT3, Is a Dominant Negative Regulator of Transcription," *J. Biol. Chem.*, 1996, 271(21):13221-13227.
Campbell et al., "Constitutive activation of KAJ1 in Src transformed cells," *J. Biol. Chem.*, 1997, 272:2591-2594.
Catlett-Falcone et al., "Constitutive Activation of Stat3 Signaling Confers Resistance to Apoptosis in Human U266 Myeloma Cells," *Immunity*, 1999, 10:105-115.
Catlett-Falcone et al., "STAT Proteins as Novel Targets for Cancer Therapy," 1999, *Curr. Opin. Oncology*, 1999, 11:490-496.
Ceresa et al., "Signal Transducer and Activator of Transcription-3 Series Phosphorylation by Insulin Is Mediated by a Ras/Raf/MEK-Dependent Pathway," *Endocrinol.*, 1997, 138:4131-4137.
Dalton et al., "Drug resistance in Multiple Myeloma: Approaches to circumvention," *Sem. Oncol.*, 1999, 26(Supp. 13):23-27.
De Groot et al., "STAT5 activation by BCR-Abl contributes to transformation of K562 leukemia cells," *Blood*, 1999, 94:1108-1112.
Dudley et al., "A Synthetic Inhibitor of the Mitogen-activated Protein Kinase Cascade," *Proc. Natl. Acad. Sci. USA*, 1995, 92:7686-7689
Eck et al., "Gene-Based Therapy," *The Pharmacological Basis of Therapeutics*, 1996, pp. 77-101.
Fan et al., "Dual Leucine Zipper-bearing Kinase (DLK) Activates p46SAPK and p38mapk but not ERK2," *J. Biol. Chem.*, 1996, 271:24788-24793.
Fanger et al., "MEKKs, GCKs, MLKs, PAKs, TAKs, and tpls: Upstream Regulators of the c-Jun Amino-terminal Kinases," *Curr. Opin. Genet. Dev.*, 1997, 7:67-74.
Frank et al., "B Lymphocytes from Patients with Chromic Lymphocytic Leukemia Contain Signal Transducer and Activator of Transcription (STAT) 1 and STAT3 Constitutively Phosphorylated on Serine Residues," *J. Clin. Invest.*, 1997, 100:3140-3148.
Fujio et al., "Signals Through gp130 Upregulate bcl-x Gene Expression Via STAT1-binding cis-Element in Cardiac Myocytes," *J. Clin. Invest.*, 1997, 99:2898-2905.
Garcia et al., "Constitutive Activation of STAT3 in Fibroblasts Transformed by Diverse Oncoproteins and in Breast Carcinoma Cells," *Cell Growth Diff.*, 1997, 8:1267-1276.

(56) References Cited

OTHER PUBLICATIONS

Gollob et al., "The Functional Synergy Between IL-12 and IL-2 Involves p38 Mitogen-Activated Protein Kinase And Is Associated with the Augmentation of STAT Serine Phosphorylation," *J. Immunol.*, 1999, 162:4472-4481.

Grandis et al., "Requirement of STAT3 but not STAT1 Activation for Epidermal Growth Factor Receptor-mediated Cell Growth In Vivo," *J. Clin. Invest.*, 1999, 102(7):1385-1392.

Grigorieva et al., *Blood*, 1996, 10:104A.

Grillot et al., "Genomic Organization, Promoter Region Analysis and chromosome localization of the mouse bcl-x gene," *J. Immunol.*, 1997, 158:4750-4757.

Han et al., "Preferential inhibition of glioblastoma cells with wild-type epidermal growth factor receptors by a novel tyrosine kinase inhibitor ethyl-2,5-dihydroxycinnamate," *Oncol. Res.*, 1997, 9:581-587.

Han et al., "Tyrphostin AG 1478 preferentially inhibits human glioma cells expressing truncated rather than wild-type epidermal growth factor receptors," *Cancer Res.*, 1996, 56(17):3859-3861.

Heller et al., "Treatment of cutaneous and subcutaneous tumors with electrochemotherapy using intralesional bleomycin," DATABASE BIOSIS (online), 1998, 83:148-157.

Horvath et al., "A STAT Protein Domain that Determines DNA Sequence Recognition Suggests a Novel DNA-binding Domain," *Genes Dev.*, 1995, 9:984-994.

Ihle and Kerr, "JAKs and STATSs in Signaling by the Cytokine Receptor Superfamily," *Trends in Genetics*, 1995, 11:69-74.

Johnson and Tracey, "Peptide and Protein Delivery," *Encyclopedia of Controlled Drug Delivery*, 1999, 2:816-833.

Jones et al., *Advanced Drug Delivery Reviews*, 1998, pp. 154 and 160.

Jove et al., "Preface: STAT signaling," *Oncogene*, 2000, 19:2466-2467.

Kelekar et al., "Bad Is a BH3 Domain-Containing Protein That Forms an Inactivating Dimer with Bcl-xl," *Mol. Cell. Biol.*, 1997, 17:7040-7046.

Landowski et al., "Mutations in the Fas Antigen in Patients With Multiple Myeloma," *Blood*, 1997, 90:4266-4270.

Lei et al., "Enhancement of chemosensitivity and programmed cell death by tyrosine kinase inhibitors correlates with EFGR expression in non-small cell lung cancer cells," *Anticancer Res.*, 1999, 19:221-228.

Liang et al., "Chemosensitization of glioblastoma cells to bis-dichloroethyl-nitrosourea with tyrphostin AG17," *Clin. Cancer Res.*, 1998, 4(3):773-781.

Liu et al., "Constitutive activation of the Jak2/Stat5 signal transduction pathway in growth factor-independent megakaryocytic leukemic cell lines," *Blood*, 1999, 93:2369-2379.

Lund et al., "The Src family kinase Lck can induce STAT3 phosphorylation and DNA-binding activity," *Cell Signal*, 1999, 11:789-796.

Lund et al., "Activation of STAT transcription factors by Herpesvirus Saimiri Tip-484 requires p56Lck," *J. Virol.*, 1997, 71:6677-6682.

Meyden et al., "Inhibition of Acute Lymphoblastic Leukaemia by a Jak-2 inhibitor," *Nature*, 1996, 379:645-648.

Nakajima et al., "A central role for Stat3 in IL-6-induced regulation of growth and differentiation in M1 leukemia cells," *EMBO J.*, 1996, 15(14):3651-3658.

Nelson et al., "Activation of STAT3 by the c-Fes protein tyrosin kinase," *J. Biol. Chem.*, 1998, 273:7072-7077.

Nieborowska-Skorska et al., "Signal Transducer and Activator of Transcription (STAT) 5 Activation by BCR/ABL Is Dependent on Intact Src Homology (SH)3 and SH2 Domains of BCR/ABL and Is Required for Leukemogenesis," *J. Exp. Med.*, 1999, 189(8):1229-1242.

Nielsen et al., "Constitutive activation of a slowly migrating isoform of Stat3 in mycosis fungoides: tyrphosin AG490 inhibits Stat3 activation and growth of mycosis fungoides tumor cell lines," *Proc. Natl. Acad. Sci. USA*, 1997, 94(13):6764-6769.

Niu et al., "Gene Therapy with Dominant-negative Stat3 Suppresses Growth of the Murine Melanoma B16 Tumor in Vivo," *Cancer Res.*, 1999, 59:5059-5063.

Orkin et al., "Report and Recommendation of the Panel to Assess the NIH Investment in Research on Gene Therapy," *NIH*, 1995.

Palumbo et al., "Tryphostin AG17 induces apoptosis and inhibition of cdk2 activity in a lymphoma cell line that overexpresses bcl-2," *Cancer Res.*, 1997, 57(12):2434-2439.

Penar et al., "Inhibition of epidermal growth factor receptor-associated tyrosine kinase blocks glioblastoma invasion of the brain," *Neurosurgery*, 1997, 40:141-151.

Pumiglia et al., "Raf-1 N-Terminal Sequences Necessary for Ras-Raf Interaction and Signal Transduction," *Mol. Cell. Biol.*, 1995, 15:398-406.

Sartor et al., "Role of EGF receptor and STAT3 activation in autonomous proliferation of SUM-102PT human breast cancer cells," *Cancer Res.*, 1997, 57:978-987.

Sasse et al., "Mutational Analysis of Acute-Phase Response Factor/Stat3 Activation and Dimerization," *Mol. Cell. Biol.*, 1997, 17(8):4677-4686.

Scott and Smith, "Searching for Peptide Ligands With an Epitope Library," *Science*, 1995, 249:306-390.

Sinibaldi et al., "Induction of p21 AF1/CIP1 and cyclin D1 expression by the Src oncoprotein in mouse fibroblasts: role of activated STAT3 signaling," *Oncogene*, 2000, 19:5419-5427.

Sporeno et al., "Human Interleukin-6 Receptor Super-antagonists with High Potency and Wide Spectrum on Multiple Myeloma Cells," *Blood*, 1996, 87:4510-4519.

Tsai et al., "Enhancement of chemosensitivity by tyrphostin AG825 in high-p185(neu) expressing non-small cell lung cancer cells," *Cancer Res.*, 1996, 56(5):1068-1075.

Turkson et al., "Requirement for Ras/Rac1-Mediated p38 and c-Jun N-Terminal Kinase Signaling in Stat3 Transcriptional Activity Induced by the Src Oncoprotein," *Mol. Cell. Biol.*, 1999, 19:7519-7528.

Turkson and Jove, "STAT proteins: novel molecular targets for cancer drug discovery," *Oncogene*, 2000, 19:6613-6626.

Turkson et al., "Stat3 Activation by Src Induces Specific Gene Regulation and is Required for Cell Transformation," *Mol. Cell. Biol.*, 1998, 18:2545-2552.

Turkson et al., "Phosphotyrosyl peptides blick Stat3-mediated DNA-binding activity, gene regulation and cell transformation," *J. Biol. Chem.*, 2001, 276:45443-45455.

Verma et al., "Gene therapy—promises, problems and prospects," *Nature*, 1997, 389:239-242.

Wadia and Dowdy, "Transmembrane delivery of protein and peptide drugs by TAT-mediated transduction in the treatment of cancer," *Advanced Drug Delivery Reviews*, 2005, 57(4):579-596.

Wagner et al., "The SIF binding element confers sis/PDGF inducibility onto the c-fos promoter," *EMBO J.*, 1990, 9:4477-4484.

Wang et al., "Activation of Stat3 preassmbled with platelet-derived growth factor-beta receptors requires Src kinase activity," *Oncogene*, 2000, 19:2075-2085.

Wasik et al., "Suppression of proliferation and phosphorylation of Jak3 and STAT5 in malignant T-cell lymphoma cells by derivatives of octylamino-undecyl-dimethylxanthine," *Leukemia and Lymphoma*, 1998, 28:551-560.

Whitmarsh et al., "A Mammalian Scaffold Complex that Selectively Mediates MAP Kinase Activation," *Science*, 1998, 281:1671-1674.

Yu et al., "Constitutive activation of the JAK-STAT pathway in T lymphoma overexpressing the Lck protein tyrosine kinase," *J. Immunol.*, 1997, 159:5206-5210.

Yu et al., "Enhanced DNA-Binding Activity of a Stat3-Related Protein in Cells Transformed by the Src Oncoprotein," *Science*, 1995, 269:81-83.

Zhang et al., "Activation of Stat3 in v-Src transformed fibroblasts requires cooperation of Jak1 kinase activity," *J. Biol. Chem.*, 2000, 275:24935-24944.

Zong et al., "Unique Signal Transduction of Eyk: Constitutive Stimulation of JAK-STAT Pathway by an Oncogenic Receptor-type Tyrosine Kinase," *EMBO J.*, 1996, 15:4515-4525.

(56) References Cited

OTHER PUBLICATIONS

Zushi et al., "STAT3 mediates the survival signal in oncogenic ras-transfected intestinal epithelial cells," *Int. J. Cancer*, 1998, 78(3):326-330.
Zushi et al., "Role of heparin-binding EGF-related peptides in proliferation and apoptosis of activated ras-stimulated intestinal epithelial cells," *Int. J. Cancer*, 1997, 73(6):917-923.
Office Action in CA 2,361,621 dated Mar. 18, 2008.
Examination Report in EP Appl. 00905724.1 dated Jul. 22, 2005.
European Search Report in EP 07010488.0 dated Jun. 19, 2008.
Bachmann et al., "Recall Proliferation Potential of Memory CD8+ T Cells and Antiviral Protection," *J. Immunol.*, 2005, 175:4677-4685.
Bohm et al., "Interleukin-6-resistant melanoma cells exhibit reduced activation of STAT3 and lack of inhibition of cyclin E-associated kinase activity," *J. Invest. Dermatol.*, 2001, 117:132-140.
Efferson et al., "Stimulation of Human T Cells by an Influenza A Vector Expressing a CTL Epitope from the HER-2/neu Protooncogene Results in Higher Numbers of Antigen-specific TCR[hi] Cells than Stimulation with Peptide. Divergent Roles of IL-2 and IL-15," *Anticancer Research*, 2005, 25:715-724.
Jones et al., "Antibodies for targeted gene therapy: extracellular gene targeting and intracellular expression," *Adv. Drug Delivery Rev.*, 1998, 31:153-170.
Ko et al., "Polymethoxyflavonoids from Vitex rotundifolia inhibit proliferation by inducing apoptosis in human myeloid leukemia cells," *Food Chem. Toxicol.*, 2000, 38:861-865.
Matzinger, "Tolerance, danger, and the extended family," *Ann. Rev. Immunol.*, 1994, 2:991-1045.
Todryk et al., "Heat shock proteins refine the danger theory," *Immunology*, 2000, 99:334-337.
Wheeler, "Preventive vaccines for cervical cancer," *Salud p'ublica de M'exico*, 1997, 39(4):283-287, (Abstract only).
Negoro et al., "Activation of JAK/STAT pathway transduces cytoprotective signal in rat acute myocardial infarction," *Cardiovascular Res.*, 2000, 47:797-805.
Negoro et al., "Activation of signal transducer and activator of transcription 3 protects cardiomyocytes from hypoxia/reoxygenation-induced oxidative stress through the upregulation of manganese superoxide dismutase," *Circulation*, 2001, 104:979-981.
Yamauchi-Takihara and Kishimoto, "A novel role for STAT3 in cardiac remodeling," *Trends Cardiovascular Med.*, 2000, 10(7):298-303.
Canadian Patent Office, Office Action issued in Canadian Patent Application No. 2,361,621, dated Dec. 7, 2011, 4 pages.
Bright and Sriram, "TGFβ Inhibits IL-12-Induced Activation of Jak-STAT Pathway in T Lymphocytes," *The Journal of Immunology*, Aug. 1998, 161:1772-1777.
Bromberg and Darnell Jr., "The role of STATs in transcriptional control and their impact on cellular function," *Oncogene*, May 2000, 19:2468-2473.
Bromberg et al., "Stat3 as an oncogene," *Cell*, Aug. 1999, 98(3):295-303.
Cheng et al., "Role of Signal Transducer and Activation of Transcription 3 (STAT-3) in Immune Tolerance: Blockade of Stat3 Signaling in Antigen-Presenting Cells (APCs) Breaks Antigen-Specific T-Cell Anergy," *Blood*, Nov. 2002, 100(11):35 (abstract only).
Cheng et al., "Inhibition of STAT signaling by a JAK-kinase selective inhibitor tyrphostin AG490 enhances antigen-presenting cells (APCs) function in vitro and in vivo," *Blood*, Nov. 2000, 96(1):238a (abstract only).
Cote et al., "Generation of human monoclonal antibodies reactive with cellular antigens," *Proc. Natl. Acad. Sci. U.S.A.*, Apr. 1983, 80:2026-2030.
Darnell Jr., "STATs and Gene Regulation," *Science*, Sep. 1997, 277:1630-1635.
Darnell Jr. et al., "Jak-STAT pathways and transcriptional activation in response to IFNs and other extracellular signaling proteins," *Science*, Jun. 1994, 264(5164):1415-1421.
Funamoto et al., "Signal Transducer and Activator of Transcription 3 Is Required for Glycoprotein 130-mediated Induction of Vascular Endothelial Growth Factor in Cardiac Myocytes," *The Journal of Biological Chemistry*, Apr. 2000, 275(14):10561-10566.
Grandis et al., "Constitutive activation of Stat3 signaling abrogates apoptosis in squamous cell carcinogenesis in vivo," *Proc. Natl. Acad. Sci. USA*, Apr. 2000, 97(8):4227-4232.
Her, et al "Dual phosphorylation and autophosphorylation in mitogen-activated protein (MAP) knase activation," *Biochem. J.*, Nov. 1993, 296:25-31.
Kohler and Milstein, "Continuous cultures of fused cells secreting antibody of predefined specificity," *Nature*, Aug. 1975, 256:495-497.
Korpelainen et al., "Endothelial receptor tyrosine kinases activate the STAT signaling pathway: mutant Tie-2 causing venous malformations signals a distinct STAT activation response," *Oncogene*, Jan. 1999, 18:1-8.
Kozbor et al., "The production of monoclonal antibodies from human lymphocytes," *Immunology Today*, Mar. 1983 4:72-79.
McLemore et al., "STAT-3 Activation Is Required for Normal G-CSF-Dependent Proliferation and Granulocytic Differentiation," *Immunity*, Feb. 2001, 14:193-204.
Niu et al., "Constitutive Stat3 activity up-regulates VEGF expression and tumor angiogenesis," *Oncogene*, Mar. 2002, 21:2000-2008.
Niu et al., "Gene Therapy with Dominant-negative Stat3 Suppresses Growth of the Murine Melanoma B16 Tumor in Vivo," *Cancer Research*, Oct. 1999, 59:5059-5063.
Sano et al., "Keratinocyte-specific ablation of Stat3 exhibits impaired skin remodeling, but does not affect skin morphogenesis," *EMBO J.*, Sep. 1999, 18(17):4657-4668.
Shen et al., "Constitutively activated Stat3 protects fibroblasts from serum withdrawal and UV-induced apoptosis and antagonizes the proapoptotic effects of activated Stat1," *Proc. Natl. Acad. Sci. USA*, Feb. 2001, 98(4):1543-1548.
Starr and Hilton, "Negative regulation of the JAK/STAT pathway," *Bioessays*, Jan. 1999, 21(1):47-52.
Takeda et al., "Enhanced Th1 activity and development of chronic enterocolitis in mice devoid of Stat3 in macrophages and neutrophils," *Immunity*, Jan. 1999, 10(1):39-49.
Xu et al., "Targeting Stat3 blocks both HIF-1 and VEGF expression induced by multiple oncogenic growth signaling pathways" *Oncogene*, Aug. 2005 24:5552-5560.

\* cited by examiner

Fas mediated apoptosis in U266 cells

In Vitro SH2·P-Y Interaction Assay

INHIBITION OF STAT3 SIGNAL TRANSDUCTION FOR HUMAN CANCER THERAPY

RELATED APPLICATIONS

This application is a continuation and claims the benefit of priority under 35 U.S.C. §120 of U.S. application Ser. No. 09/492,764, filed Jan. 27, 2000 now abandoned, which claims priority of U.S. Provisional Application No. 60/117,600, filed Jan. 27, 1999, all of which are incorporated by reference in their entirety herein.

STATEMENT OF FEDERAL SUPPORT

The present invention was made in whole or in part with financial support from the Federal Government under grants CA77859, CA55652, and CA75243 from the National Cancer Institute. The Federal Government may have certain rights in this invention.

1. FIELD OF THE INVENTION

The present invention relates generally to intracellular receptor recognition proteins involved in signal transduction, and to the role of such proteins in the promotion and maintenance of pathogenic and non-pathogenic cell growth; to methods and compositions reactive towards such proteins, or indirectly influencing their function; to the use of such compositions in assays, diagnosis or in treatment; to methods and assays whereby compositions reactive to such proteins may be identified; and to means for introducing such compositions into cells. More particularly, the invention relates to STAT (Signal Transducer and Activator of Transcription) proteins, in particular STAT3, demonstrated to participate in intracellular events resulting in aberrant cell growth, to compositions and methods for inhibition of STAT signaling, and to interference with STAT3 signaling for the purpose of inhibiting malignant transformation, cancerous growth, and oncogenesis.

2. BACKGROUND OF THE INVENTION

Studies of interferon (IFN)-dependent gene expression have led to the elucidation of pathways that signal directly from the cell surface to the nucleus. The Signal Transducers and Activators of Transcription (STATs) are essential mediators of signaling in these direct pathways. The STATS comprise a family of transcription factors that are activated by tyrosine kinases in the cytoplasm and then migrate to the nucleus where they directly regulate gene expression.

Seven mammalian STAT family members (Stat1-Stat6, with STAT5a and STAT5b representing distinct genes) have been molecularly cloned and share common structural elements, including a Src-homology 2 (SH2) domain. Monomeric, inactive STAT proteins associate with each other to form active dimers through a key phosphotyrosine (pY) residue, which binds to the SH2 domain of another STAT monomer. Reciprocal SH2-pY interactions are critical for STAT functions, including nuclear transport and DNA binding. The DNA-binding domain resides in the N-terminal portion of the STAT molecule (Horvath, et al., 1995, Genes Dev. 9:984-994). Located within the C-terminal portion is the transactivation domain, which contains critical serine residue, the phosphorylation of which is required for maximal transcriptional activity.

The signal cascade initiates when cytokines (such as IFNs and members of the interleukin family) or growth factors (epidermal growth factor and platelet-derived growth factor, for example) bind to their cognate cell surface receptors. Certain growth factor receptors possess intrinsic tyrosine kinase activity and phosphorylate STATs directly, thereby activating STAT signaling. In contrast, cytokine receptors lack intrinsic kinase activity, and recruit members of the Janus kinase (JAK) family of cytoplasmic tyrosine kinases to activate STATs. JAK family kinases have been shown to be involved in STAT activation (Ihle & Kerr, 1995, Trends in Genetics, 11:69-74). Depending on which STAT family members are activated, STATs may associate as homodimers or heterodimers, and then translocate to the nucleus, whereupon the activated STAT dimers bind to specific DNA-response elements in promoters, and induce expression of target genes.

Certain non-STAT3 STAT proteins and chimeric peptides derived from them were described by Darnell, Jr., et al. (U.S. Pat. No. 5,716,622, published Feb. 10, 1998). In related patents, further non-STAT3 STAT DNA sequences were disclosed, and chimeric STAT proteins were claimed (U.S. Pat. Nos. 5,883,228, published Mar. 16, 1999; U.S. Pat. No. 5,976, 835, published Nov. 2, 1999). Thus, the STAT proteins appear to have a role in the regulation of cell growth. Constitutive activation of various members of the STAT family has been reported in different cell lines. The present invention significantly extends the characterization of STAT3's role in growth regulation and ocogenesis, beyond those described previously, and establishes rationale for modulation of STAT3 signaling for the purpose of treating patients with cancerous conditions. The present invention addresses that need by advancing means for such regulation.

3. SUMMARY OF THE INVENTION

In its broadest aspect, the present invention is related to the identification of the role of STAT3 activation in tumorigenesis, and the related phenomena of resistance to apoptosis and resistance of tumor cells to chemotherapeutic agents. In particular, the present invention relates to disruption of STAT3 intracellular signaling in the treatment tumors and in the prevention of tumorigenesis.

Present inventors disclosure herein that the oncogenic tyrosine kinases, viral Src (v-Src) and cellular Src (c-Src), constitutively induce STAT3 DNA-binding activity in stably-transformed rodent fibroblast cell lines. This comprises the first report of activation of STAT signaling by a specific oncoprotein. It is disclosed herein that activation of STAT3 DNA-binding activity by the Src oncoprotein leads to induction of STAT3-specific regulation of gene expression. Moreover, they establish that STAT3 signaling is required for oncogenesis by Src using a dominant-negative form of STAT3 protein that interferes with STAT3-mediated signaling and blocks cell transformation. These findings provided the first direct evidence that STAT signaling has a causal role in oncogenesis.

Accordingly, in a first aspect, the invention is directed to a method of inhibiting the growth of cancer cells in a patient though administration of antagonists of STAT3 signaling. In particular, STAT3 is shown to be constitutively activated in several human tumors and tumor cell lines. Furthermore, such activation possesses two features which suggest opportunities for therapeutic intervention. Firstly, it is shown that certain tumors and tumor cell lines are dependent upon constitutive activation of STAT3, while untransformed cell lines are not. Secondly, antagonists of STAT3 signaling promote apoptosis in certain transformed, but not untransformed, cell lines. These are not general characteristics of all STAT protein family members, but represent novel characteristics discovered by the inventors. Thus, due to these specific properties, STAT3 is a suitable target for therapeutic intervention in the treatment of human cancer. In this first aspect, inhibition of STAT3 signaling is accomplished in a number of ways. Dimerization of STAT3 through key phosphotyrosine residues is required for activation, and so dimerization requires tyrosine phosphorylation. Inhibitors of tyrosine kinases that inhibit STAT3 signaling, include but not limited to tyrphostins, in particular AG-490, and inhibitors of Jak, Src, BCR-Abl tyrosine kinases. Other tyrphostins suitable for use in the present invention include, but are not limited to AG17, AG213 (RG50864), AG18, AG82, AG494, AG825, AG879, AG1112, AG1296, AG1478, AG126, RG13022, RG14620, AG555, and related compounds. It is shown herein that AG-490 inhibits STAT3 in tumor cell lines in a manner that correlates with inhibition of tumor cell growth. It is further known that the malignant progression and survival of certain tumor cell lines is dependent upon the presence of cytokines. For example, malignant progression of multiple myeloma requires IL-6, which was previously known to elevate Bcl-x, levels within the cell. Herein it is shown for the first time how blocking the IL-6 pathway blocks STAT3 activation and decreases transcription of the Bcl-x gene. Therefore, in this first aspect, inhibition of STAT3 activation is also accomplished by cytokine antagonism where the cytokine is an activator of STAT3, or by blocking STAT3-dependent transcriptional activation.

In a second aspect of the present invention, it has been discovered that inhibition of STAT3 signaling selectively promotes apoptosis in tumor cells that harbor constitutively activated STAT3. Therefore, in this second aspect, the desirable goal of promoting apoptosis ("programmed cell death) of selective cancerous cells within a patient is likewise accomplished through administration of antagonists or inhibitors of STAT3 signaling in a suitable pharmaceutical formulation.

In a third aspect, inhibition of STAT3 activation is shown to be an effective means for inhibiting tumorigenesis. Therefore, an additional aspect of the present invention is prevention of tumor formation through inhibition of tumorigenesis or neoplastic transformation. In mouse fibroblasts transformed by the Src oncoprotein, it is shown herein that blocking the constitutive activation of STAT3 signaling causes significant suppression of cell transformation and tumor cell growth and induces human tumor cells to undergo apoptosis.

Apoptosis is both an essential mechanism for the maintenance of normal cellular growth control, and also a key mechanism whereby many chemotherapeutic agents destroy cancer cells. It is demonstrated herein that the effectiveness of chemotherapeutic agents is enhanced by inhibition of the STAT3 signaling pathway, whereby transcription of antiapoptotic factors such as Bcl-x, is blocked. Resistance to chemotherapeutic agents and radiotherapy, which often develops during treatment, has been attributed in part to increases in the intracellular expression of Bcl-x, like proteins. Thus, it is an objective of the present invention, in a fourth aspect, to enhance the effectiveness of chemotherapeutic or radiation treatment of human cancer patients through inhibition of the STAT3 signaling pathway.

In a fifth aspect, it is demonstrated that solid tumor growth can be inhibited by introducing into the tumor cells agents that inhibit STAT3 signaling. A surprising and unanticipated benefit of this regime in the treatment of solid tumors is that the apoptosis thus induced is not confined to only the cells in which STAT3 signaling is blocked. Instead, surrounding tumor cells, but not surrounding normal cells, are also killed, enhancing the efficacy of this approach beyond that achievable if only cells into which inhibitory agents were directly introduced were affected. Antitumor bystander effects, such as described herein, have also been observed in tumors treated with p53 gene therapy (Coll, et al., 1998, Human Gene Therapy 9; 2063-2074, 1998, Frank, et al., 1998, Clin. Cancer Res. 4: 2521-2528). A recent report demonstrated 29% growth inhibition of non-transduced cells after p53-transduced and non-transduced cells were co-cultured in vitro (Frank, et al., 1998, Clin. Cancer Res. 4: 2521-2528). In this aspect, agents that disrupt STAT3 signaling are introduced into accessible solid tumors, and in a preferred embodiment, a genetic construct encoding a STAT3 splice variant that results in formation of inactive STAT3 dimers, is used.

In a further aspect of the invention, it is shown that co-administering immunotherapeutic agents such as IL-12 is advantageous in combination treatment of cancers such as multiple myeloma. Such combination is beneficial because cytokine-based immunotherapies are effective means of generating protective antitumor immunity in hosts with minimal tumor burdens. Therefore, where inhibition of STAT3 signaling results in eradication of most, but not all, of the tumor burden, or the effectiveness of such treatment is transient as is the case with mouse myeloma cells, immunotherapy is an attractive means for the prevention of recurrence. However, it was not obvious that such combination would be possible, because many cytokines including IL-12 are known to signal through the JAK-STAT pathway. It is the surprising discovery of the inventors, disclosed herein, that inhibition of STAT3 signaling by AG-490, a tyrosine kinase inhibitor, does not reduce the IL-12 mediated activation of macrophage cytotoxicity essential to IL-12 immunotherapy. Furthermore, the combinational therapy of this aspect of the invention results in prolonged tumor regression.

In a still further aspect of the present invention, it is desirable to identify specific compounds that inhibit STAT3 signaling. Specifically, peptides that bind to STAT3, deletion variants thereof, the SH2 domain of STAT3, or disrupt STAT3-DNA binding are specifically disclosed. Short peptides exhibiting these binding characteristics are identified as described herein, that are efficient inhibitors and potential lead compounds for future development of novel anti-cancer drugs.

In a final embodiment, it is a further object of the present invention to provide means for the efficient screening of potential inhibitors of STAT3 signaling. Traditional means require expensive isotopes and time-consuming gel electrophoresis. In the final embodiment, rapid and inexpensive screening means are disclosed, in which STAT3 transcriptional activity is non-radioactively detected through the use of luciferase reporter genes linked to appropriate promoter sequences, including a STAT3-responsive promoter.

Other objects and advantages will become apparent to those skilled in the art from a review of the ensuing description which proceeds with reference to the following illustrative drawings.

4. BRIEF DESCRIPTION OF THE DRAWINGS

FIG. 1: EMSA Analysis of STAT DNA-Binding Activity in Breast Tumors. Tumor (T) tissue and adjacent (A) non-tumor tissue is analyzed by EMSA using the hSIE probe. Positions of the various dimers containing STATs 1 and 3 are indicated. Panel A: Specimens are snap frozen at the time of excision (0 time) or 15 minutes later following processing by Pathology. Panel B: Additional tumor specimens compared to the MDA- MB-468 breast carcinoma cell line. Results demonstrate increased STAT activities in the majority of tumor specimens compared to matched non-tumor controls.

Figure 2:
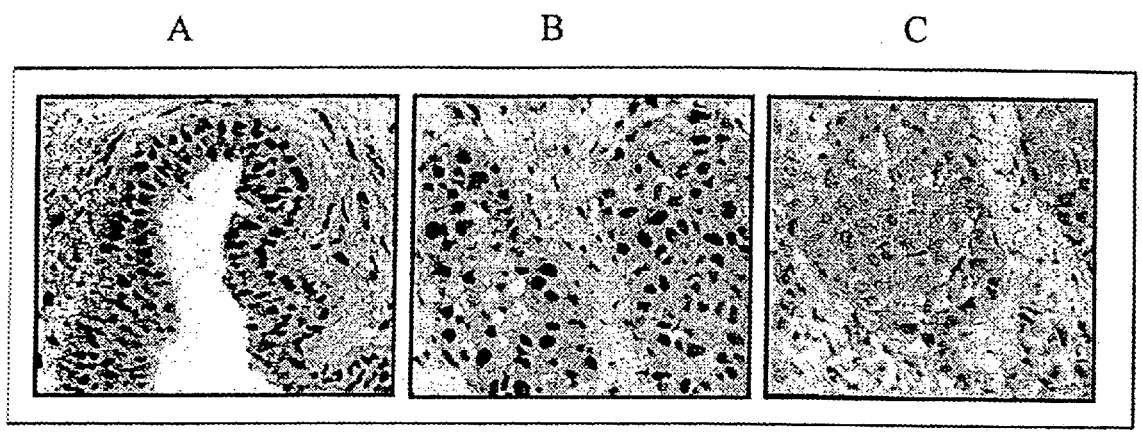

FIG. 2: Immunohistochemical Analysis of STAT3 Activation in Breast Tissues. Panel A: Nuclear staining with antibodies to phospho-STAT3 (pY-STAT3) reveals activated STAT3 in the proliferative (basal) layer of normal ductal epithelium. Panel B: Increased levels of activated, nuclear pY-STAT3 are detected in breast carcinoma cells compared to surrounding non-tumor cells. Panel C: Competition of pY-STAT3 staining with the corresponding phospho-STAT3 peptide antigen demonstrates specificity of antibodies.

Figure 3:
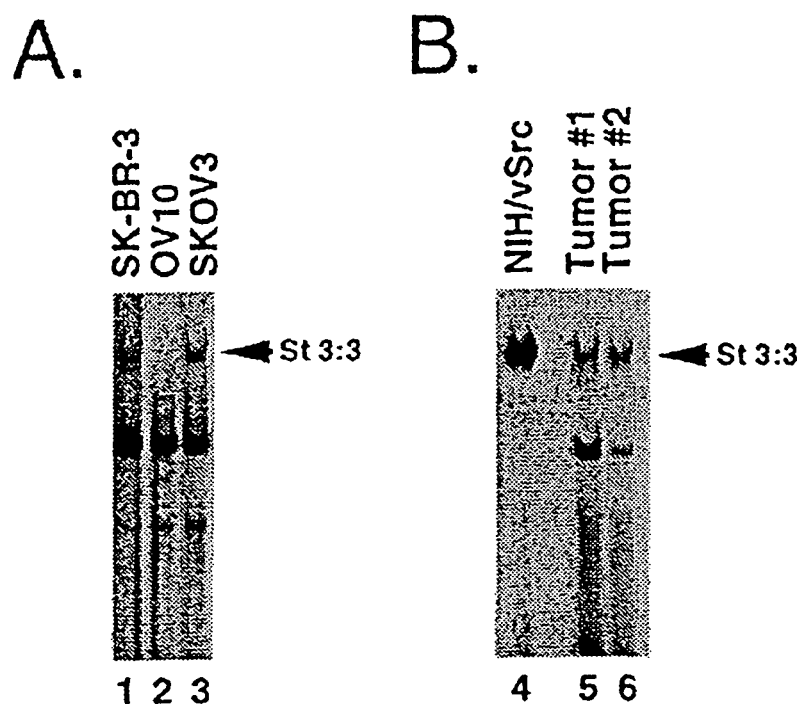

FIG. 3: STAT3 DNA-Binding Activity in Ovarian Cancer. Panel A: EMSA is performed with the hSIE probe using nuclear extracts prepared from human ovarian cancer cell lines, SKOV3 and OV10, compared to the breast cancer cell line, SK-BR-3. Panel B: EMSA of two primary ovarian tumors compared to v-Src transformed cells. Results demonstrate activation of STAT3 in ovarian tumor cells.

Figure 4:
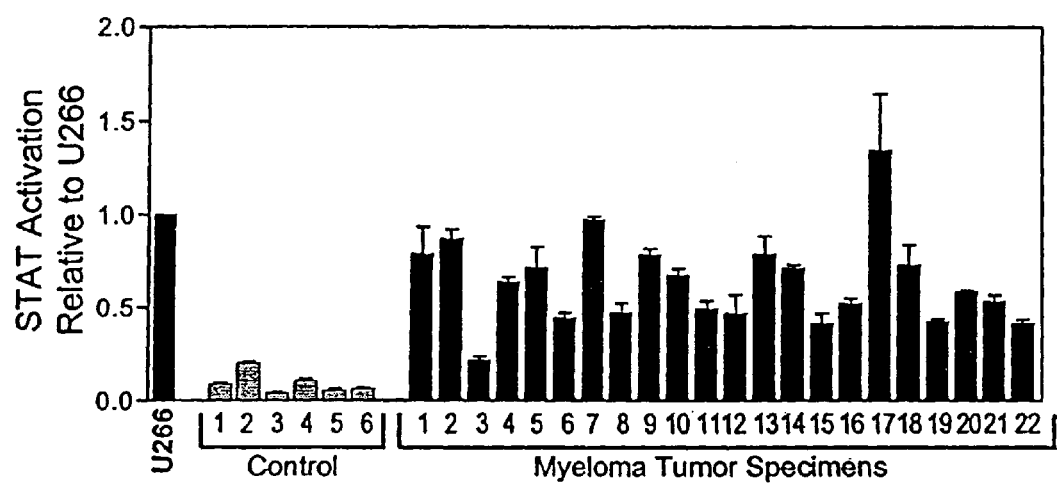

FIG. 4: Reproducibility of EMSA for Measuring STAT Activation in Myeloma Tumors. Levels of STAT activation in tumor specimens are shown relative to the U266 cell line, which has a constitutively-high level of STAT activation. In this case, the controls are bone marrow specimens from normal donors or patients without evidence of bone disease. Data represent the means plus standard deviations from 3 independent analyses by EMSA for each specimen.

Figure 5:
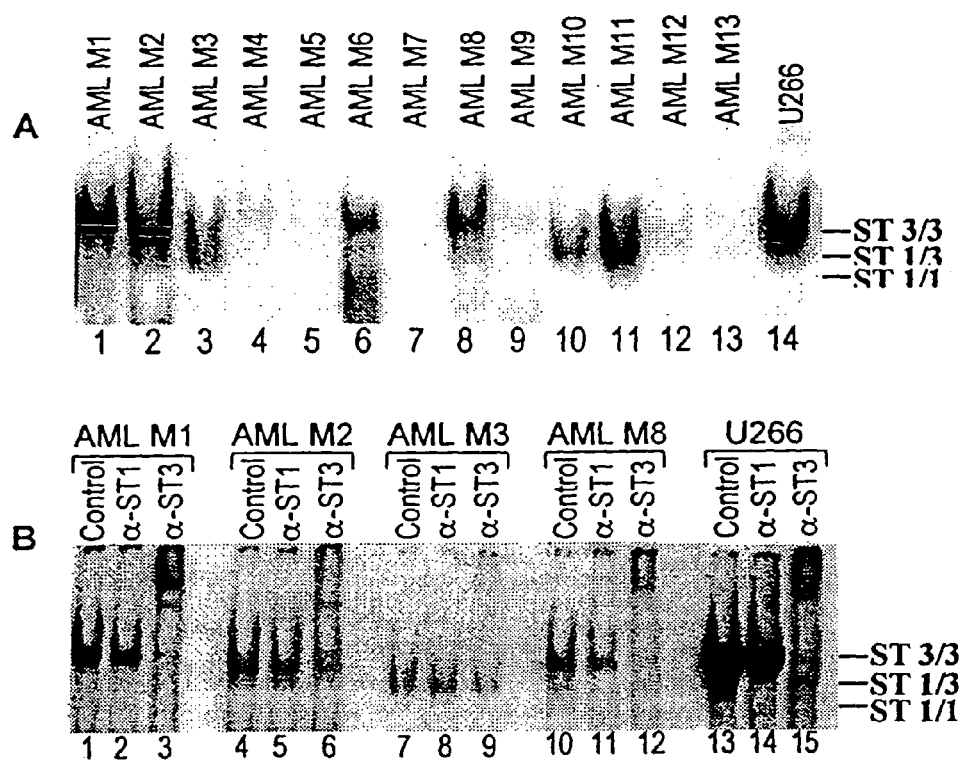

FIG. 5: Activation of STATs in Bone Marrow Tumor Specimens from AML Patients. Nuclear extracts from AML tumor specimens are analyzed by EMSA using the labeled hSIE probe (Panel A). U266 cells are used as a positive control. Supershift analyses are performed to identify the activated dimers containing STATs 1 and 3 (Panel B). Results demonstrate frequent activation of STATs in AML tumors.

Figure 6:
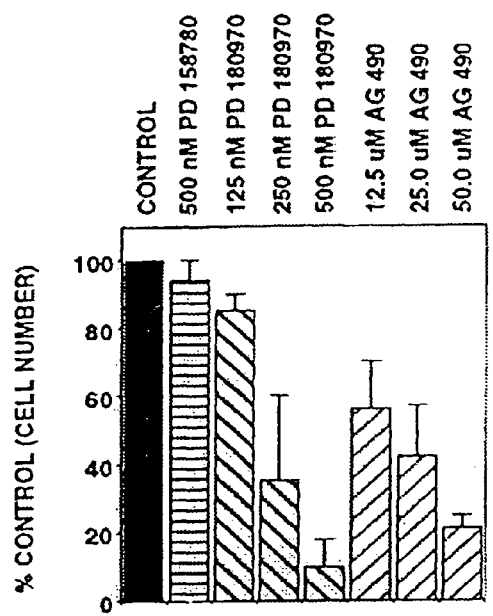
Figure 6:
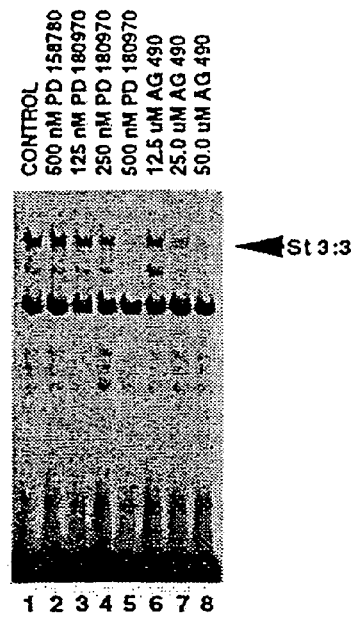

FIG. 6: Src and JAK Inhibitors Block Growth and STAT3 Activation in Breast Carcinoma Cells. MDA-MD-468 cells are treated with inhibitors of EGF receptor (PD158780), Src (PD180970), or JAKs (AG490), and effects on cell growth (Panel A) and STAT3 DNA-binding activity (Panel B) are determined.

Figure 7:
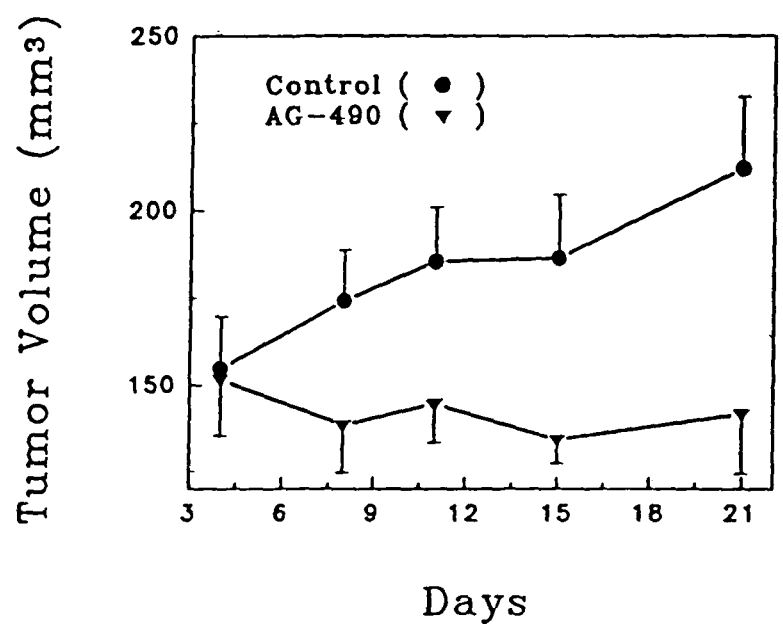

FIG. 7: AG490 Blocks Tumorigenicity of Breast Carcinoma Cells. Nude mice are engrafted with MDA-MB-468 tumor cells, and then treated with AG490 by mini-pump infusion (42 mpk) and daily intraperitoneal injections (50 mpk). Results show significant inhibition of tumor growth by AG490 treatment.

Figure 8:
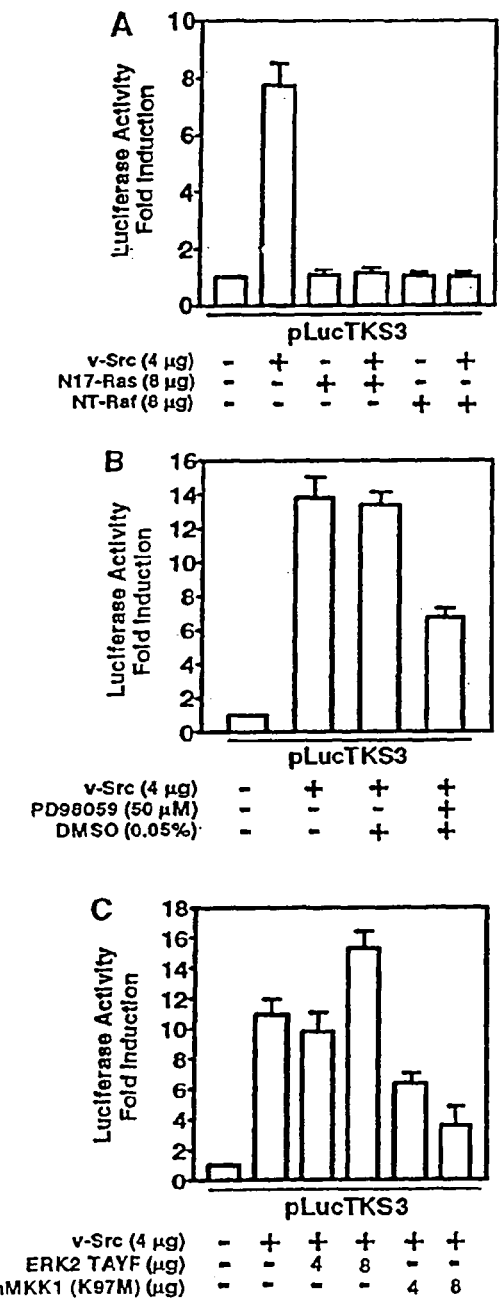

FIG. 8. Ras-MKK1/2-dependent signaling is required for STAT3-mediated gene regulation induced by v-Src. NIH 3T3 cells are transiently transfected with indicated plasmids. Luciferase activities are measured in cytosolic extracts prepared 48 hours post-transfection and normalized to b-galactosidase (b-gal) activity. (A) NIH 3T3 cells are transfected with pLucTKS3 reporter alone, or reporter and v-Src expression vector, pMvSrc, together with or without vectors encoding N17-Ras or NT-Raf as indicated. The N17-Ras and NT-Raf proteins inhibit Ras in a dominant-negative manner. (B) Cells are transfected with reporter alone, or reporter and pMvSrc and treated with or without MKK112 inhibitor, PD98059, for 6 h. (C) Cells are transfected with reporter alone, or reporter and pMvSrc with or without vectors encoding the dominant-negative ERK2 mutant, TAYF, or MKK1 dominant-negative, dnMKK1. Values shown in each panel are means plus standard deviations of at least four independent transfections, each performed in triplicate.

Figure 9:
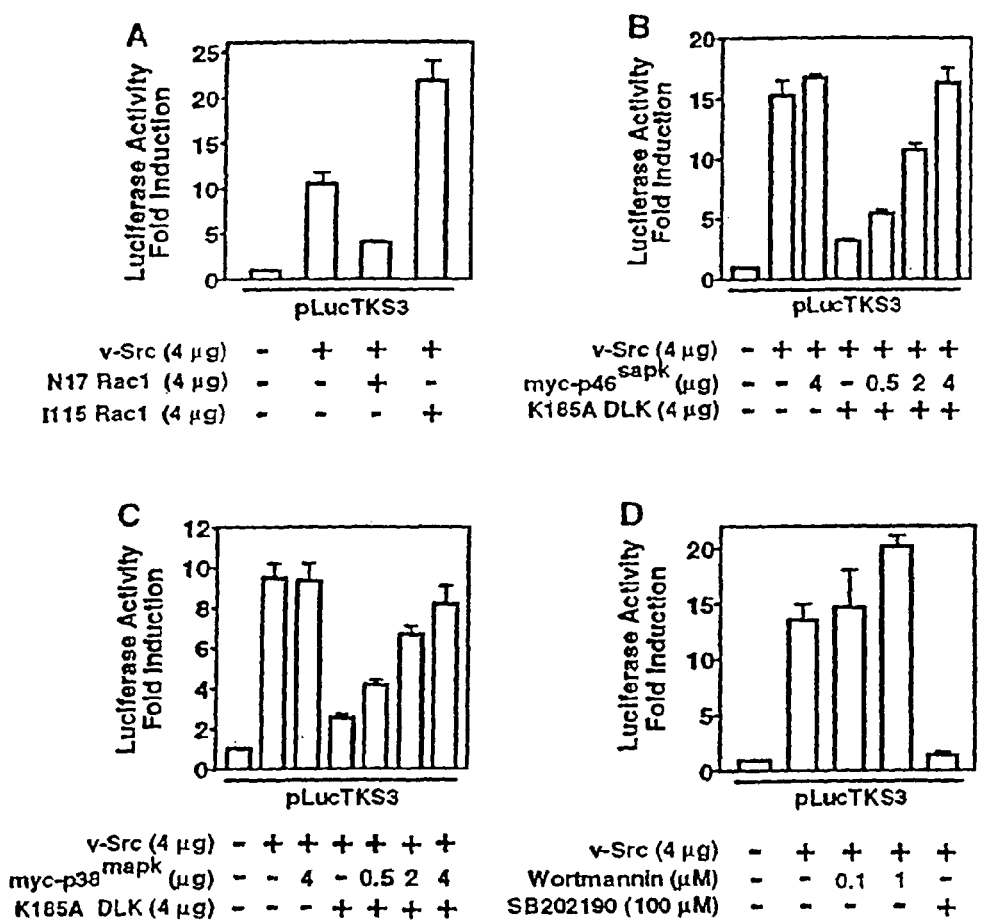

FIG. 9. STAT3-mediated gene regulation induced by v-Src requires Rac1- and MLK-dependent p38 and JNK signals. NIH 3T3 cells are transiently transfected with the indicated plasmids, and luciferase activities are assayed. (A) Cells are transfected with STAT3 reporter pLucTKS3 alone, reporter and v-Src, or reporter, v-Src and dominant-negative Rac1 (N17 Rac1), or activated Rac1 (I1 15 Rac1). (B) Cells are transfected with reporter alone, reporter and v-Src, or reporter, v-Src and dominant-negative DLK (K185A), or p4VPk, or both. (C) Cells are transfected with reporter alone, reporter and v-Src, or reporter, v-Src and K185A. or $p38^{mapk}$, or both. (D) Cells are transfected with reporter alone, or reporter and v-Src and treated with or without $p38^{mapk}$ inhibitor, SB202190, or PI 3-kinase inhibitor, wortmannin. Values are means plus standard deviations of at least three independent experiments.

Figure 10:
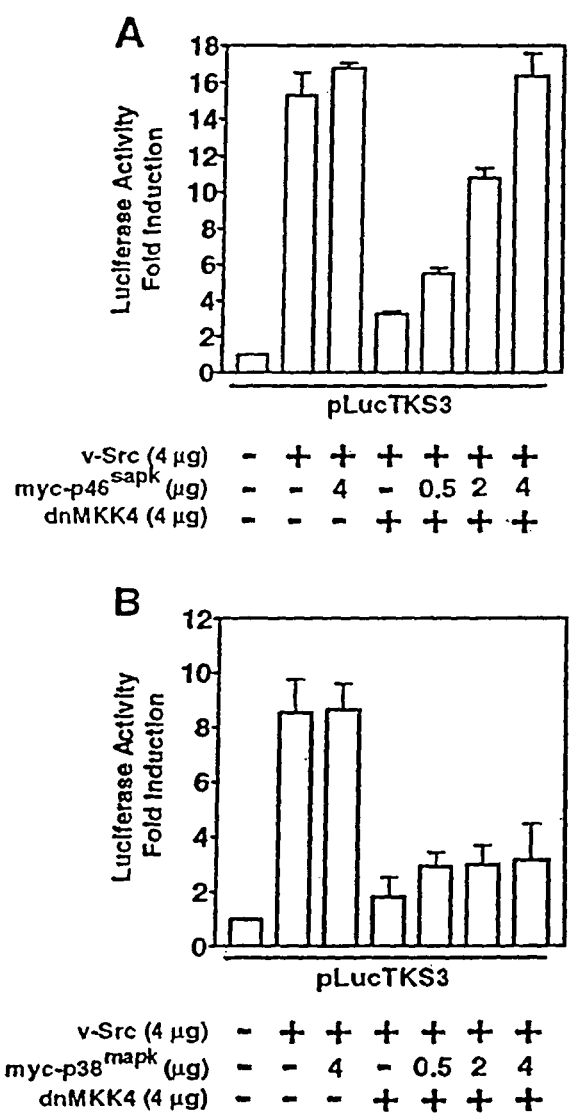

FIG. 10. v-Src-induced STAT3-mediated gene regulation requires MKK4-dependent JNK signaling. NIH 3T3 cells are transiently transfected with the indicated plasmids vectors, and luciferase activities are assayed. (A) Cells are transfected with pLucTKS3 reporter alone, reporter and v-Src, or reporter, v-Src and dnMKK4 or myc-p46'"Pk, or both. (B) Cells are transfected with reporter alone, reporter and v-Src, or reporter, v-Src and dnMKK4, or myc-$p38^{mapk}$, or both. Values are means plus standard deviations of at least three independent transfections.

Figure 11:
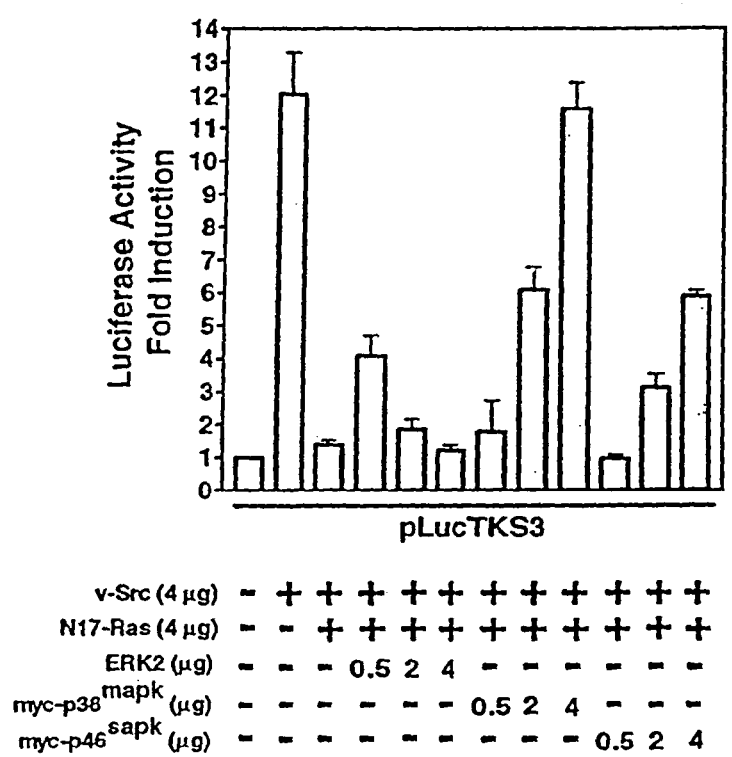

FIG. 11. STAT3-mediated gene regulation induced by v-Src requires Ras-dependent $p38^{mapk}$ and JNK activities. NIH 3T3 cells are transiently transfected with pLucTKS3 reporter alone, reporter and v-Src, or reporter, v-Src and N17-Ras with or without vectors encoding ERK2, myc-$p38^{mapk}$ or myc-$p46^{sapk}$. Luciferase activities are assayed. Values are means plus standard deviations of three independent experiments.

Figure 12:
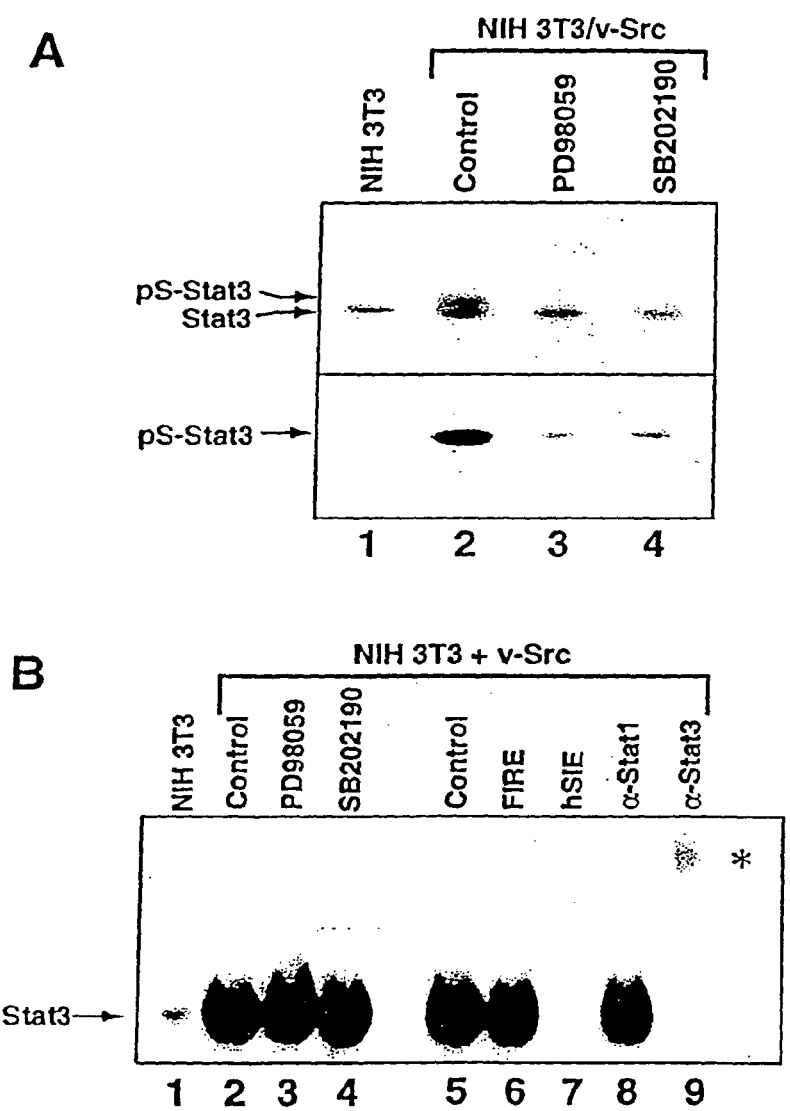

FIG. 12. Analyses of constitutive STAT3 serine phosphorylation and SIE-binding activity induced by v-Src. (A) Western blot analysis of whole-cell lysates prepared from normal NIH 3T3 fibroblasts and Src-transformed counterparts treated with or without PD98059 or SB202190 for 6 hours (lanes 2 to 4). Samples are probed with antibodies specific to phosphoserine-727 (lower panel) or the N-terminal portion (upper panel) of STAT3. (B) Nuclear extracts are prepared from NIH 3T3 cells transfected with v-Src. Equal amounts of total protein are incubated with 32P-labeled M67SIE and subjected to EMSA. Cells are transfected with empty vector alone (NIH 3T3), or v-Src vector and treated with or without PD98059 or SB202190 for 6 hours (lanes 2 to 5). Competitions of radiolabeled M67SIE binding activity present in nuclear extracts of NIH 3T3 cells transfected with v-Src alone (lanes 6 and 7) are performed with a 100-fold molar excess of unlabeled M67SIE or the unrelated c-fos intragenic regulatory element (FIRE) oligonucleotides. Supershifts (lanes 8 and 9) are performed with antibodies specifically recognizing either STAT1 or STAT3. Asterisk indicates positions of supershifted complexes.

Figure 13:
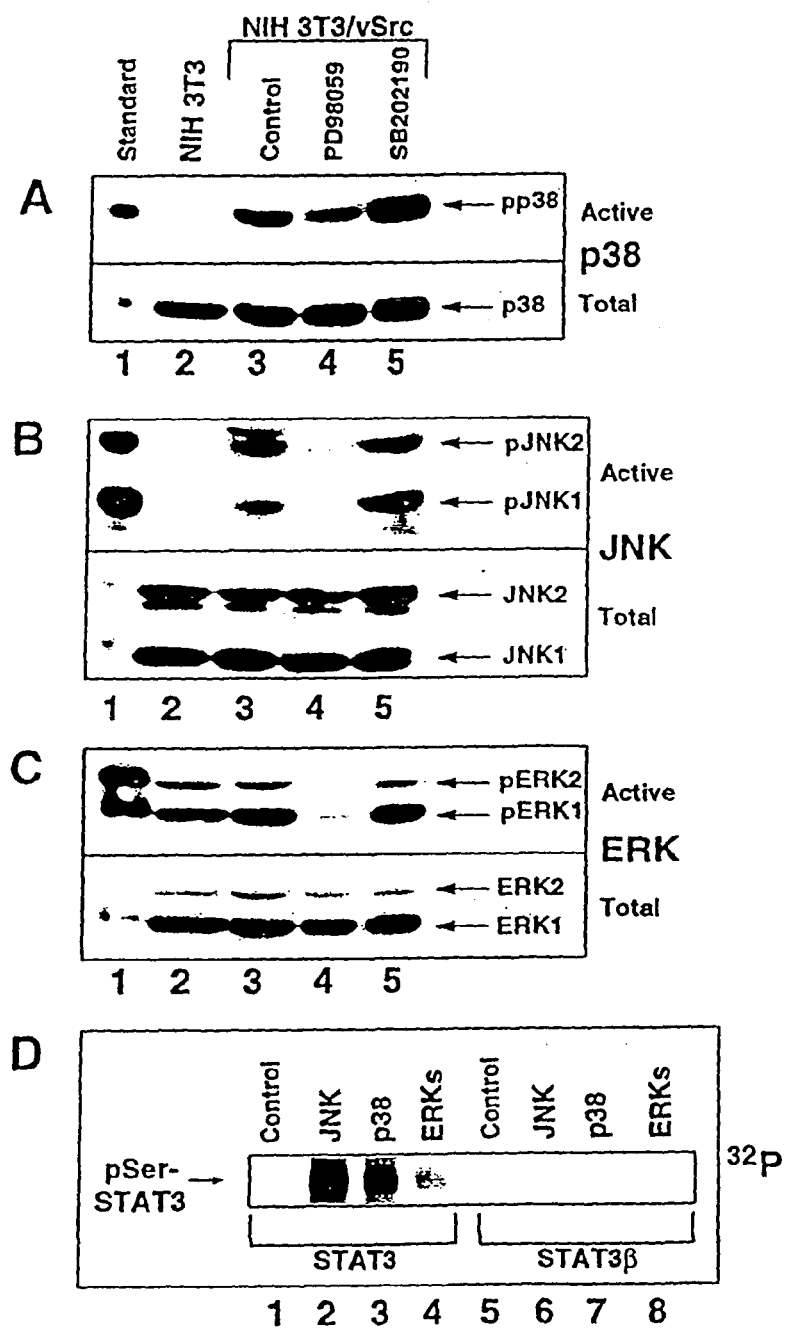

FIG. 13. p38 and JNK are constitutively-induced in Src-transformed cells and phosphorylate STAT3 in vitro. (A) Western blot analysis of whole-cell lysates prepared from normal (lane 2) NIH 3T3 fibroblasts or Src-transformed counterparts treated with or without PD98059 or SB202190 (lanes 3 to 5). Samples are probed with antibody specific to phospho-p38 (upper panel) or total p38 (lower panel). (B) Whole cell extracts described in (A) are analyzed by Western blotting. Samples are probed with antibody specific to phospho-JNK1/2 (upper panel) or total JNK1/2 (lower panel). (C) Whole-cell extracts described in (A) are analyzed by Western blotting. Samples are probed with antibody specific to phospho-ERK1/2 (upper panel) or total ERK1/2 (lower panel). (D) In vitro serine phosphorylation of STAT3 by JNK, p38 and ERKs. Purified baculovirus-expressed STAT3 (lanes 1 to 4) and STAT3b (lanes 5 to 8) are incubated with [g-$^{32}$P]ATP together with or without purified JNK, p38 or ERKS for 30 min, and subjected to SDS-PAGE and autoradiography. For positive identification, cell lysates from anisomycin-treated C6 glioma cells with highly induced EMS, p38 and JNK, serve as standards (lane 1).

Figure 14:
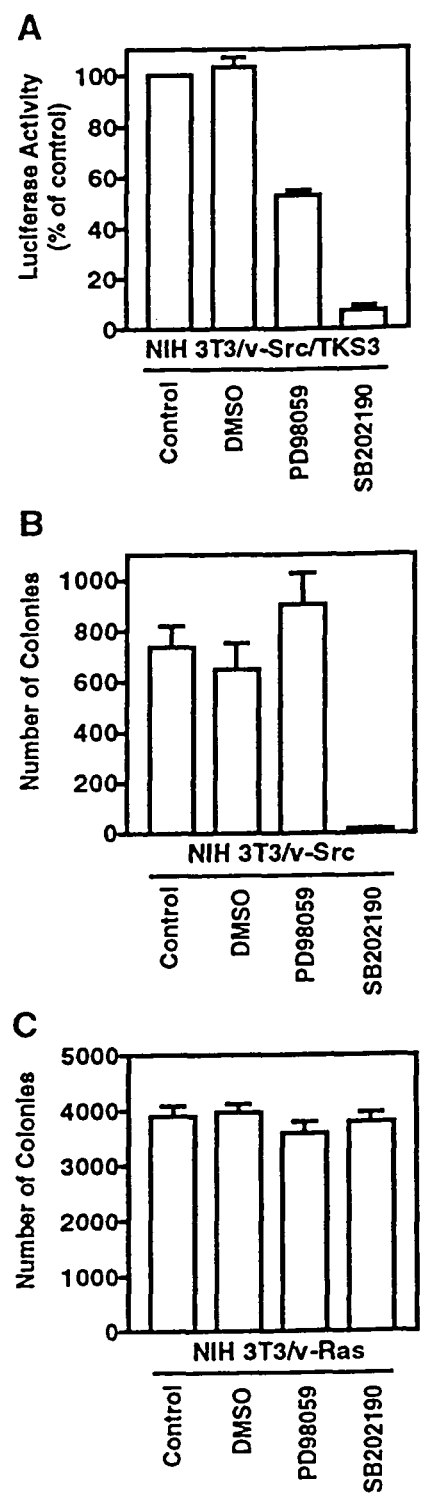

FIG. 14. Inhibition of p38 activity blocks cell transformation by v-Src and not by v-Ras. (A) NIH 3T3/v-Src/TKS3 cells stably transfected with the STAT3-dependent luciferase reporter, pLucTKS3, are treated with the indicated inhibitors for 6 hours prior to cytosolic extract preparation and luciferase assays. Values are the means plus standard deviations of 6 independent assays. (B) NIH 3T3/v-Src fibroblasts seeded in soft-agar suspension are treated once weekly with the indicated inhibitors until large colony formation is evident. Values are the means plus standard deviations of 12 independent assays. (C) NIH 3T3/v-Ras fibroblasts seeded in soft-agar suspension are treated once weekly with the indicated inhibitors and colonies counted as in (B) above. Values are the means plus standard deviations of 9 independent assays.

Figure 15:
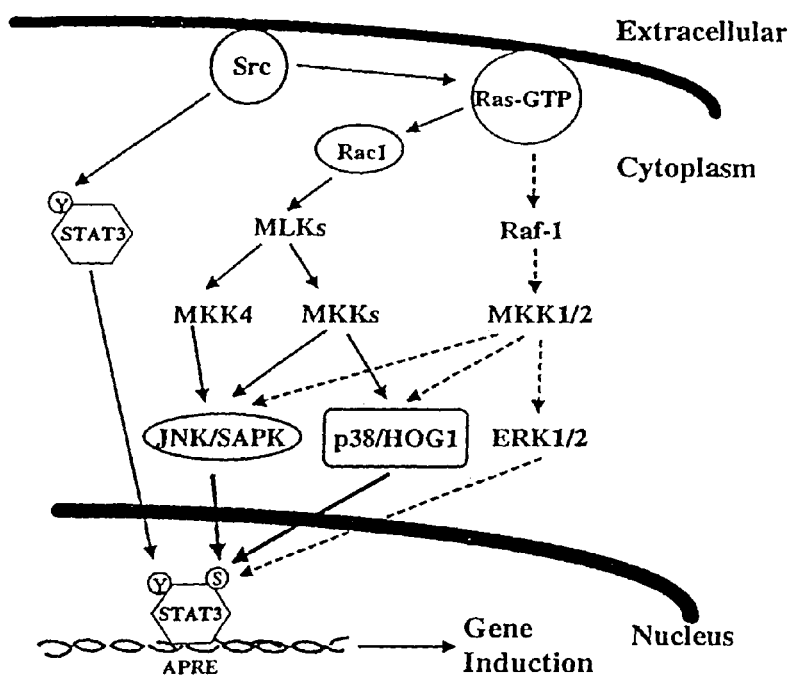

FIG. 15. Model of STAT3 phosphorylation by tyrosine and serine/threonine kinase signaling pathways in Src oncogenesis.

Figure 16:
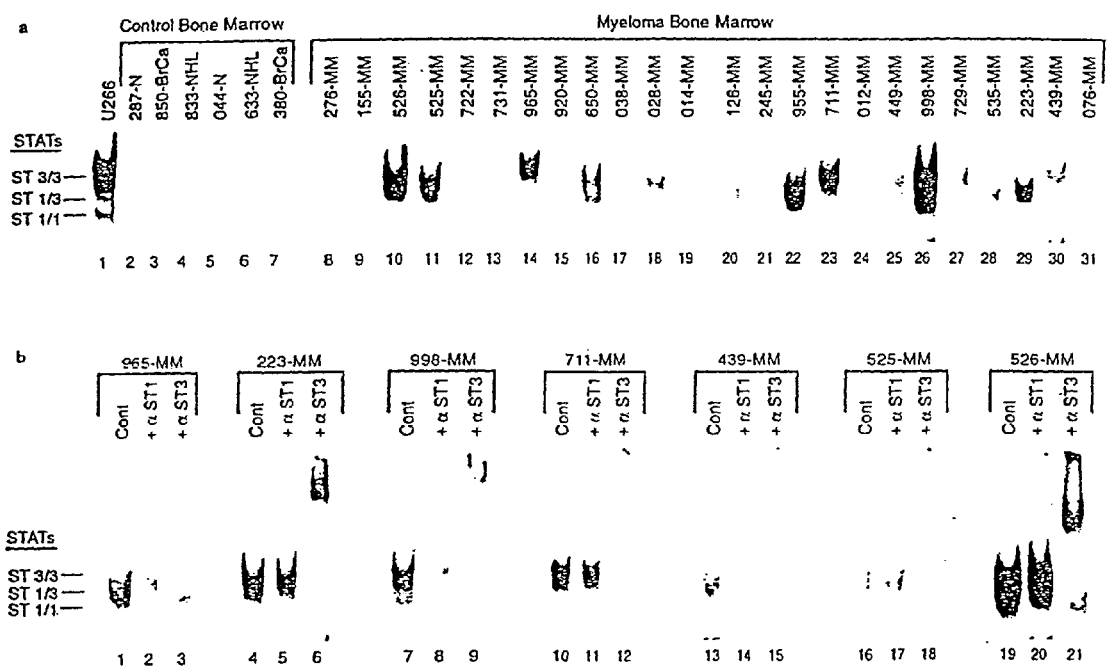

FIG. 16. Activation of STAT proteins in bone marrow cells of patients with multiple myeloma. (a) Nuclear extracts prepared from bone marrow cells are incubated with the $^{32}$P-labeled SIE oligonucleotide probe and analyzed by EMSA. The mononuclear fraction is isolated from bone marrow aspirates from normal marrow donors (N), patients with no evidence of bone metastases (Non-Hodgkin's lymphoma, NHL, or breast cancer, BrCa), and patients with multiple myeloma. (b) Identification of specific STAT proteins activated in multiple myeloma specimens. Untreated control extracts (lanes 1,4,7,10,13,16,19), extracts pre-incubated with anti-Stat1 (lanes 2,5,8,11,14,17,20), or anti-Stat3 (lanes 3,6,9,12,15,18, 21) antibodies. Positions of STAT3 homodimers (ST3/3), STAT1:Stat3 heterodimers (ST1/3), and STAT1 homodimers (ST1/1) are indicated.

Figure 17:
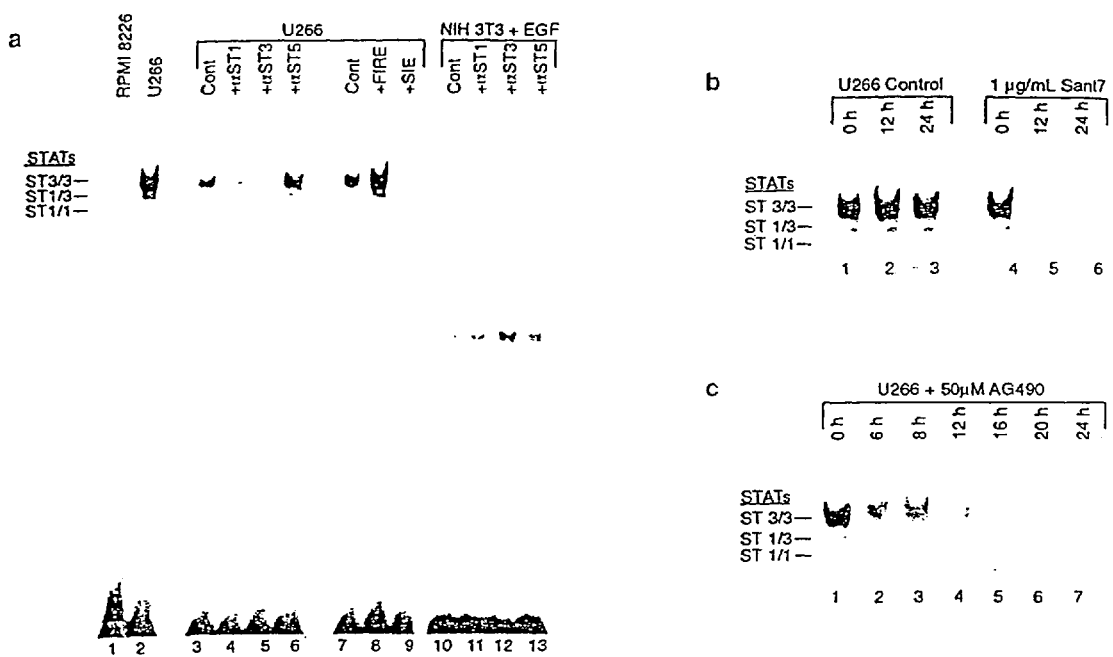

FIG. 17. Elevated STAT DNA-binding activity in human myeloma cells depends on signaling by IL-6 receptor and JAK family kinases. (a) Nuclear extracts prepared from U266 or RPMI 8226 cells are incubated with the $^{32}$P-labeled SIE oligonucleotide probe and analyzed by EMSA. NIH 3T3 cells are stimulated with EGF as a reference for the identification of STAT proteins. Untreated extracts (lanes 1,2,3,7,10); extracts pre-incubated with anti-Stat1 (lanes 4,11), anti-Stat3 (lane 5,12), or anti-Stat5 (lane 6,13) antibodies to identify activated STATs; extracts pre-incubated with excess unlabeled FIRE as an irrelevant oligonucleotide (lane 8) or unlabeled SIE oligonucleotide (lane 9) as specific competitor. (b) U266 cells are either untreated (lanes 1-3) or treated with 1 mg/ml Sant7 (lanes 4-6) and nuclear extracts are prepared at the times indicated. (c) Cells are treated with 50 mM AG490 for the times indicated prior to preparation of nuclear extracts.

Figure 18:
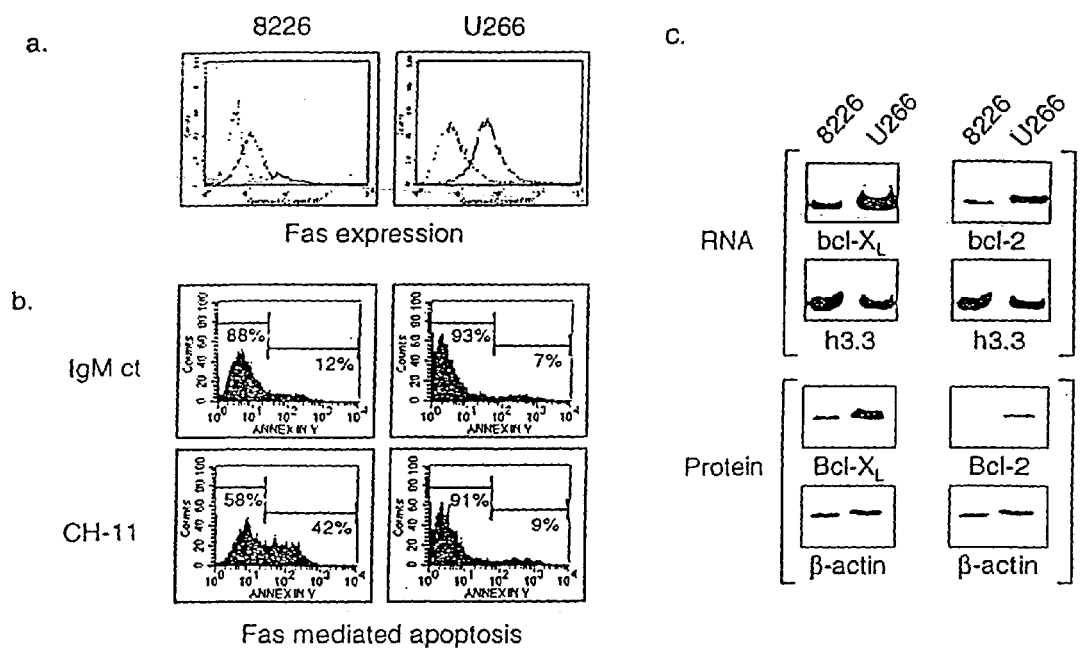

FIG. 18. U266 myeloma tumor cells express Fas receptors but are resistant to Fas-mediated apoptosis. (a) Surface expression of Fas (CD95) is measured by staining with the non-apoptosis inducing antibody UB2 (solid line) or IgG, isotype control (dotted line) and FITC-conjugated secondary mAb. (b) Fas-mediated apoptosis is measured by incubation of the cells with IgM control serum (upper panels) or 500 ng/ml of the Fas agonist antibody CH-11 (lower panels) for 18 hours prior to staining with Amexin V-FITC and analysis by flow cytometry. Treatment with 100 ng/ml Fas ligand gives identical results. Histograms shown are representative of 5 independent experiments. (c) Constitutive expression of Bcl-2 and Bcl-x$_L$, in 8226 and U266 human myeloma cells. Total RNA is extracted and analyzed by RT-PCR. Histone 3.3 serves as a control for quantification and RNA integrity. Radiolabelled products are separated on a 3% acrylamide gel and visualized by phosphorimager. Bcl-x$_L$, (left column) and Bcl-2 (right column) protein expression is examined by Western blot analysis with ECL detection.

Figure 19:
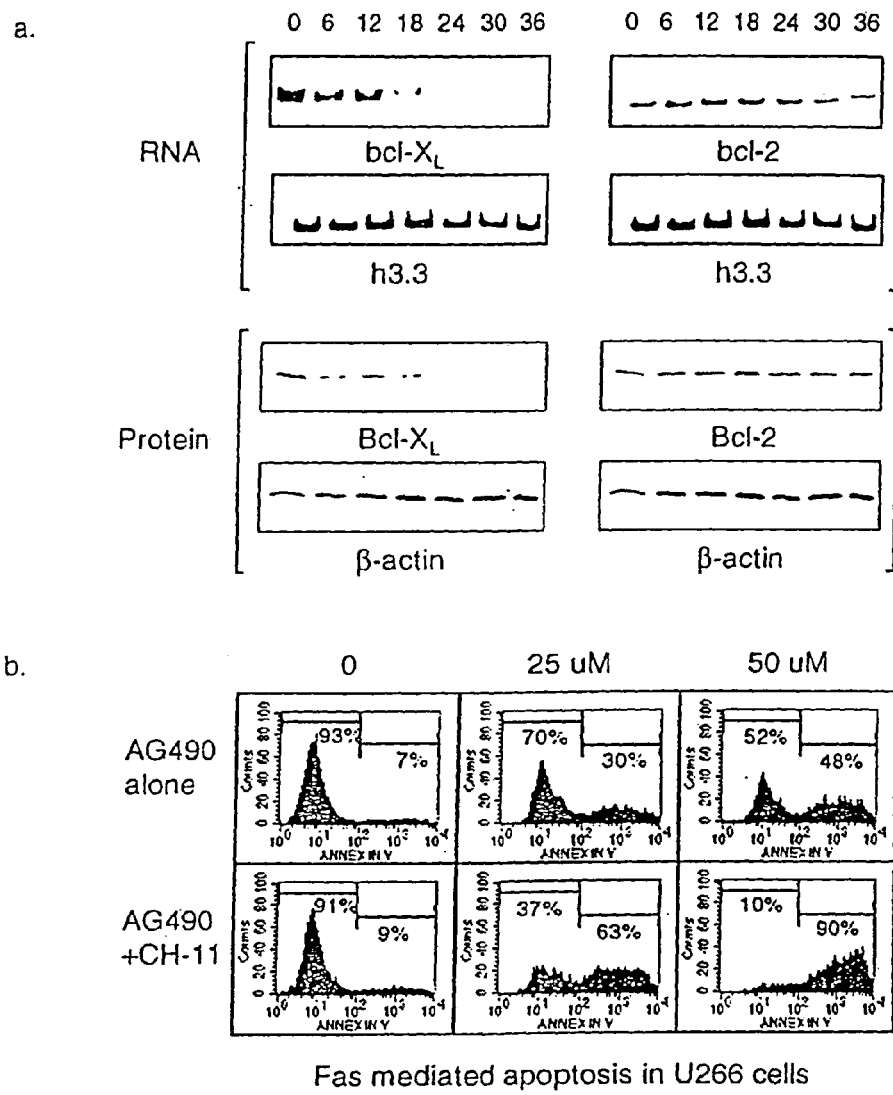

FIG. 19. AG490 inhibits Bcl-x$_L$, expression and sensitizes U266 cells to Fas-mediated apoptosis. (a) U266 cells are treated with 50 mM AG490 for the indicated time and analyzed for expression of Bcl-x$_L$, (left column) and Bcl-2 (right column) mRNA and protein. To control for potential variation related to time, untreated controls are collected at all time points, and identically analyzed. Data shown are representative of three independent experiments. (b) Fas-mediated apoptosis in AG490 treated cells. U266 are treated with the indicated concentration of AG490 for 24 hours prior to the addition of the agonistic anti-Fas antibody, CH-11. Following an additional 12 hours of incubation, cells are stained with Annexin V-FITC and analyzed for apoptosis by flow cytometry. Marker positioning is based on fluorescence of control treatments, and data shown are representative of 7 independent experiments in which Fas-specific apoptosis ranged from 18-41%.

Figure 20:
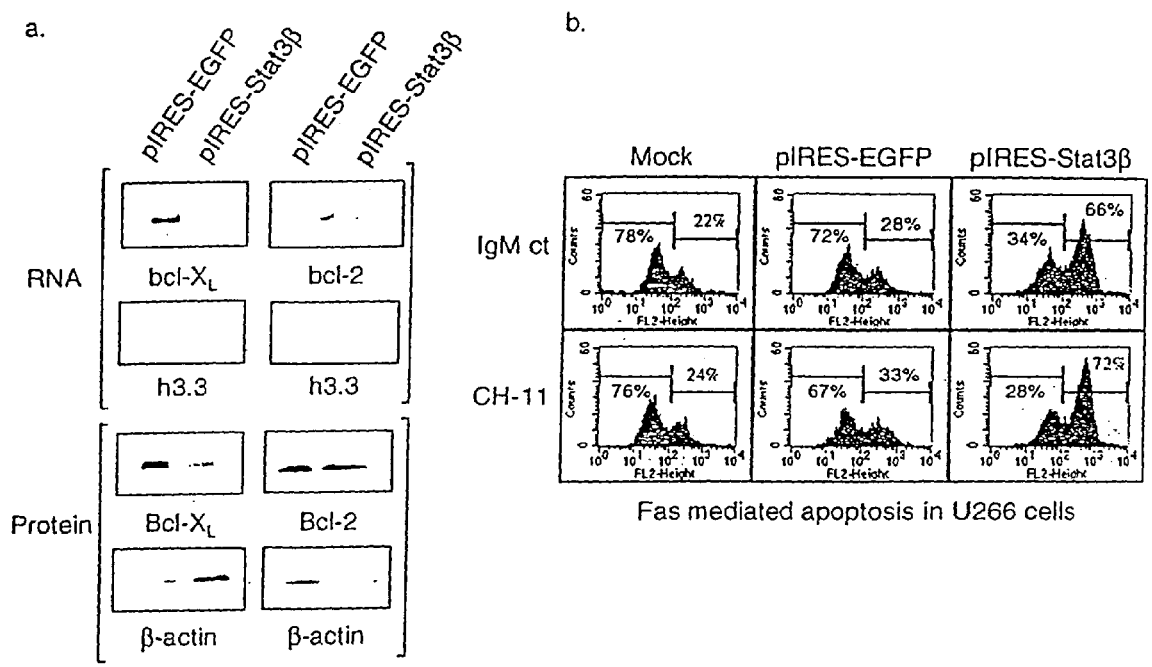

FIG. 20. Dominant-negative STAT3b protein inhibits Bcl-x$_L$, expression and enhances programmed cell death. (a) U266 cells transfected with pIRES-Stat3b or pIRES-EGFP are sorted on the basis of EGFP expression, and then analyzed for bcl-x or bcl-2 mRNA and Bcl-x$_L$, or Bcl-2 protein expression. (b) U266 cells are transfected with PIRES-EGFP or pIRES-Stat3b 48 hours prior to treatment with IgM control serum (upper panels) or 500 ng/ml CH-11 antibody (lower panels). At 72 hours post-transfection, apoptotic cells are stained with Annexin V-PE and analyzed by flow cytometry with live gating on EGFP-expressing cells. Marker positioning is based on fluorescence of control treatments. Treatment with 100 ng/ml Fas ligand gives identical results. The data shown are representative of 5 independent experiments.

Figure 21:
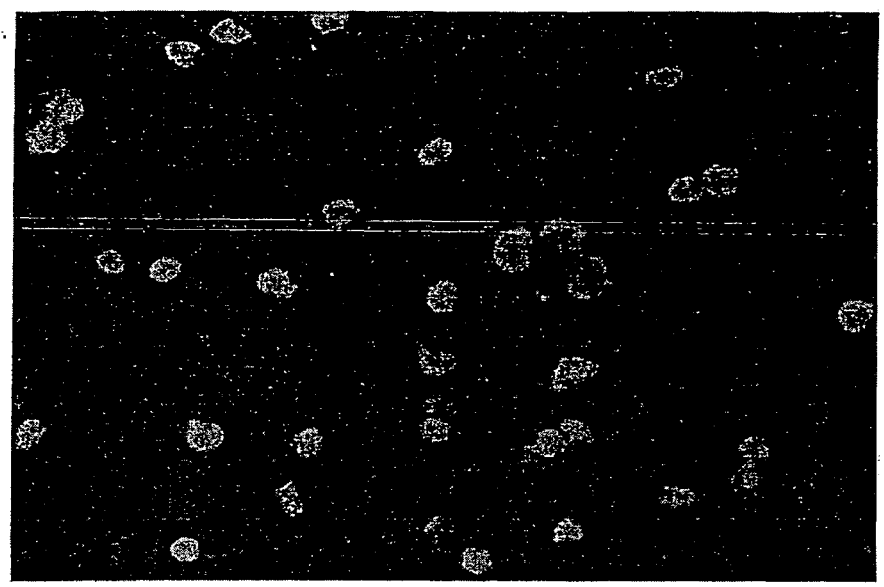
Figure 21:
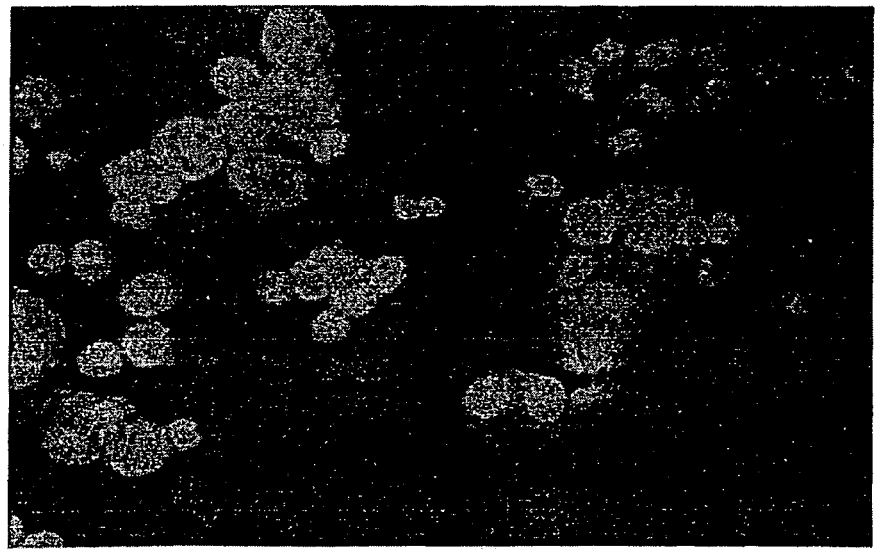

FIG. 21. STAT3b-expressing myeloma cells exhibit characteristic apoptotic morphology. U266 cells are transfected with (a) pIRES-Stat3b or (b) pIRES-EGFP and sorted by FACS on the basis of EGFP expression. After sorting, cells are recovered in complete media and applied to slides by cytospin, followed by methanol fixation for 20 min at 4° C. Cells are stained with DAPI and the slides examined by fluorescent microscopy.

Figure 22:
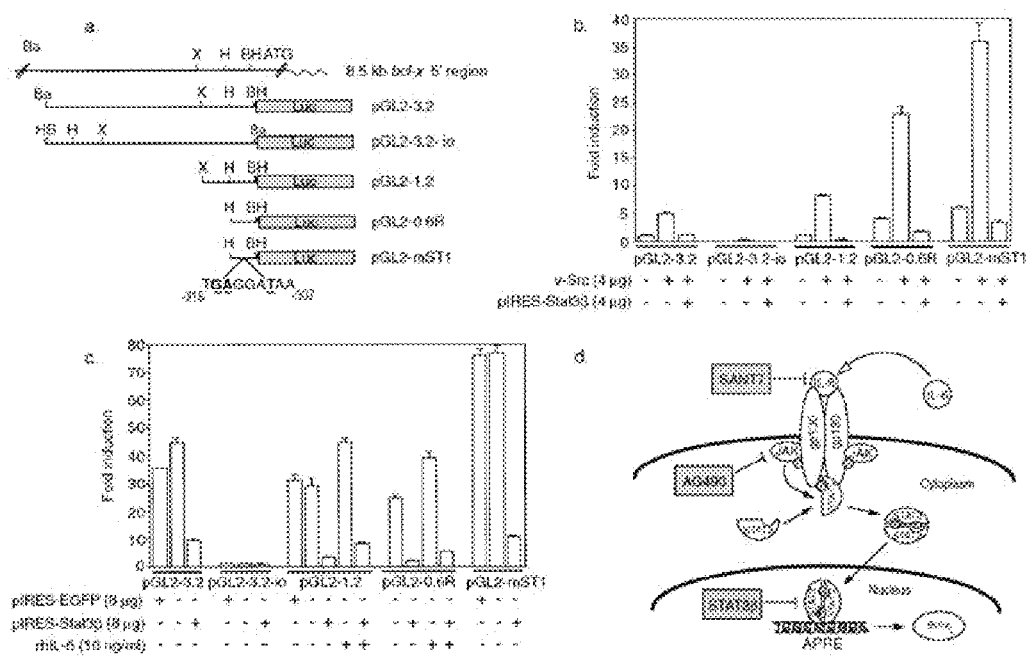

FIG. 22. STAT3-dependent transactivation of the bcl-x gene promoter. (a) Structures of bcl-x promoter constructs driving expression of the luciferase (Luc) reporter gene. The pGL2-3.2-io construct contains the bcl-x promoter sequences in the inverse orientation; the pGL-mST1 construct contains the mutated STAT1-binding site. (b) Reporter constructs are co-transfected into NIH 3T3 fibroblasts together with expression vectors encoding v-Src or STAT3b as indicated. The mean fold activation from three independent experiments, each performed in at least triplicates, is shown with standard error bars. (c) Reporter constructs are co-transfected into U266 myeloma cells with the indicated expression vectors. The pIRES-EGFP construct is the empty vector used to overexpress STAT3b, and rhIL-6 is recombinant human IL-6. Results represent the means plus standard deviations from three independent transfections, each performed in at least triplicate. (d) Model for IL-6 signaling through STAT3 to the bcl-x gene.

Figure 23:
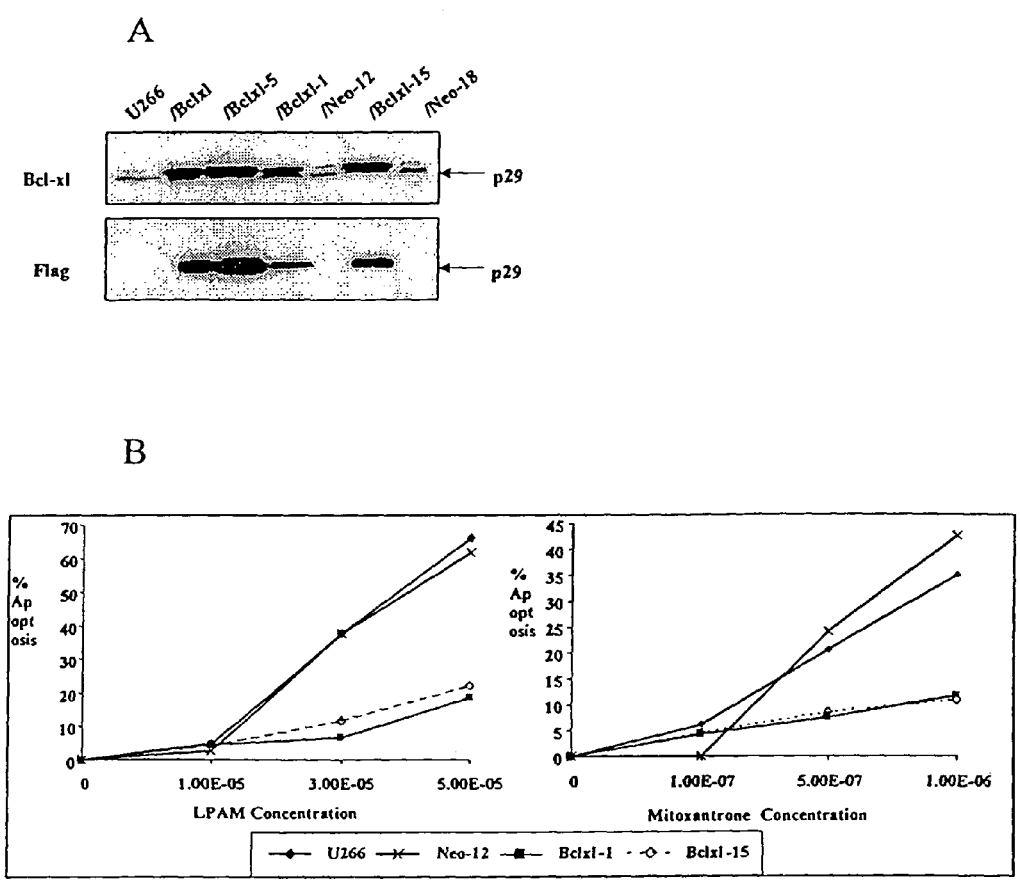

FIG. 23 Enforced Overexpression of Bcl-x Confers Resistance to Chemotherapy. Panel A: U266 cells are transfected with a CMV expression vector encoding Bcl-x, tagged with the FLAG epitope. Several stable, independent clones overexpressing Bcl-xL, as well as empty vector controls (Neo), are isolated and analyzed by Western blot with antibodies to Bcl-$x_L$, or the FLAG epitope tag. B: The indicated cell lines are incubated with either melphalan (LPAM) or mitoxantrone for 24 h, and apoptosis is monitored by AnnexinV-FITC staining and flow cytometry. Overexpression of Bcl-$x_L$ protects the cells from chemotherapy-induced apoptosis.

Figure 24:
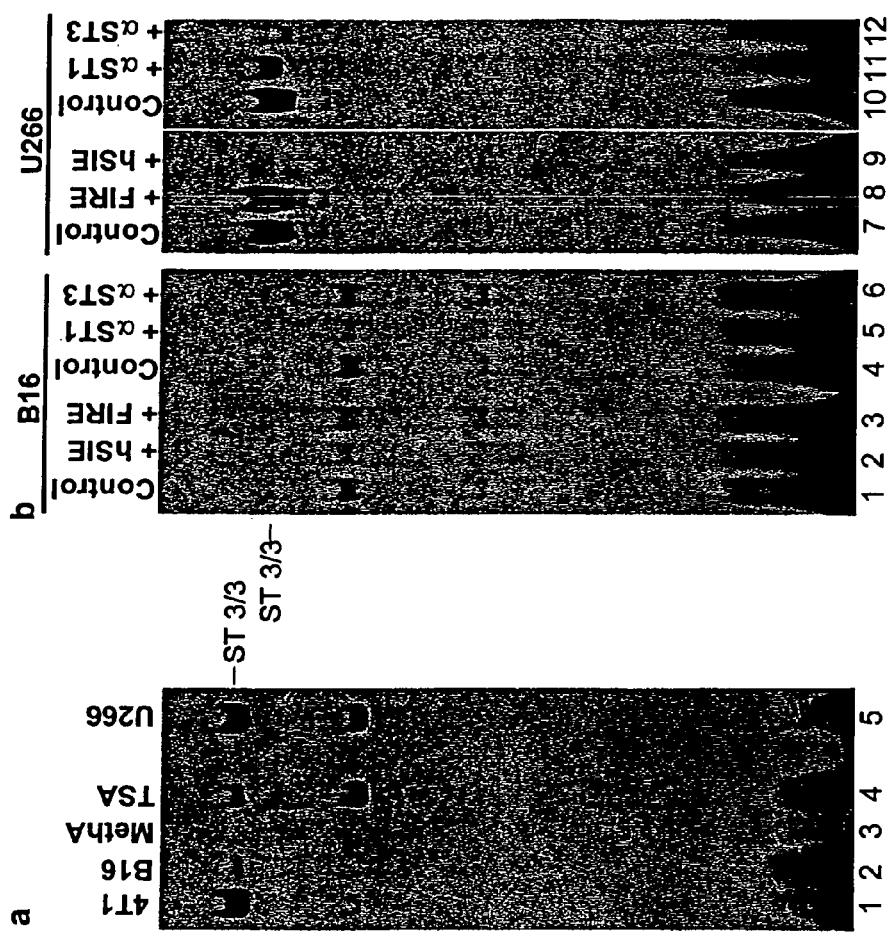

FIG. 24. STAT3 is activated in murine tumor cell lines. (a) Nuclear extracts prepared from the indicated mouse tumor cells and human U266 myeloma cells are incubated with the $^{32}$P-labeled hSIE oligonucleotide probe and analysed by EMSA. (b) Nuclear extracts from B16 cells are preincubated with excess unlabeled hSIE (lane 2) or FIRE (irrelevant oligonucleotide, lane 3) probes, and anti-Stat1 (lane 5) or anti-Stat3 (lane 6) antibodies to confirm specific STAT3 activation. Human myeloma U266 cells are used here as a positive control for STAT3 activation (17). ST3/3 indicates STAT3 homodimers.

Figure 25:
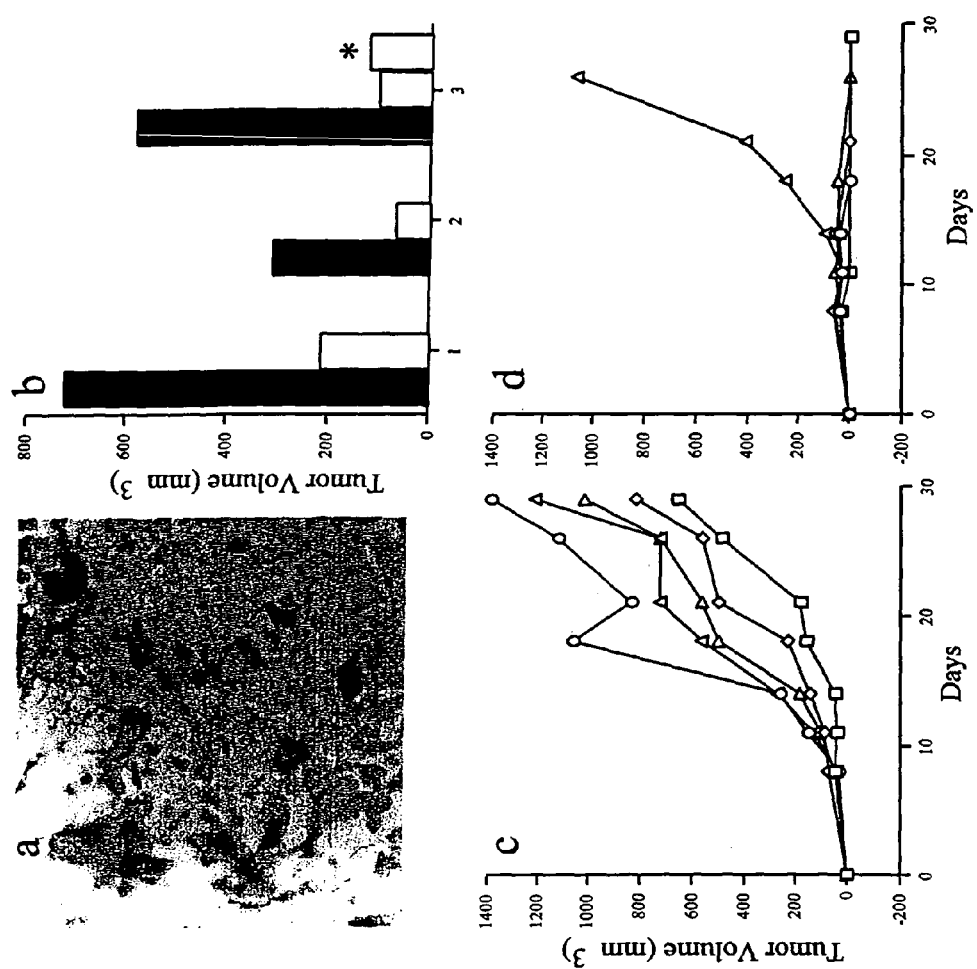

FIG. 25. Expression of STAT3b inhibits B16 tumor growth in vivo. (a) b-gal staining of tumor cells electroinjected with the b-gal plasmid. Overall, 15% of the tumor cells are b-gal positive. Little or no staining is observed in the negative control (pcDNA3 transfected tumor section receiving the same staining). (b) Summary of several independent STAT3b gene therapy experiments in vivo. Data shown represent average tumor volumes in 3 experiments on the day when one or more animals in each experiment was sacrificed due to oversized or ulcerated tumors (on days 28, 20, 22, respectively). A total of 15 control animals are treated with empty vector (n), and 20 mice are treated with STAT3b (o), either pIRES-Stat3b or pAdCMV-Stat3b (indicated by *). For one representative experiment, growth kinetics of B16 tumors treated with either pIRES-EGFP (c) or pIRES-Stat3b (d) are shown. The first gene electroinjection is performed on day 8, when tumors reached an average diameter of 3-6 multiple myeloma. Tumor measurements and the gene therapies indicated above are performed every 3 to 4 days. Four out of five pIRES-Stat3b treated tumors regress.

Figure 26:
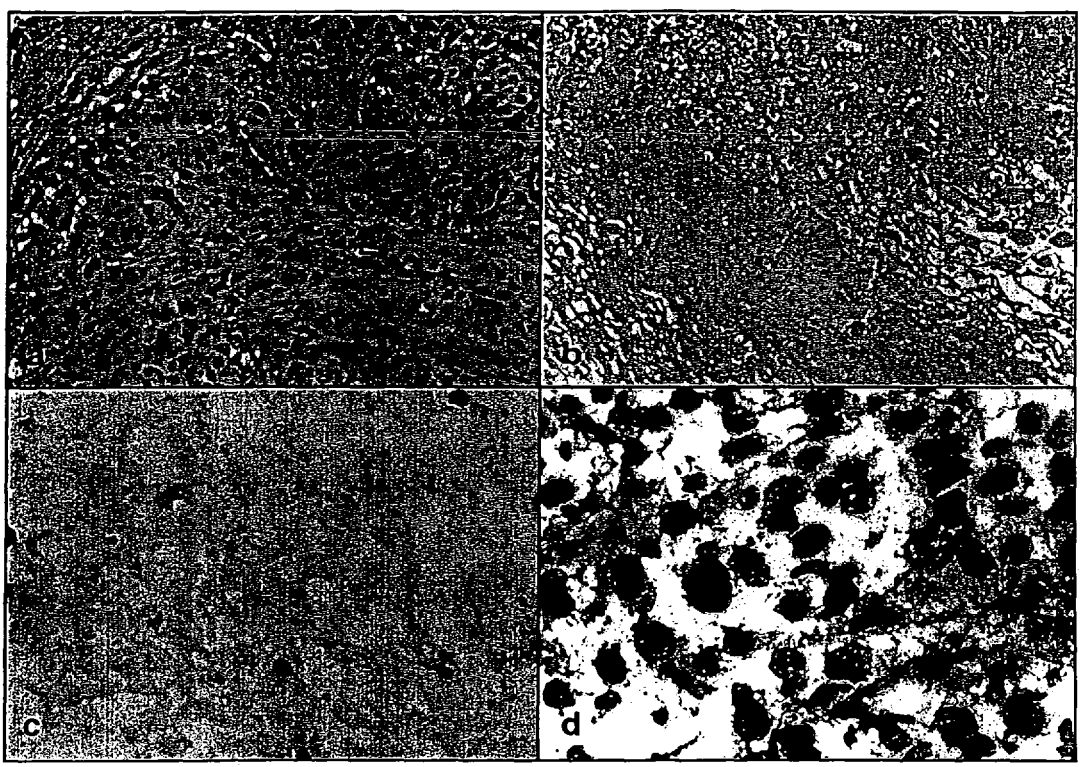

FIG. 26. Gene therapy with STAT3b induces apoptosis in B16 tumors in vivo. H&E staining of B16 tumors treated with either the empty vector (a) or the STAT3b vector (b). Tunel assay of the B16 tumors electroinjected with either the empty vector (c) or the STAT3b vector (d).

Figure 27:
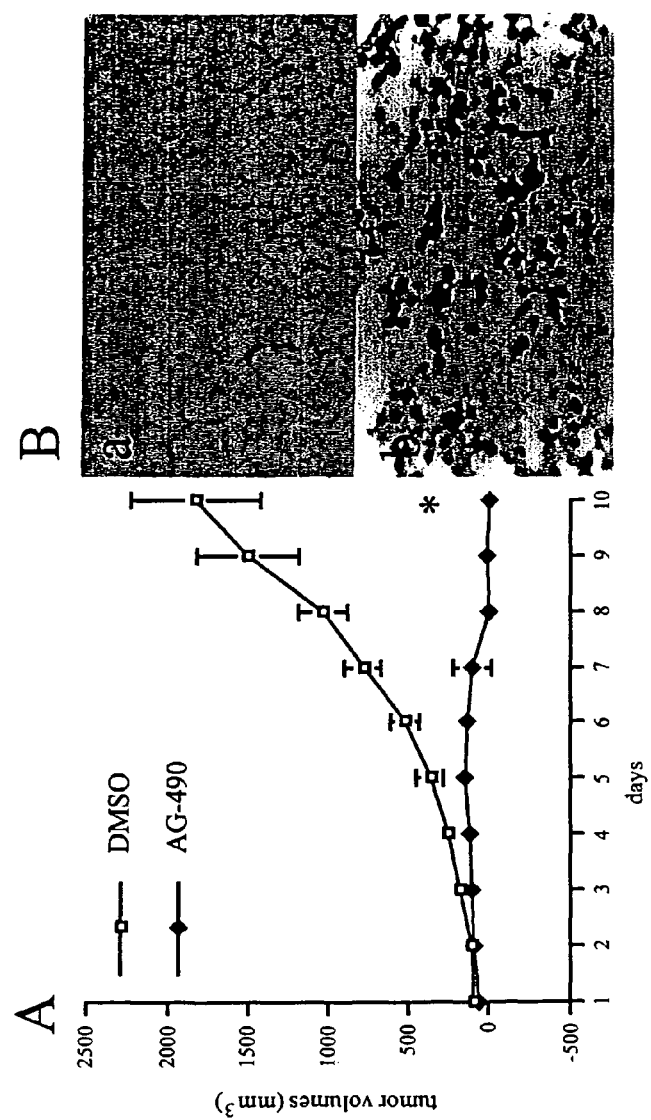

FIG. 27. Administration of AG-490 induces transient regression of MOPC myeloma tumors and apoptosis of MOPC cells in vivo. A. Results are expressed as the means of tumor volumes±SD. AG-490-treated mice, n=13; DMSO-treated mice, n=10. B. TUNEL assays of tissue sections prepared from MOPC tumors after treatment with either DMSO vehicle (a) or AG-490 (b).

Figure 28:
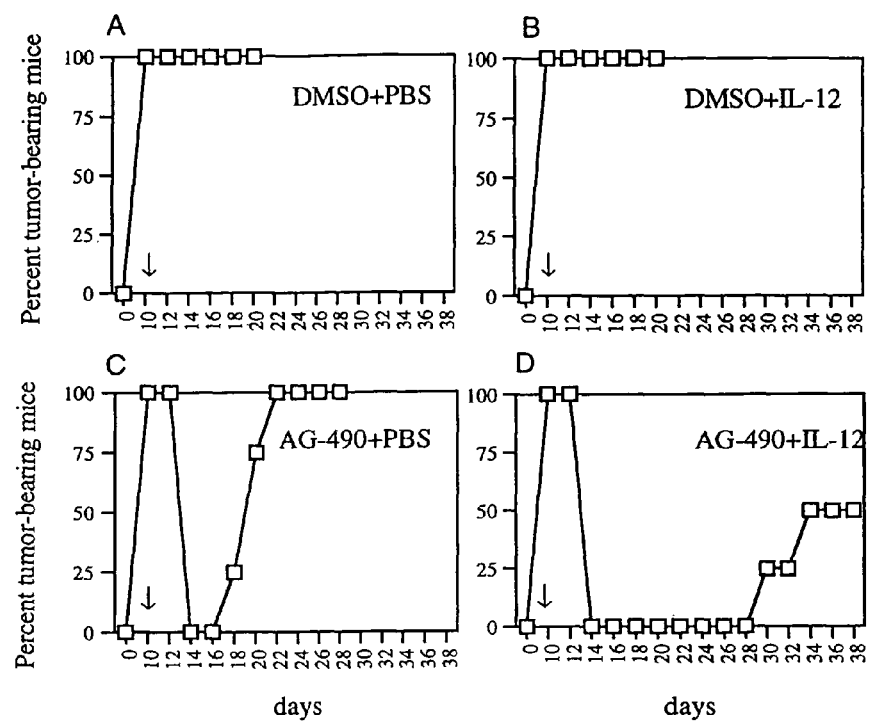

FIG. 28. Recombinant IL-12 prolongs the AG-490-mediated antitumor effect. A—B. MPC11 tumor-bearing mice received either PBS (A) or rIL-12(B)(200 ng every second day). For each treatment, n=5. C. MPC11 tumor-bearing mice are treated with AG-490 or DMSO vehicle alone for five days. On day 4, all of the tumors in AG-490-treated mice regressed. D. On day 5, AG-490 treated mice received s.c. administration of either rIL-12 (200 ng every second day) or PBS until day 15. Secondary tumor growth and metastasis (large lymph nodes or paralytic symptoms) are determined by palpation and visual observation. Mice with either secondary tumor growth or metastasis are scored as mice with tumor. AG-490 or DMSO alone, n=10; AG-490 plus IL-12, n=8. AG-490 treatment followed by 100 ng rIL-I2 treatment every second day is also performed with similar results.

Figure 29:
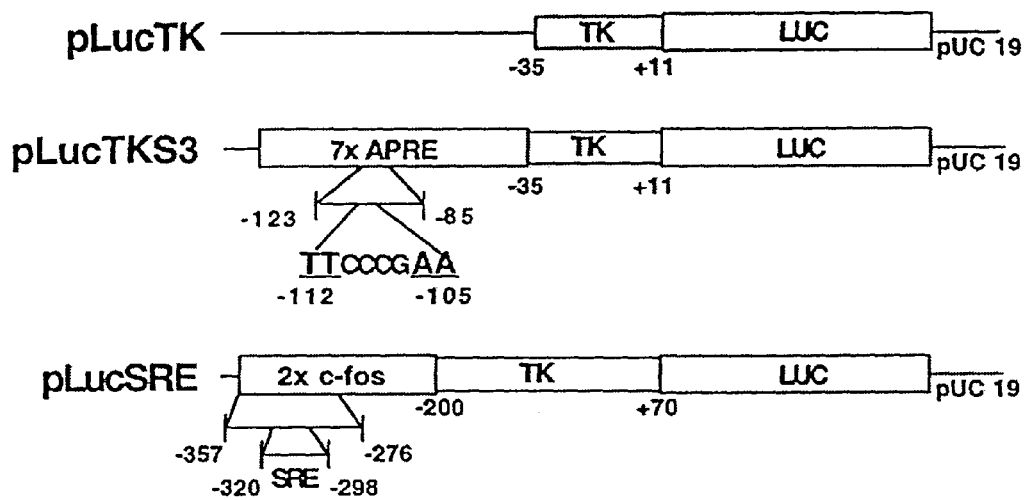

FIG. 29 Reporter Constructs for High Throughput Transcription Assays. The pLucTK reporter is a negative control containing only the TK minimal promoter. pLucTKS3 is a STAT3 reporter containing 7 copies of a STAT3-specific binding site (APRE) inserted upstream of the TK promoter. pLucSRE contains the c-fos SRE that is activated by the Ras-Raf pathway independently of STATs. Reporter activity is assayed as light emission using a 96-well plate luminometer.

Figure 30:
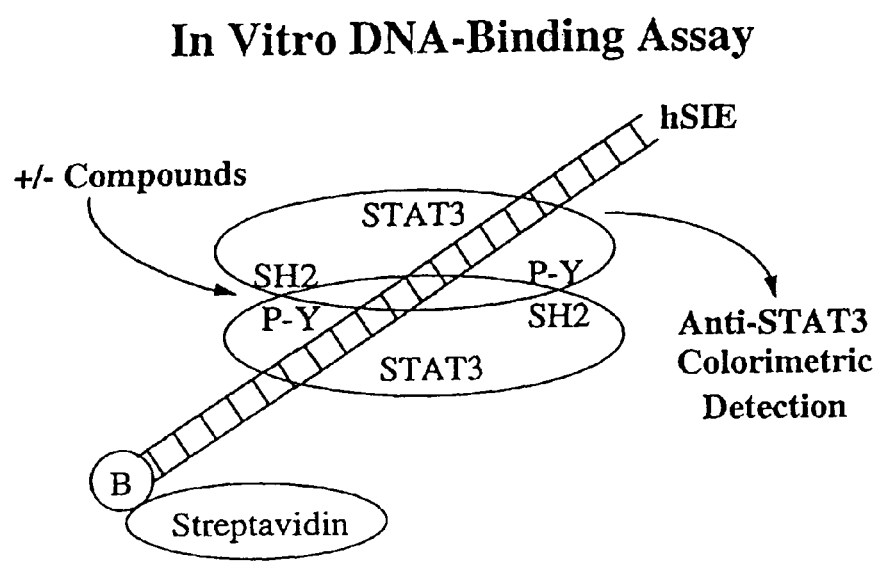

FIG. 30. High Throughput Assay for STAT3 DNA-binding Activity. The hSIE oligonucleotide is biotinylated and immobilized to streptavidin-coated 96-well plates. Activated STAT3 dimers produced by baculovirus-infected Sf9 cells are added together with or without test compounds. STAT3 DNA-binding to the hSIE probe is detected by anti-STAT3 antibodies coupled to a colorimetric detection system using an ELISA plate reader.

Figure 31:
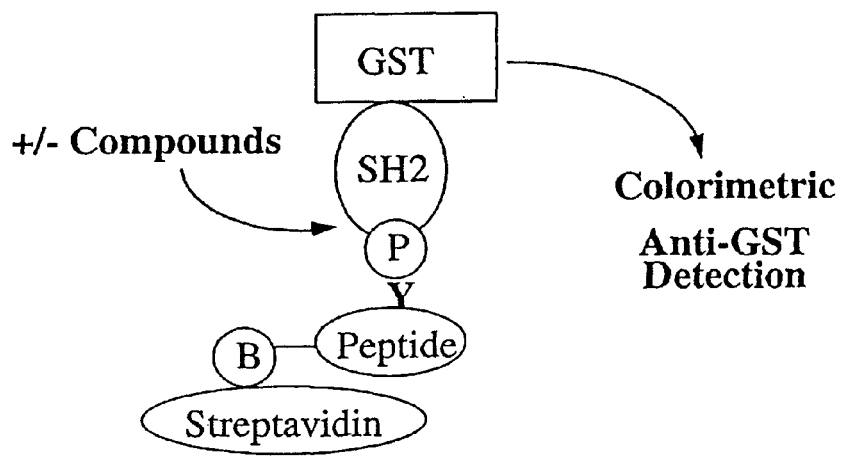

FIG. 31. High Throughput Assay for STAT3 SH2-phosphotyrosine Interactions. The biotinylated phosphopeptide containing the site of tyrosine phosphorylation in STAT3 is immobilized on streptavidin-coated 96-well plates. Bacterially expressed GST fusion protein containing the STAT3 SH2 domain that binds the phosphotyrosine is added together with or without test compounds. SH2-phosphotyrosine interactions are detected by anti-GST antibodies coupled to a colorimetric detection system using an ELISA plate reader.

5. DETAILED DESCRIPTION

In accordance with the present invention, conventional molecular biology, microbiology, and recombinant DNA techniques, well known to those of skill in the art to which the present invention pertains, may be employed. Such techniques are fully explained in the literature. See, e.g., Sambrook, Fritsch & Maniatis, "Molecular Cloning: A Laboratory Manual," Second Edition (1989), Cold Spring Harbor Laboratory Press, Cold Spring Harbor, N.Y.; Perbal, "A Practical Guide to Molecular Cloning," (1984); F. M. Asubel, et al., eds. "Current Protocols in Molecular Biology," John Wiley & Sons, Inc. (1994).

The following terms shall have the definitions set out below.

The term apoptosis is the cellular process, also known as programmed cell death, in which the cell undergoes a series of molecular events leading to some or all of the following morphological changes such as DNA fragmentation, chromatin condensation, nuclear envelope breakdown, and cell shrinkage.

The term Bcl-$x_L$, represents a member of the Bcl-2 (B-cell lymphoma) family of proteins involved in regulating a cell's response to apoptosis; Bcl-$x_L$, prevents programmed cell death. The term DNA consensus sequence herein represents a specific nucleotide motif found in the promoters of genes to which a transcription factor binds through interaction of the protein's DNA binding domain with the nucleotide sequence.

The term dominant-negative protein broadly indicates a protein which has been genetically altered so that when expressed in a cell it interferes with the function of the endogenous wild-type protein.

The term interleukin 6 (IL-6) represents a cytokine involved in regulating growth, survival and function of cells.

The term Janus kinase (JAK) represents a member of family of non-receptor tyrosine kinases that transfers a phosphate moiety to tyrosine on recipient proteins.

The term phosphotyrosine represents a modification of the tyrosine amino acid residue in which a phosphate group has been transferred to the hydroxyl group.

The term promoter represents a region of gene preceding the protein coding sequence that contains nucleotide sequence elements to which transcription factors bind and regulate gene expression.

The term protein tyrosine kinase (PTK) represents a signal transduction molecule that possesses an enzymatic function which transfers phosphate moieties to tyrosine on recipient proteins and thereby modulates the activity of the target protein.

The term signal transducer and activator of transcription (STAT) represents a member of a family of proteins, which when activated by protein tyrosine kinases in the cytoplasm, migrate to the nucleus and activate gene transcription.

The term signal transduction represents the biochemical process involving transmission of extracellular stimuli, via cell surface receptors through a specific and sequential series of molecules, to genes in the nucleus resulting in specific cellular responses to the stimuli.

The term Src-homology 2 domain (SH2) represents a specific protein structural motif among signaling molecules that recognizes and binds to phosphotyrosine moieties, creating sites of protein-protein interaction.

The term Src tyrosine kinase (Src) represents a member of a closely related family of non-receptor tyrosine kinases that participate in signal transduction by phosphorylating downstream effectors; the src gene is the first viral oncogene and was identified in Rous sarcoma virus.

The term syngeneic mice represents mice derived from a genetically identical background.

The term transcriptional activation represents the induction of gene expression via the interaction of regulatory proteins with the promoter elements of target genes.

The present invention may be understood by reference to the following Examples, which are provided by way of exemplification and are not to be read as limiting.

Example 1

Constitutive Activation of STAT3 in Breast Carcinoma Cell Lines

In this first example, we show that STAT3 is selectively and constitutively activated in many breast carcinoma cell lines, but not three cell lines derived from normal breast tissue. This example shows that disruption of STAT3 signaling is a desirable aspect of the present invention in the prevention of the growth of cancer cells. STAT DNA-binding activity in human breast cancer cell lines is examined by electrophoretic mobility shift assays (EMSA) (Garcia et al., 1997, Cell Growth Diff. 8:1267-1276). In these experiments, EMSAs are performed using the $^{32}$P-labeled sis-inducible element (SIE) as a probe to detect STAT DNA-binding activity in nuclear extracts of cells. This synthetic DNA oligonucleotide probe is a high-affinity mutant of the c-fos SIE, called hSIE, that binds both STAT1 and STAT3 (Yu, et al., 1995, Science 269:81-83). Our analysis reveals that STAT3, but not STAT1, is strikingly activated in five of nine breast tumor cell lines examined. This activation is constitutive and occurs in the absence of exogenous EGF stimulation. By contrast, STAT3 activation is not detected in any of the three cell lines derived from normal breast tissue.

Example 2

STAT Activation in Primary Breast Tumor Specimens

The second example demonstrates that constitutive activation of STAT3 is further present in primary breast tumor specimens, and is not limited to cells grown in suspension. In the present invention, this example provides further evidence of the desirability of inhibiting STAT3 signaling to inhibit cancer cell growth. As shown, tumor specimens snap frozen within 15 minutes of surgical excision retain the original STAT activation profile present at the time of excision (FIG. 1A). Using this procedure, increased STAT3 DNA-binding activity is detected in 5 out of 6 primary (stage III) breast tumors examined compared to adjacent non-tumor tissue (FIGS. 1A and B). An immunohistochemical assay for STAT3 activation based on the use of antibodies to activated, tyrosine phosphorylated STAT3 (pY-Stat3) is developed. With this assay, high levels of activated, nuclear pY-Stat3 are detected in the tumor cells, but not in the surrounding non-tumor cells, in sections through stage III breast cancer specimens (FIG. 2B). Binding of the antibodies to pY-Stat3 is competed by the corresponding STAT3 phosphopeptide antigen, demonstrating the specificity of this assay (FIG. 2C). In normal ductal epithelium, STAT3 activation is restricted to the proliferative basal layer (FIG. 2A). These findings show that constitutive activation of STAT3 occurs frequently in human breast carcinoma.

Example 3

Constitutive Activation of STAT3 in Ovarian Cancer Cell Lines and Tumors

The third example further demonstrates that constitutive activation of STAT3 is present in ovarian cancer cells. In the present invention, this example provides additional evidence of the 5 desirability of inhibiting STAT3 signaling to inhibit cancer cell growth. EMSA analyses of ovarian tumor specimens from patients are performed. As shown in FIG. 3B, primary ovarian tumors have constitutively-elevated STAT3 DNA binding activity. Moreover, the model human ovarian cancer cell line, SKOV3, but not OV10, also exhibits constitutively elevated STAT3 activation (FIG. 3A). These findings indicate that constitutive STAT3 activation is not limited 10 to breast carcinoma but, rather, is a feature in common with other solid tumors.

Example 4

Stat3 is Constitutively Activated in Multiple Myeloma Tumor Specimens

In still a fourth example of constitutive STAT3 activation in human cancerous cells, STAT3 is shown to be activated in 22/22 multiple myeloma tumor specimens, compared to 6 control specimens. Our results show that all 22 patients examined with myeloma tumors in bone marrow have constitutive activation of STATs, as measured by EMSA, while none of the six control bone marrows has detectable STAT DNA-binding activity (Catlett-Falcone, et al., 1999, Immunity 10: 105-115). Furthermore, this EMSA for STAT3 DNA-binding activity is highly quantitative and reproducible in thee independent assays for the same set of patient specimens (FIG. 4).

Example 5

Constitutive Activation of STATs in Acute Myelogenous Leukemia

In a fifth example, activation of STAT3 is further shown to occur in blood malignancies. STAT activation in bone marrow tumor specimens from patients with acute myelogenous 25 leukemia (AML) is investigated. Results demonstrate a high frequency of STAT activation in these specimens (FIG. 5). These findings show that AML is yet another human tumor in which aberrant STAT activation may contribute to malignant progression and resistance to chemotherapy. In the present invention, this example provides additional evidence of the desirability of inhibiting STAT3 signaling in the treatment of blood malignancies.

Example 6

Tyrosine Kinases Involved in STAT3 Activation in Breast Carcinoma Cells

The sixth example shows that inhibition of specific tyrosine kinases that activate STAT3 both inhibit constitutive STAT3 activation in breast carcinoma cells, and inhibit growth of the cells. In relation to the present invention, this example further demonstrates the desirability of targeting STAT3 signaling in the treatment of human cancer. The involvement of these, and other, tyrosine kinases in STAT3 activation is tested using specific inhibitors of JAK family kinases, and the EGF receptor and Src family kinases. Results show that in the model human breast cancer cell line, MDA-MB-468, a specific inhibitor of EGF receptor kinase (PD158780) does not block the constitutive STAT3 activation in these cells (FIG. 6B). In contrast, the constitutive activation of STAT3 is effectively blocked by the Src (PD180970) and JAK (AG490) specific inhibitors in a dose-dependent manner, showing that these kinases are involved in the ligand-independent activation of STAT3. Moreover, this inhibition of STAT3 signaling is accompanied by inhibition of cell growth by the Src and JAK inhibitors, but not by the EGF receptor inhibitor (FIG. 6A). These results show a role for Src and JAK, mediated via the STAT3 signaling pathway, in growth regulation of breast carcinoma cells.

Example 7

Inhibition of STAT3 Signaling Reduces Tumorigenicity: AG490 Inhibits Growth of Human Breast Carcinoma Cells in Nude Mice Because AG490 is a potent inhibitor of STAT3 signaling in MDA-MB-468 cells, whether this JAK inhibitor inhibits tumorigenicity in a nude mouse xenograft model is examined. AG490 is administered by continuous infusion using subcutaneous mini-pumps supplemented with intraperitoneal injections. This administration inhibits the growth of these human breast my carcinoma cells (FIG. 7). Significantly, inhibition of STAT signaling to an extent that will block tumor growth is not detectably toxic in animals. Combined with the antitumor efficacy and induction of apoptosis in tumor cells, and the lack of toxicity of dominant-negative STAT3β overexpression in normal cells as described herein below, these findings show that tumor cells harboring constitutively-activated STAT3 have become more dependent on the STAT3 pathway than normal cells. Thus, this nude mouse model further demonstrates that, in the present invention, the enhanced dependence of tumor cells upon constitutive STAT3 expression renders such cells amenable to growth inhibition by inhibition of the STAT3 pathway without significant toxic effects upon normal cells.

Example 8

Oncogenic Signaling Pathways Converge on STAT3: Requirement of Ras/Rac1-Mediated p38 and JNK Signaling for STAT3 Transcriptional Activity Induced by the Src Oncoprotein Abnormal activation of STAT3 is associated with oncogenesis. In an embodiment of the present invention, it is shown that inhibition of STAT3 signaling inhibits oncogenesis because two important oncogenic signaling pathways converge at the point of STAT3 activation. In fibroblasts expressing the Src oncoprotein, activation of STAT3 induces specific gene expression and is required for cell transformation. Although the Src tyrosine kinase induces constitutive STAT3 phosphorylation on tyrosine, activation of STAT3-mediated gene regulation requires both tyrosine and serine phosphorylation of STAT3. Here we delineate the signaling pathways underlying constitutive STAT3 activation in Src oncogenesis. We demonstrate that expression of Ras or Rac1 dominant-negative protein blocks STAT3-mediated gene regulation induced by Src in a manner consistent with dependence on p38 and c-Jun N-terminal kinase (JNK). Both of these serine/threonine kinases and STAT3 serine phosphorylation are constitutively induced in Src-transformed fibroblasts. Furthermore, inhibition of p38 and JNK activities suppresses constitutive STAT3 serine phosphorylation and STAT3-mediated gene regulation. In vitro kinase assays using purified full-length STAT3 as substrate show that both JNK and p38 can phosphorylate STAT3 on serine. Moreover, inhibition of p38 activity and thus STAT3 serine phosphorylation results in suppression of transformation by v-Src but not v-Ras, consistent with a requirement for STAT3 serine phosphorylation in Src transformation. This example demonstrates that Ras and Rac1-mediated p38 and JNK signals are required for STAT3 transcriptional activity induced by the Src oncoprotein. These findings delineate a network of tyrosine and serine/threonine kinase signaling pathways that converge on STAT3. Thus STAT3 is, in the present invention, a novel and appropriate therapeutic target in the prevention of oncogenesis and neoplastic transformation.

Materials and Methods

Plasmids.

The STAT3 reporter, pLucTKS3, myc-p38$^{mapk}$, myc-p46$^{sapk}$, dominant-negative DLK (K185A), dominant-negative MKK4 (dnMKK4), N17-Ras, and NT-Raf have all been previously described (Fan, et al., 1996, J. Biol. Chem. 271: 24788-24793, Pumiglia, et al., 1995 Mol. Cell. Biol. 15:398-406, Turkson, et al., 1998, Mol. Cell. Biol. 18:2545-2552). The pLucTKS3 reporter harbors seven copies of a sequence corresponding to the STAT3-specific binding site in the C-reactive protein gene's promoter (Turkson, et al., 1998, Mol. Cell. Biol. 18:2545-2552). The v-Src expression vector, pMvSrc, has been described (Johnson, et al., 1985, Mol. Cell. Biol. 5:1073-1083). Dominant-negative forms of ERK2, and MKK1 are as previously described (Her, et al., 1993, Biochem. J. 296:25-31, Whalen, et al., 1997, Mol. Cell. Biol. 17:1947-1958). The Rac1-I115 (activated) and Rac1-17N (dominant negative) vectors are generated by inserting Rac1 cDNA fragments from pZipNeo (Khosravi-Far, et al., 1995, Mol. Cell. Biol. 15:6443-6453) into pcDNA3 (Invitrogen) at a Bam H1 site.

Cell Culture and Transfections.

NIH 3T3, NIH 3T3/v-Src and NIH 3T3/v-Ras fibroblasts are grown in Dulbecco's modified Eagle's medium (DMEM) containing 5% iron-supplemented bovine calf serum (BCS). Transient transfections are carried out by the standard calcium phosphate method as previously described (Turkson, et al., 1998, Mol. Cell. Biol. 18:2545-2552). NIH 3T3 fibroblasts are seeded at 5×10$^5$ cells/100-mm plate in DMEM plus 5% BCS at 18 to 24 hours prior to transfection. Total DNA for transfections is typically 20 µg per plate, including 4 µg of luciferase reporter construct (pLucTKS3), 0.2 µg of β-galactosidase (β-Gal) internal control vector, and the amounts of expression vector indicated in figure legends. Transfection is terminated 15 hours later by aspirating the medium, washing the cells with phosphate-buffered saline (PBS), and adding fresh DMEM. For generation of NIH 3T3/v-Src/TKS3 cell lines stably expressing the STAT3 reporter, NIH 3T3/v-Src cells are transfected using Fugene 6 (Boehringer Mannheim) according to the supplier's protocol. The transfection mixture contains 5.5 µg total DNA per 10 cm plate, including 5 pg of the STAT3 reporter, pLucTKS3, and 0.5 µg of pcDNA3 that carries the neomycin resistance gene. Individual G418-resistant clones are picked and characterized with regard to STAT3-dependent luciferase activities.

Preparation of Cytosolic and Nuclear Extracts.

In the case of stable NIH 3T3/v-Src/TKS3 clones, cells are treated with inhibitors or DMSO for 6 hours prior to preparing cytosolic extracts. For transient expression assays, cytosolic extracts are prepared from cells at 48 hours posttransfection as previously described (Turkson, et al., 1998, Mol. Cell. Biol. 18:2545-2552). Briefly, after two washes with PBS and equilibration for 5 min with 0.5 ml of PBS-0.5 mM EDTA, cells are scraped off the dishes and the cell pellet is obtained by centrifugation (4,500×g, 2 min, 4° C.). Cells are resuspended in 0.4 ml of low-salt HEPES buffer (10 mM HEPES [pH 7.8], 10 mM KCl, 0.1 mM EGTA, 0.1 mM EDTA, 1 mM phenylmethylsulfonyl fluoride, and 1 mM dithiothreitol) for 15 min, lysed by the addition of 20 µl of 10% Nonidet P-40 (NP-40), and centrifuged (10,000×g, 30 s, 4° C.) to obtain the cytosolic supernatant, which is used for luciferase assays (Promega) measured with a luminometer and for β-Gal activity detection by colorimetric assay at $A_{570}$. As an internal control for transient transfection efficiency, results are normalized to β-Gal activity. For EMSA, nuclear extracts are prepared from transiently-transfected NIH 3T3 cells and volumes containing equal amounts of total protein are incubated with $^{32}$P-labeled M67SIE oligonucleotide probe, as previously reported (Garcia, et al., 1997, Cell Growth Differ. 8:1267-1276, Yu, et al., 1995, Science 269:81-83). Supershift assays are performed using rabbit polyclonal antibodies specific for C-terminal amino acid residues of STAT3 (750 to 769) or STAT1 (688 to 710) proteins (Santa Cruz Biotechnology).

Soft-Agar Colony Formation Assay.

Colony formation assays are carried out in 6-well dishes. Each well contains 1.5 ml of 1% agarose in DMEM as the bottom layer. The top layer in each well consists of 1.5 ml of 0.5% agarose in DMEM containing 4,000 or 6,000 of NIH 3T3/v-Src or NIH 3T3/v-Ras fibroblasts, respectively. Treatment with inhibitors is initiated one day after seeding cells by adding 75-100 µl of medium with or without inhibitors and repeated once a week until formation of large colonies is evident. For quantitation, colonies are stained by adding 20 µl of 1 mg/ml iodonitrotetrazoliurn violet to each well and incubating at 37° C. overnight. Stained colonies are counted the next day.

Western Blot Analysis.

Whole-cell lysates are prepared in boiling sodium dodecyl sulfate (SDS) sample-loading buffer in order to extract total proteins from the cytoplasm and nucleus as well as preserve the in vivo phosphorylation STATes. Equivalent amounts of total cellular protein are electrophoresed on an SDS-10% polyacrylamide gel and transferred to nitrocellulose membranes. Probing of nitrocellulose membranes with primary antibodies and detection of horseradish peroxidase-conjugated secondary antibodies by enhanced chemiluminescence (Amersham) are performed as previously described (Garcia, et al., 1997, Cell Growth Differ. 8:1267-1276, Turkson, et al., 1998, Mol. Cell. Biol. 18:2545-2552, Yu, et al., 1995, Science 269:81-83). Probes used are rabbit polyclonal antibodies against N-terminal amino acid residues (626-640) of STAT3 (Santa Cruz Biotechnology), phosphoserine-727 of STAT3 (25), active (phospho-) JNK, p38$^{mapk}$ or ERKs (New England Biolabs), or total JNK, p38$^{mapk}$ or ERKs (Santa Cruz Biotechnology).

Purification and Phosphorylation of STAT3 and Recombinant STAT3 Proteins.

STAT3 and STAT3β are purified from baculovirus-infected Sf-9 insect cells with biotinylated M67SIE oligonucleotides. Briefly, Sf-9 cells are infected with baculoviruses encoding STAT3 or STAT3β. 48 hours postinfection, cells are lysed with NP-40 lysis buffer (50 mM HEPES, pH 7.9, 150 mM NaCl, 1% NP-40, 20 mM NaF, 1 mM Na$_3$VO$_4$, 1 mM Na$_4$P$_2$O$_7$, 1 mM DTT, 0.5 mM PMSF, 2 mM EDTA, 0.1 µM aprotinin, 1 µM leupeptin, and 1 µM antipain), centrifuged (13,000×g, 15 s, 4° C.). The supernate cell lysates are supplemented with glycerol (to 10%) and 10 µg of poly(dI-dC):poly (dI-dC) in a final volume of 1 ml, and incubated at 4° C. for 30 min. Two micrograms of 5'-biotinylated DNA fragment, containing two copies of the M67SIE sequence (5'-AGCT-TCATTTCCCGTAAATCCCTA) (SEQ ID NO:1) (Wagner, et al., 1990, EMBO J. 9:4477-4484), are then added and further incubated at 4° C. for 2 hours with slow rotation. Subsequently, 100 µl of avidin-agarose beads (50% slurry) is added to the mix and incubated for 30 min. The beads are then collected by centrifugation, washed 4× with NP-40 lysis buffer, and 3× with kinase buffer (25 mM HEPES; pH 7.5, 10 mM magnesium acetate). After final centrifugation (3,000 rpm, 2 min), the pellets of STAT3 and STAT3β-bound Sepharose beads are incubated in 35 µl kinase buffer containing approximately similar activities of purified p38 (AG Scientific), JNK (BIOMOL) or ERKs (BIOMOL) protein kinases for 5 min at room temperature. Subsequently, 5 µl [g-$^{32}$P]ATP solution (50 µM ATP, 0.5 µCi/µl) is added and the mixture further incubated at 30° C. After 30 min, SDS-PAGE loading buffer was added, the samples are then electrophoresed on an SDS-8% polyacrylamide gel and exposed for autoradiography.

Results

Ras-Mediated Signaling is Required for STAT3 Transcriptional Activity.

Stat3 is constitutively activated in NIH 3T3 fibroblasts stably transformed by v-Src. In this example, we delineate the signaling pathways leading to the induction of STAT3 transcriptional activity using a STAT3-specific luciferase reporter (pLucTKS3) harboring the S'TAT3-binding site from the C-reactive protein gene's promoter (Turkson, et al., 1998, Mol. Cell. Biol. 18:2545-2552). The induction by v-Src of STAT3-specific luciferase reporter is completely abrogated by co-expression of the dominant-negative Ras mutant (N17-Ras) or an N-terminal fragment of Raf-1 (NT-Raf) designed to sequester Ras (Ceresa, et al., 1997, Endocrinol. 138:4131-4137, Pumiglia, et al., 1995, Mol. Cell. Biol. 15:398-406) (FIG. 8A). These findings show an obligatory requirement of Ras-mediated signaling for STAT3 transcriptional activity in NIH 3T3 fibroblasts expressing v-Src.

Which parts of the MKK-ERK pathway downstream from Ras are associated with induction of STAT3 transcriptional activity by Src are also shown. Results of luciferase reporter assays with the pharmacologic MKK1/2-selective inhibitor, PD98059 (Dudley, et al., 1995, Proc. Natl. Acad. Sci. USA 92:7686-7689), or dominant-negative MKK1 (dnMKK1) show that inhibition of MKK1/2 activity significantly suppresses transcriptional regulation by STAT3 (FIGS. 8B and C). However, expression of a dominant-negative form of ERK2, TAYF, has no inhibitory effect on STAT3 transcriptional activity (FIG. 8C), showing that ERK2 activity is not required for STAT3-mediated gene regulation induced by v-Src. We confirm the ERK2 dominant-negative activity of TAYF by inhibition of another luciferase_reporter, pLucSRE, which is not dependent on STAT3 but rather on the activation of the c-fos serum response element, SRE, by ERKs. Because both dnMKK1 and PD98059 block MKK signaling directly, these findings demonstrate a role for MKK-mediated signaling in STAT3 transcriptional activity. Together, our results show that a Ras-MKK-mediated signaling pathway interacts with STAT3 signaling.

STAT3 Transcriptional Activity Depends on Rac1-Mediated Signaling.

The Rac1 subfamily of small G proteins has a key role in signaling downstream from Ras, thus the contribution of Rac1-induced signals to STAT3 transcriptional activity is demonstrated. In luciferase reporter assays, the co-expression of dominant-negative Rac1 (N17 Rac1) or activated Rac1 (I115 Rac1) mutants significantly inhibits or enhances STAT3 transcriptional activity, respectively (FIG. 9A), showing Rac1 lies in the pathway leading from v-Src to STAT3 activation. To further show the contribution of Rac1-mediated signals to STAT3 signaling, the role of DLK, a member of the MLK family that participates in activation of the stress pathway by v-Src is demonstrated. Dominant-negative DLK (K185A) significantly inhibits the induction of STAT3-specific luciferase reporter activity (FIG. 9B). DLK interacts with complexes containing other MLK members (Whitmarsh, et al., 1998, Science 281:1671-1674), and dominant-negative DLK appears to interfere with the function of other members of the MLK family. Therefore, these findings implicate the entire MLK family but do not define which member is required in STAT3 signaling induced by v-Src. The co-expression of JNK1 (myc-p46$^{sapk}$) or p38 (myc-p38$^{mapk}$) proteins reverses this inhibitory effect in a concentration-dependent manner (FIGS. 9B and C). Therefore, the kinase activities of the overexpressed JNK1 or p38 proteins can sustain a level of serine phosphorylation sufficient for maximal STAT3 transcriptional activity even at marginal MLK activity. Together, these findings show that Rac1-mediated p38 and JNK activities contribute to STAT3 signaling induced by v-Src.

That p38 is central to STAT3 signaling is further corroborated by studies showing significant inhibition of STAT3-specific luciferase reporter induction in cells transiently expressing the STAT3-specific reporter and treated with SB202190, a pharmacologic inhibitor selective for p38 (FIG. 9D). Results show no inhibition of STAT3-specific luciferase reporter induction in fibroblasts transiently expressing v-Src and treated with this inhibitor (FIG. 9D), thus excluding a role for PI 3-kinase in transcriptional regulation by STAT3. Instead, induction of STAT3 transcriptional activity by v-Src requires Rac1-mediated p38 and JNK signals.

Evidence of Distinct JNK and p38 Pathways Involved in STAT3 Transcriptional Activity.

Reports in the literature delineate two distinct pathways leading to the activation of JNK and p38 (see Fanger, et al., Curr. Opin. Genet. Dev. 7:67-74, for a review). While both pathways utilize a common signal from Rac1, they emerge as separate signals at the level of MKKs. For example, MKK4 and MKK7 largely activate JNK, while MKK3 and MKK6 preferentially activate p38. To show how this divergence in signaling is relevant to STAT3 function, we first show the effect of dominant-negative MKK4 (dnMKK4) on transcriptional activation by STAT3. Expression of dnMKK4 significantly blocks STAT3-specific luciferase reporter induction (FIG. 10A), showing a requirement for MKK4 in the signaling leading to STAT3 transcriptional activity. The divergence in JNK and p38 signals is evident when only the co-expression of JNK1 (myc-p46$^{sapk}$), but not p38 (myc-p38$^{mapk}$), abrogates the inhibitory effect of dnMKK4 and restores STAT3 transcriptional activity (FIGS. 10A and B). These results establish that transcriptional activation by STAT3 utilizes the MKK4-JNK pathway, and confirm that distinct MKKs mediate the pathways leading to p38 and JNK activation. These results further demonstrate that STAT3-mediated gene regulation induced by v-Src requires Ras-Rac1-mediated activation of the stress pathway in a manner analogous to normal extracellular stimulus-induced activation of this pathway.

JNK and p38 Kinases Mediate the Key Role of Ras in STAT3 Transcriptional Activity.

Inhibition of Ras function (FIG. 8A) should block the activities of downstream MAPKs. Thus, the abrogation of STAT3 transcriptional activity following dominant-negative inhibition of Ras is due to lack of sufficient functional MAPKs. Overexpression of the MAPKs restores kinase activities and hence STAT3 function. Thus, co-expression of all three MAPK family proteins brings about recovery of STAT3 transcriptional activity that would otherwise have been blocked by dominant-negative inhibition of Ras (FIG. 11). As compelling evidence that p38, and to a lesser extent JNK, mediate the role of Ras in STAT3 transcriptional activity, co-expression of either of these MAPKs causes a complete or partial rescue of STAT3 function from inhibition by dominant-negative Ras (FIG. 11). The extent of this restoration is concentration-dependent on the level of p38 or JNK expression. The overexpressed p38 or JNK proteins compensate for the loss of kinase activities. Together, our findings demonstrate cooperation of Ras-mediated p38 and JNK pathways with v-Src for the induction of STAT3 transcriptional activity.

Serine Phosphrylation and DNA-Binding Activity of STAT3 in Fibroblasts Expressing v-Src.

In the context of transformation by v-Src, our results show a cross-communication of signals involving the p38 and JNK serine/threonine kinases and STAT3. In addition to tyrosine phosphorylation, STAT3 undergoes constitutive serine phosphorylation in Src-transformed cells for induction of transcriptionally functional STAT3. To demonstrate this, we first assay for STAT3 serine phosphorylation levels by Western blot analysis using phosphoserine 727-specific anti-Stat3 antibodies (Frank, et al., 1997, J. Clin. Invest. 100:3140-3148, Gollob, et al., 1999, J. Immunol. 162:4472-4481). Our results show strikingly that STAT3 is constitutively phosphorylated on serine 727 in Src-transformed fibroblasts compared to their normal counterparts (FIG. 12A, lanes 1 and 2). To show that MAPK members are required for this event, Src-transformed fibroblasts are treated with PD98059 or SB202190 and prepared cell lysates are prepared for phosphoserine-Stat3 Western blot analysis. Treatment with either PD98059 or SB202190 blocks serine phosphorylation of STAT3 (FIG. 12A, lanes 2, 3 and 4). These results establish that STAT3 serine phosphorylation is constitutive in NIH 3T3 fibroblasts stably transformed by Src, and provide evidence that MAPK family members are major mediators of this effect.

To show that PD98059 and SB202190 have an influence on the STAT3 DNA-binding activity induced by v-Src, nuclear extracts are prepared from fibroblasts expressing v-Src that have been treated with or without inhibitors. STAT DNA-binding activities in extracts containing equal amounts of total proteins are analyzed by electrophoretic mobility shift assays (EMSA) using an oligonucleotide probe corresponding to the M67 variant of the c-fos gene's sis-inducible element (SIE), which binds both activated STAT1 and STAT3 (Wagner, et al., 1990, EMBO J. 9:4477-4484). Expression of v-Src induces STAT3 tyrosine phosphorylation and DNA-binding activity (FIG. 12B, lanes 1 and 2). Moreover, treatment of v-Src-expressing cells with PD98059 or SB202190 has no effect on STAT3 DNA-binding activity induced by v-Src (FIG. 12B, lanes 2, 3 and 4). For controls, the binding of STAT3 to M67SIE is competitively inhibited by a molar excess of cold, unlabelled M67SIE but not by the unrelated c-fos intragenic regulatory element (FIRE) oligonucleotide, showing the specificity of DNA binding. Furthermore, STAT3 binding is blocked and supershifted by anti-Stat3 antibodies, but not by anti-Stat1 antibodies, demonstrating that the DNA-binding complex in this case contains STAT3. These results show that inhibition of STAT3 serine phosphorylation has no effect on the constitutive STAT3 DNA-binding activity in cells expressing v-Src. Taken together, our findings demonstrate that constitutive STAT3 serine phosphorylation in Src-transformed cells is dependent on signaling through MAPK family members.

p38 and JNK are Activated in Src-transformed Fibroblasts.

The results presented above show that p38 and JNK are key components of the signaling leading to STAT3 transcriptional activity induced by v-Src. Next, is shown that these kinases are constitutively activated in cell lines stably transformed by Src. The activity levels of p38, JNK and ERKs are assayed by Western blot analysis using antibodies specific to the phosphorylated, activated forms. Significantly, it is observed that both p38 and JNK1/2 are highly activated in v-Src-transformed compared to normal NIH 3T3 fibroblasts (FIGS. 13A and B, lanes 2 and 3). In contrast, no substantial induction of ERK1/2 is observed in Src-transformed over normal NIH 3T3 cells (FIG. 13C, lanes 2 and 3).

Next is shown the effects of PD98059 and SB202190 on the activation of these MAPKs. As expected, treatment of Src-transformed fibroblasts with PD98059 causes a complete block of basal ERKs activity (FIG. 13C, lanes 3 and 4). Combined with the results set forth in FIG. 8B, these findings indicate that the suppression of STAT3 transcriptional activity by PD98059 is the sum of the effects of this inhibitor on MKK1/2, JNK and p38 activities. Because SB202190 directly blocks p38 kinase activity, treatment of Src-transformed cells with this inhibitor does not significantly alter the phosphorylation of MAPK members, including p38 (FIGS. 13A, B and C, lanes 3 and 5). The apparent high induction of p38 phosphorylation when SB202190 is present may be due to a positive feedback response by MKK3 or MKK6 to the diminished p38 kinase activity. This is the first evidence of constitutive activation of both endogenous p38 and JNK in stable Src-transformed fibroblasts, and shows that the activated stress pathway cooperates with STAT3 signaling induced by Src. Altogether, these findings demonstrate crosstalk between Ras-Rac1-mediated activities of p38lJNK and STAT3 signaling in Src-transformed cells.

Because these examples demonstrate p38, and to a lesser extent JNK 112, are the key serine/threonine kinases involved in STAT3 signaling in Src-transformed cells, it is shown that STAT3 can be a direct substrate for these MAPKs in vitro. Results in FIG. 13D show that p38 and JNK can effectively phosphorylate STAT3 in vitro. STAT3 phosphorylation by ERK, however, is minimal compared to levels achieved for JNK and p38. A splice variant of full-length STAT3 with a C-terminal deletion, STAT3b, which lacks the serine 727 and therefore cannot transactivate in many cell types is used as a control (Caldenhoven, et al., 1996, J. Biol. Chem. 271:13221-13227, Turkson, et al., 1998, Mol. Cell. Biol. 18:2545-2552). The STAT3 and STAT3b proteins used as substrates in this assay maintain correct protein folding as they are purified by virtue of their DNA-binding activity to a STAT3-specific site. Results show that STAT3b does not undergo serine phosphorylation by any of the MAPKs (FIG. 13D), consistent with serine 727 as the site of phosphorylation. These results show that all three MAPKs are capable of using STAT3 as substrate in vivo, although the actual contributions of the individual MAPK family members in vivo will depend on the extent of their activation by v-Src.

Inhibition of p38 Activity Blocks Constitutive STAT3 Signaling and Src Transformation. Results presented above from transient transfection assays with reporter constructs show that MKK-mediated p38, and to a lesser extent JNK, activities are required for constitutive STAT3 signaling in Src-transformed cells. To further demonstrate this requirement, we show the effects of inhibition of MKKs or p38 on the induction of the STAT3-dependent luciferase reporter, pLucTKS3, in v-Src-transformed fibroblasts that stably express this reporter. Because STAT3 is constitutively activated in Src-transformed cells (Yu, et al., 1995, Science 269:81-83), NIH 3T3/v-Src/TKS3 cells stably expressing the STAT3 reporter exhibit very high luciferase activity reflecting constitutive STAT3-dependent induction of this reporter. As seen in transient transfections, treatment of NIH 3T3/v-Src/TKS3 cells with PD98059 or SB202190 partially or completely suppresses constitutive induction of the STAT3-dependent luciferase reporter, respectively (FIG. 14A), consistent with an obligatory requirement for p38 in constitutive STAT3 signaling in Src-transformed cells. p38-mediated STAT3 serine phosphorylation is required for v-Src transformation. This is shown by demonstrating the effects of inhibition of p38 on anchorage-independent growth of Src-transformed fibroblasts in soft-agar suspension. Treatment of cells in agar with SB202190 completely blocks colony formation of Src-transformed cells (FIG. 14B). In contrast, treatment with the same inhibitor has no significant effects on colony formation by Ras-transformed fibroblasts, which do not require STAT3 activation (FIG. 14C). Thus, the inhibition by SB202190 of Src-transformation is not the outcome of gross cytotoxicity. These studies show that p38 activity and STAT3 serine phosphorylation are required for transformation by Src but not by Ras. The effect of inhibition of MKK1/2 by PD98059 on anchorage-independent growth of fibroblasts transformed by v-Src or v-Ras is also shown. Results show a lack of significant effect of this inhibitor on transformation by either oncoprotein (FIGS. 14B and 7C), showing that inhibition of MKK1/2 is not sufficient to block Src or Ras transformation. Together, these results demonstrate that p38 activity is required for STAB-mediated gene regulation and v-Src transformation.

Discussion

In parallel to the constitutive DNA-binding activity and tyrosine phosphorylation of STAT3, the Src oncoprotein recruits additional signaling pathways crucial for STAT3 function (FIG. 15). Upstream of these signals is Ras, which functions to coordinately integrate serine/threonine kinase activities necessary for efficient STAT3 transcriptional activity. As one of the Ras-mediated pathways, MKK-ERK signaling interacts with that of STAT3.

Positioned downstream from Ras, the Rac1 family of small G proteins is key to signals that induce p38 and JNK serine/threonine kinases. We show that Rac1 signaling is recruited by V-Src, and demonstrate that STAT3 signaling induced by v-Src requires components of Rac1 signaling, including MLK family members and MKK4. The rescue of STAT3 function by p38 and JNK proteins from inhibition induced by dominant-negative Ras provides compelling evidence that these serine/threonine kinases are key in Src-induced STAT3 signaling. Thus, the essential role of Ras in this STAT3 signaling is the recruitment of Rac1-mediated p38 and JNK activities. Both p38 and JNK activities are constitutively-induced in cells stably transformed by Src. The aberrant constitutive activation of these two kinases may be essential to maintain the observed elevated STAT3 serine phosphorylation and transcriptional activity in Src-transformed cells. This is the first demonstration of constitutive induction of p38, JNK, and STAT3 serine phosphorylation in cells stably transformed by Src, and provides evidence that these events are associated.

Our findings presented here define signal transduction networks from v-Src to STAT3 in NIH 3T3 fibroblasts that integrate tyrosine and serine/threonine kinase pathways (FIG. 15). This provides a key role for Ras, which regulates the contributions of the MKK1/2 cascade and the Rac1-mediated stress-activated pathways involving p38 and JNK. While Ras has been shown to have an essential role in transformation of NIH 3T3 cells by v-Src, more recent studies have demonstrated that Ras is not required for Src transformation of chicken embryo fibroblasts or Rat-2 fibroblasts (Aftab, et al., 1997, Proc. Natl. Acad. Sci. USA. 94:3028-3033). Thus, the requirement for Ras-mediated signaling in Src transformation is cell type specific. Our results also indicate that downstream events, such as p38 and JNK signaling, are not sufficient to induce STAT3 transcriptional activity in the absence of Src. Nevertheless, activation of the stress signaling pathways involving p38 and JNK is obligatory for STAT3 function.

Because serine phosphorylation of STAT3 is required for its maximal transcriptional activity, and STAT3 signaling is obligatory for Src transformation, the present example shows that p38 and JNK-mediated STAT3 serine phosphorylation is necessary for Src oncogenesis. Thus, it is highly significant that inhibition of p38-mediated STAT3 serine phosphorylation blocks transformation by v-Src and not other oncoproteins like Ras that do not induce STAT3 signaling. These findings underscore the functional importance of p38 in mediating STAT3 serine phosphorylation in Src oncogenesis. In addition, the pathways delineated here are relevant to normal STAT3 signaling because recent studies demonstrate that p38 induces STAT3 serine phosphorylation in T cells in response to IL-12 and IL-2. This example provides the first evidence detailing crosstalk between the Ras/Rac1-mediated p38/JNK pathways and STAT3 signaling leading to serine phosphorylation of STAT3 in the context of oncogenesis. The example also demonstrates a convergence at the level of STAT3 of multiple signaling pathways activated by Src. These novel observations provide new insight into some of the signaling pathways induced by the Src oncoprotein that potentially have critical roles in cell transformation and human cancer.

Example 9

Constitutive Activation of STAT3 Signaling Confers Resistance to Apoptosis in Human U266 Myeloma Cells Example 9, shows that inhibition of STAT3 signaling promotes apoptosis in myeloma tumor cells, and that this effect is mediated by the antiapoptotic protein Bcl-$x_L$, which is under transcriptional control of STAT3. Therefore, inhibition of STAT3 signaling is desirable in the present invention to promote apoptosis in specifically tumor cells. In the subsequent related example, Bcl-$x_L$, is shown to cause resistance of tumor cells to chemotherapeutic agents, thereby supporting inhibition of STAT3 signaling as a means in the present invention of enhancing the effectiveness of chemotherapy and radiation therapy.

Interleukin 6 (IL-6) is the major survival factor for myeloma tumor cells and induces signaling through the signal transducer and activator of transcription (STAT) proteins. We show in this example that one STAT family member, STAT3, is constitutively activated in bone marrow mononuclear cells from patients with multiple myeloma and in the IL-6-dependent human myeloma cell line, U266. Moreover, U266 cells are inherently resistant to Fas-mediated apoptosis and express high levels of the anti-apoptotic protein, Bcl-$x_L$. Blocking IL-6 receptor signaling from Janus kinases to the STAT3 protein inhibits Bcl-$x_L$ expression and induces apoptosis, demonstrating that STAT3 signaling is essential for the survival of myeloma tumor cells. These findings show that constitutively-activated STAT3 signaling contributes to the pathogenesis of multiple myeloma by preventing apoptosis, and that inhibition of STAT3 is thereby desirable to promote apoptosis in these tumor cells.

Methods

Cells and Inhibitors.

U266 and RPMI 8226 cell lines are originally obtained from ATCC and maintained in RPMI 1640 medium supplemented with 10% fetal calf serum (FCS). For detection of STATs in primary bone marrow (BM) cells, BM aspirates are diluted 1:2 in phosphate-buffered saline (PBS) and mononuclear cells are separated by the standard Ficoll-Hypaque (Pharmacia LKB Biotechnology) sedimentation procedure. Mononuclear cells are washed twice with PBS, and nuclear extracts are prepared as described below. For inhibitor studies, a minimum of $10^7$ U266 cells are treated with 1 mg/ml Sant7 or with 50 mM AG490 (Meydan, et al., 1996, Nature 379:645-648). NIH 3T3 cells overexpressing the human EGF receptor have been described (Garcia, et al., 1997, Immunity 5:449-460).

Nuclear Extracts and EMSA.

Nuclear extracts are prepared as previously described. Briefly, nuclei are isolated and extracted in hypertonic buffer (20 mM HEPES, pH 7.9, 420 mM NaCl, 1 mM EDTA, 1 mM EGTA, 20% glycerol, 20 mM NaF, 1 mM $Na_3VO_4$, 1 mM $Na_2P_4O_7$, 1 mM DTT, 0.5 mM PMSF, 0.1 mM aprotinin, 1 mM leupeptin, and 1 mM antipain). Extracts are normalized for total protein, and 2-6 mg of protein is incubated with the $^{32}$P-labeled high-affinity SIE probe, (5'-AGCTTCATTTC-CCGTAAATCCCTA-3') (SEQ ID NO:2) derived from the c-fos gene promoter, as described (Yu, et al., 1995, Science 69:81-83; Garcia, et al., 1997, Cell Growth Diff. 8:1267-1276). Protein-DNA complexes are resolved on 5% non-denaturing polyacrylamide gels and analyzed by autoradiography. Controls are performed using rabbit polyclonal antibodies specific for STAT1, STAT3, or STAT5 proteins (Santa Cruz Biotechnology). The anti-Stat3 and anti-Stat5 antibodies supershift DNA-binding complexes, whereas the anti-Stat1 antibodies block complex formation (Yu, et al., 1995, Science 69:81-83; Garcia, et al., 1997, Cell Growth Diff. 8:1267-1276). For competition assays, nuclear extracts containing equal amounts of total protein are incubated with 100-fold molar excess of unlabeled SIE oligonucleotide or unlabeled irrelevant oligonucleotide, which contains the c-fos intragenic regulatory element (FIRE, 5'-GTCCCCCG-GCCGGGGAGGCGCT-3') (SEQ ID NO: 3).

Flow Cytometry and Apoptosis Assays.

For surface detection of the Fas receptor, $10^6$ cells are suspended in 100 ml PBS with 2.5 mg/ml mouse IgM (Sigma) and 100 mg UB2 antibody (MBL) or $IgG_1$, isotype control serum (Dako). Following 30 min incubation at room temperature, cells are washed with PBS, and incubated in the dark for 30 min with goat anti-mouse Ig-FITC. Fluorescence is measured on a FACScan flow cytometer and analyzed using CellQuest software (Becton Dickinson). For cell cycle analysis, $10^6$ cells are fixed in ice-cold ethanol for a minimum of 2 h, washed with PBS, and stained with 5 mg/ml propidium iodide (PI) and mg/ml RNase A at 37° C. for 30 min prior to analysis by flow cytometry. Sensitivity to Fas-mediated apoptosis is determined by exposing cells to 500 ng/ml agonistic antibody (CH-11, MBL) or 100 ng/ml Fas ligand (Alexis) for 18-24 h. Apoptosis is measured by staining with Annexin V-FITC (Clontech) and flow cytometry analysis. Fas-specific death is calculated as (% Annexin V positive cells in the CH-11 treated population)–(% Annexin V positive cells in the IgM control population). Programmed cell death in cells transfected with the bicistronic green fluorescent protein vectors (pIRES-EGFP or pIRES-Stat3b) is analyzed after staining with Annexin V-PE (Pharmingen) by two color flow cytometry analysis. Apoptotic morphology of DAPI-stained nuclei and green/red fluorescence is confirmed by fluorescence microscopy.

Western Blot Analysis.

Cells are lysed in a buffer composed of 50 mM Tris-Cl, pH 7.4, 5 mM EDTA, 150 mM NaCl, and 0.5% Triton-X 100 containing 1 mg/ml leupeptin and aprotinin, and 1 mM PMSF. Protein content of the cell lysates is quantified by the Bradford assay (Bio-Rad), and 15 mg total protein is dissolved in Laemmli SDS-PAGE sample buffer prior to separation by 10% SDS-PAGE. Proteins are transferred to PVDF membrane and Western blot analysis is performed by standard techniques with ECL detection (Amersham). The $Bcl-x_L$ antibody, clone 124 (Dako), is used at a 1:2000 dilution. The $Bcl-x_L$, antibody, clone S-18 (Santa Cruz Biotechnology), is used at a 1:500 dilution. Blots are quantified by densitometry and expression levels were normalized to b-actin (Sigma).

RNA Isolation and RT-PCR Analysis.

Total RNA is isolated by lysis in guanidine isothiocyanate followed by centrifugation through a cesium chloride gradient. cDNA is prepared from 200 ng of total RNA in a 40 ml reaction with AMV-RT (Boehringer-Mannheim). Specific gene amplification is performed on 5 ml of the cDNA reaction with the following primers: bcl-2: 5'-CGACGACTTCTC-CCGCCGCTACCGC-3' (SEQ ID NO: 4), and 5'-CCGCAT-GCTGGGGCCGTACAGTTCC-3' (SEQ ID NO: 5), which corresponds to bases 1761-1785; bcl-x: 5'-CGGGCAT-TCAGTGACCTGAC-3' (SEQ ID NO: 6) and 5'-TCAG-GAACCAGCGGTTGAAG-3' (SEQ ID NO: 7) which amplifies a 340 bp amplicon of $bcl-x_L$ or a 151 bp amplicon of $bcl-x_L$; and histone 3.3: 5'-CCACTGAACTTCTGATTCGC-3' (SEQ ID NO: 8) and 5'-GCGTGCTAGCTGGATGTCTT-3' (SEQ ID NO: 9). Tem ml of PCR products are electrophoresed on a 5% acrylamide gel and quantified by phosphorimaging using ImageQuant software (Molecular Dynamics).

Construction of Plasmids.

The murine bcl-x promoter reporter constructs are derived from a 3.2 kb genomic fragment containing the 5' region of the bcl-x gene upstream of the ATG translational start codon and have been described in detail (Grillot, et al., 1997, J. Immunol. 158:4750-4757). To construct the pGL2-mST1 reporter, three bases are mutated in the STAT1-binding motif (normal: TTCGGAGAA (SEQ ID NO: 10), mutant: TGAG-GATAA (SEQ ID NO: 11)) at positions –315 to –307 (Grillot, et al., 1997, J. Immunol. 158:4750-4757) in the 600 bp fragment of the mouse bcl-x promoter. The equivalent site in the human promoter was mutated previously (Fujio, et al., 1997, J. Clin: Invest. 99:2898-2905). The pMvSrc vectorencoding v-Src protein has been described (Turkson, et al., 1998, Mol. Cell. Biol. 18:2545-2552). To construct pIRES-Stat3b, the human STAT3b gene is excised from plasmid pSG5hSTAT3b by XhoI digestion, made blunt-ended with Klenow fragment of DNA polymerase, and subcloned into the EcoRV site of pIRES-EGFP vector (Clontech). The structure of pIRES-Stat3b is confirmed by restriction mapping, DNA sequencing, and functional analyses in transient transfections.

Transfections and Luciferase Assays.

Transfections of NIH 3T3 are performed by the calcium-phosphate method as previously described (Turkson, et al., 1998, Mol. Cell. Biol. 18:2545-2552). A total of 20 mg of DNA is added to cells, including 4 mg of the indicated luciferase reporter construct, 200 ng b-galactosidase expression vector, and 4-8 mg each of pMvSrc or pIRES-Stat3b. Cells are incubated for 48 h, lysed and cytosolic extracts prepared as described (Turkson et al., 1998, Mol. Cell. Biol. 18:2545-2552). The cytosolic fractions are used for luciferase assays (Promega) and analyzed with a luminometer. Samples are normalized to b-galactosidase activity by colorimetric assay at $A_{570}$ as an internal control for transfection efficiency. Transfections of the U266 myeloma cell line are performed by adding DNA to 300 ml RPMI 1640 media and mixing with 30 ml TransIT-LT1 (PanVera). A total of 25 mg of DNA is added in 10 ml serum-free media, including 8 mg of the indicated luciferase reporter construct, 2 mg of b-galactosidase vector, and 8 mg of pIRES-Stat3b or pIRES-EGFP. Cells are incubated 3 hours and fresh media is added to give a final concentration of 10% FCS. Cytosolic extracts are prepared 48 hours post transfection, and luciferase activities are normalized to b-galactosidase activity in all samples as described above.

Results

High Frequency of STAT Activation in Human Multiple Myeloma Tumors

To demonstrate the prevalence of STAT activation in primary myeloma tumors, STAT activity in the mononuclear fraction of bone marrow specimens obtained from patients with multiple myeloma is evaluated. STAT activation can be detected by elevated DNA-binding activity as measured in electrophoretic mobility shift assays (EMSA) using an oligo-nucleotide probe corresponding to the sis-inducible element (SIE), which binds activated STAT1 and STAT3. Nuclear extracts prepared from bone marrow specimens reveal elevated SIE-binding activity, to varying extents, in all 24 multiple myeloma patients examined, with dramatic elevation in one-third of these (FIG. 16a). In contrast, little or no activated STATs is detected in bone marrows from normal individuals or patients with no evidence of bone marrow m etastases. To identify the STAT family members activated in multiple myeloma tumor cells, supershift experiments are performed using antibodies specific for different STATs. STAT3 homodimers and STAT1:Stat3 heterodimers are the predominant forms of activated STATs in the majority of multiple myeloma specimens examined (FIG. 16b). STAT1 homodimer activation is present at a lower frequency, and no STAT5 activation is detected using a STAT5-specific probe. These results demonstrate a high incidence of constitutively elevated STAT3 activation in multiple myeloma tumor cells.

Stat3 Activation in U266 Myeloma Cells is Constitutive and Dependent on Signaling from IL-6 Receptor to JAK Family Kinases.

The human myeloma cell line, U266, has a well-characterized IL-6 autocrine loop and depends on its own production of the cytokine for growth and survival (Schwab, et al., 1991, Blood 77:587-593; Keller and Erschler, 1995, J. Immunol. 154:4091-4098). Nuclear extracts prepared from U266 cells exhibit constitutive SIE-binding activity that is specifically competed by unlabeled SIE but not by an irrelevant oligonucleotide (FIG. 17a). Although U266 cells are dependent on an IL-6 autocrine loop, stimulation with exogenous IL-6 induces further activation of STAT DNA-binding activity. To confirm the identity of STAT family members activated in U266 cells, control experiments are performed using nuclear extracts from EGF-stimulated NIH 3T3 cells as a reference (Zhong, et al., 1994, EMBO J. 15:4515-4525) and antibodies specific for different STAT family members. The SIE-binding activity in U266 cells contains predominantly activated STAT3 homodimers and, to lesser extents, STAT1:Stat3 heterodimers and STAT1 homodimers (FIG. 17a). This pattern of STAT activation in U266 cells is thus similar to that of many multiple myeloma tumor specimens described above.

Sant7 is a potent IL-6 superantagonist that competes with IL-6 for binding to surface IL-6 receptors and prevents the gp130 subunits from oligomerizing and initiating downstream signaling (Sporeno, et al., 1996, Blood 87:4510-4519). Inhibition of IL-6 receptor signaling by Sant7 reduces constitutive STAT3 DNA-binding by nearly 70% within 12 hours and persists for at least 24 hours in U266 cells (FIG. 17b). Involvement of JAKs in STAT3 signaling is demonstrated by using a specific inhibitor of JAK family kinases, the tyrphostin AG490. Constitutive STAT3 DNA-binding activity is inhibited by AG490 in a time-dependent manner, with complete abrogation of STAT3 activity occurring within 16 to 24 hours in U266 cells (FIG. 17c). Together, these results demonstrate that the majority of constitutive STAT3 activation observed in U266 myeloma cells is mediated by IL-6 signaling from the IL-6 receptor to JAK family kinases.

U266 Myeloma Cells Express Elevated Levels of Bcl-x, and are Inherently Resistant to Apoptosis Comparison of the two model human myeloma cell lines reveals a relative difference in resistance to Fas-mediated apoptosis by the IL-6-dependent cell line U266 as compared to 8226, which is not dependent on IL-6. Both myeloma cell lines express high levels of Fas on their cell surface (FIG. 18a). However, treatment of 8226 cells with Fas ligand or the agonistic mAb, CH-11, results in 40-65% apoptosis, whereas U266 cells are completely resistant to Fas-mediated cell death (FIG. 18b). This resistance cannot be attributed to reduced receptor expression, nor is it due to function-ablating mutations (Landowski, et al., 1997, Blood 90:4266-4270). To show the mechanism of Fas resistance in the U266 cell line, we examine the expression of the anti-apoptotic proteins, Bcl-2 and Bcl-$x_L$. Constitutive mRNA and protein expression of both Bcl-2 and Bcl-$x_L$ are higher in U266 cells as compared to 8226 cells, with levels 2- to 7-fold greater after normalization (FIG. 18c).

AG490 Inhibits Expression of Bcl-x, and Promotes Apoptosis in U266 Cells

To demonstrate the role of IL-6-mediated Bcl-$x_L$, expression in regulating apoptosis of U266 cells the IL-6 receptor signal transduction is disrupted. Inhibition of JAK family kinase activity by AG490 treatment results in a significant reduction of bcl-x mRNA expression following 24 hours of exposure, and by 30 hours the Bcl-$x_L$ protein levels are nearly absent (FIG. 19a). The kinetics of Bcl-$x_L$ inhibition closely follow the kinetics of STAT3 inhibition by AG490 (compare with FIG. 17c). In contrast, AG490 has no effect on the expression of Bcl-2 or the housekeeping genes, histone 3.3 and a-actin, demonstrating that AG490 treatment does not induce a general block in gene transcription or translation.

The inhibition of Bcl-$x_L$, expression by AG490 increases sensitivity to Fas-mediated apoptosis. Following 24 hours of exposure to AG490, U266 cells are treated with the Fas agonistic mAb, CH-11, for an additional 12 hours and analyzed for programmed cell death. Strikingly, following reduction in Bcl-$x_L$ expression, U266 cells display a marked increase in sensitivity to Fas-mediated apoptosis (FIG. 19b), with up to 90% of cells undergoing apoptosis This effect is not a general stress response, as AG490 treatment does not enhance sensitivity to Fas-mediated cell death in the IL-6-independent 8226 cells. With extended exposure to AG490 for 48 h, 70% of U266 cells accumulate in G1, and at 72 hours display extensive spontaneous cell death. Combined with the data in FIG. 17, these findings show that STAT3 signaling contributes to the resistance of U266 cells to programmed cell death by inducing expression of Bcl-$x_L$.

Dominant-Negative STAT3 Protein Inhibits Expression of Bcl-$x_L$, and Promotes Apoptosis 25 in Transfected U266 Myeloma Cells Because multiple signal transduction pathways have been shown to originate from the IL-6 receptor, the effects of a dominant-negative STAT3 protein on Bcl-$x_L$ expression and cell survival are analyzed. STAT3b is a naturally-occurring splice variant of STAT3 that lacks the C-terminal transactivation domain and functions in a dominant-negative manner to block STAT3-mediated gene regulation in many but not all cell types. U266 cells arc transiently-transfected with an enhanced green fluorescent protein (EGFP) expression construct encoding STAT3b (pIRES-Stat3b) or the empty vector (pIRES-EGFP). This construct contains an internal ribosomal entry site, allowing translation of STAT3b and EGFP from a single bicistronic mRNA. Because of the low transfection efficiency of human myeloma cells, STAT3b-expressing cells are isolated by FACS on the basis of EGFP expression and then analyzed for Bcl-$x_L$ levels 48 hours post-transfection. Western blot analyses of FACS-sorted STAT3b-expressing cells reveal decreased Bcl-$x_L$ expression relative to empty vector transfectants (FIG. 20a). Based on normalization to a-actin protein levels probed on the same blot, results indicate that Bcl-$x_L$ protein levels are decreased by nearly 80% in the STAT3b-expressing cells. In separate experiments, mRNA is extracted from FACS-sorted STAT3b-expressing cells or empty vector transfectants and analyzed by RT-PCR. Results demonstrate a reduction in bcl-x mRNA levels, similar to the reduction in Bcl-$x_L$ protein, in STAT3b-expressing cells (FIG. 20a). In contrast, Bcl-2 protein and mRNA levels are not substantially reduced in STAT3b-expressing cells, consistent with the AG490 results described above.

Significantly, when transiently-transfected STAT3b-expressing U266 cells are examined by Annexin V-PE staining and FACS analysis, a high level of apoptosis is observed relative to empty vector transfectants. At 72 hours post-transfection, 66% of STAT3b-expressing cells were apoptotic, compared to only 28% of cells transfected with empty vector (FIG. 20b). There is only a modest increase in apoptosis of STAT3b-expressing cells in response to the Fas agonistic antibody, CH-11, probably due to the high levels of spontaneous apoptosis already in progress in STAT3b-expressing cells. These conclusions are confirmed by fluorescence and light microscopy of STAT3b-expressing cells enriched by FACS sorting on the basis of EGFP expression. Following staining with DAPI for morphological examination, fluorescence microscopy is used to identify green fluorescent cells expressing STAT3b. Results show that the majority of cells expressing STAT3b exhibit nuclear fragmentation characteristic of apoptosis, whereas cells not expressing STAT3b are normal in appearance (FIG. 21). These results demonstrate that STAT3-dependent signaling is critical for the survival of myeloma tumor cells and their resistance to programmed cell death.

Stat3 Regulates Transcription from the bcl-x Gene Promoter

The above results show that STAT3-mediated signaling regulates Bcl-$x_L$ expression. Mouse bcl-x promoter constructs are used to demonstrate transcriptional regulation of the bcl-x promoter by STAT3. These constructs are fused to a luciferase reporter gene (FIG. 22a). As shown in FIG. 22b, activation of endogenous STAT3 by v-Src induces the expression of bcl-x reporters 5- to 20-fold over basal levels in transfected NIH 3T3 cells. This induction is STAT3-specific because it is effectively disrupted by overexpression of STAT3b. Further analyses using serial upstream truncations of the bcl-x gene reveal that the 600 bp promoter-proximal region contained in pGL2-0.6R is sufficient for STAT3-mediated induction in response to v-Src (FIG. 22b). In addition, mutation of the reported STAT1-binding site in this region of the bcl-x promoter (Fujio, et al., 1997, J. Clin. Invest. 99:2898-2905) does not diminish transcriptional induction by v-Src (FIG. 22b). Because v-Src induces exclusively STAT3, and not STAT1 or other STAT family members in NIH 3T3 cells, these results demonstrate that STAT3 alone can mediate induction of the bcl-x promoter.

Consistent with the observations in fibroblasts, transfection of U266 myeloma cells with the bcl-x promoter constructs results in greater than 25-fold increases in expression of these reporters relative to control promoter in the inverse orientation (FIG. 22c). Furthermore, transfected U266 cells respond to exogenous IL-6 stimulation with an additional induction of the bcl-x promoter above the constitutive levels. Both the constitutive and IL-6 induced activation of the bcl-x reporters is dependent on endogenous STAT3, as demonstrated by the ability of overexpressed STAT3b to block this induction in a dominant-negative manner. As in fibroblasts, the 600 bp bcl-x promoter-proximal region is sufficient to confer constitutive and IL-6 induced expression in myeloma cells, and the STAT1-binding site mutant, pGL2-mST1, shows an increase in expression relative to pGL2-0.6R (FIG. 22c). These results are consistent with our finding that this highly conserved 600 bp region of the mouse and human bcl-x genes harbors multiple STAT3-binding sites, also called acute-phase response elements or APRE sequences.

Discussion

Our findings delineate a complete signaling pathway from IL-6 through STAT3 to the bcl-x gene (FIG. 22d), and demonstrate that STAT3 signaling confers resistance to apoptosis in human myeloma tumor cells. These novel results provide evidence that constitutively-activated STAT3 signaling contributes to the malignant progression of multiple myeloma by preventing apoptosis, thus allowing accumulation of long-lived myeloma tumor cells. Protection from apoptosis in myeloma cells can be mediated by STAT3-induced expression of Bcl-$x_L$. This conclusion is supported by observations that blocking STAT3 signaling inhibits Bcl-$x_L$ expression and induces apoptosis of myeloma cells. While it is likely that multiple cellular mechanisms contribute to the survival of multiple myeloma cells, results presented here demonstrate an essential role for STAT3 signaling in preventing apoptosis of myeloma tumor cells.

The presence of APRE sequences and the response to IL-6-induced STAT3 activation define bcl-x as a classical acute-phase response gene. Protection from programmed cell death can be a feature in common between the IL-6-induced acute phase response and malignant progression of multiple myeloma tumors. EMSA analyses using oligonucleotides corresponding to putative APRE sequences in the 600 bp promoter region reveals the presence of five STAT3-binding sites that do not bind STAT1, three of which are conserved between mouse and human. Thus, stimulation of STAT1 and STAT3 signaling through IL-6-related cytokines may confer cytoprotective effects through a common mechanism involving distinct STAT-binding sites in the bcl-x promoter. In contrast to transient cytoprotective effects that the acute phase response confers in normal cells, however, protection from cell death is chronic in tumor cells with constitutive STAT3 activation. This distinction is likely to be critical in the recruitment of this normally cytoprotective pathway to a participatory role in oncogenesis.

The anti-apoptotic activity of Bcl-$x_L$ has been attributed to its ability to form heterodimers and inactivate pro-apoptotic members of the Bcl-2 family, including Bad, Bax and Bak (Kelekar, et al., 1997, Mol. Cell. Biol. 17:7040-7046). Thus, dysregulated expression of any one of these proteins can result in an imbalance that affects the cellular response to physiological signals for apoptosis. Fas is a key physiological regulator of homeostasis in the immune system, where it functions to delete activated effectors of the immune response. We demonstrate that STAT3 signaling regulates Bcl-$x_L$ expression, and that blocking STAT3 signaling leads to enhanced susceptibility to Fas-mediated apoptosis and ultimately spontaneous programmed cell death. This is likely due to the relative increase in pro-apoptotic protein activity resulting from the reduced Bcl-$x_L$ expression.

Results presented here also have significant implications for treatment of human cancers with activated STAT3 signaling, in the present invention. Elevated Bcl-$x_L$ expression has been indicated as a mechanism of resistance to some chemotherapeutic drugs and radiation therapies that utilize cellular apoptosis pathways to eliminate tumor cells. Because disruption of STAT3 signaling reduces Bcl-$x_L$ expression and increases sensitivity to apoptosis, therapeutic strategies which disrupt STAT3 signaling will not only prevent malignant progression but also confer sensitivity to certain chemotherapeutic drugs and radiation therapy.

Thus, agents that selectively block STAT3 signaling can be used in combination with conventional chemotherapeutic agents, including but not limited to paclitaxel, cisplatin, vincristine, 5-fluorouracil, docetaxel, camptothecin, estramustine mitoxantrone, and prednisone, for more effective anti-tumor therapy. These findings further identify STAT3 as a target for therapeutic intervention in multiple myeloma and other human cancers with activated STAT3 signaling.

Example 10

Stat3 and Bcl-x Expression in Myeloma Cells: Effects on Chemotherapy

Example 10 demonstrates that overexpression of Bcl-x confers resistance to chemotherapy in myeloma cells. An embodiment of the present invention is the inhibition of STAT3 signaling for the purpose of enhancing the effectiveness of chemotherapy, to which this example directly relates.

Bcl-x Overexpression Confers Resistance to Chemotherapy in Myeloma Cells.

Stable transfectants of U266 cells overexpressing Bcl-$x_L$ protein tagged with the FLAG epitope are generated to demonstrate that Bcl-$x_L$ confers resistance to chemotherapy in myeloma cells. As shown in FIG. 23a, several stable clones are isolated that overexpress Bcl-$x_L$ to varying extents. These Bcl-$x_L$ overexpressing cells are resistant to apoptosis induced by AG490, as predicted since the ectopic Bcl-$x_L$ is expressed from a CMV promoter and is thus independent of JAK-STAT signaling. Significantly, the Bcl-x overexpressing cells are also resistant to apoptosis induced by the chemotherapy drugs, melphalan (LPAM) and mitoxantrone (FIG. 23b). These findings support one embodiment of the present invention, that Bcl-x confers resistance to chemotherapy-induced apoptosis, and therefore that inhibition of STAT3 signaling promotes chemotherapy-induced apoptosis.

Example 11

Stat3 as a Target for Gene Therapy: Dominant-Negative STAT3 Suppresses Growth of the Murine Melanoma 816 Tumor In Vivo In vitro expression of a STAT3 variant with dominant-negative properties, STAT3b, induces cell death in murine B16 melanoma cells that harbor activated STAT3. By contrast, expression of STAT3b has no effect on normal fibroblasts or the STAT3-negative murine tumor, MethA. Thus only tumor cells with activated STAT3 are dependent on this pathway for survival. Significantly, gene therapy by electroinjection of the STAT3b expression vector into pre-existing B16 tumors causes inhibition of tumor growth as well as tumor regression. This STAT3b-induced antitumor effect is associated with apoptosis of the B16 tumor cells in vivo. These findings demonstrate for the first time that interfering with STAT3 signaling induces potent antitumor activity in vivo, and thus identifies STAT3 as a molecular target for therapy of human cancers harboring activated STAT3.

Materials and Methods

Cell lines and culture medium. Mouse B16 melanoma cell line, MethA sarcoma cell line, and mammary carcinoma cell lines 4T1 and TSA are grown in RPMI 1640 (Gibco BRL, NY) supplemented with 10% fetal bovine serum (HyClone, UT), 2 mM L-glutamine, 1 mM 10 sodium pyruvate, 1% minimal Eagle's medium nonessential amino acids and 100 IU/ml penicillin/streptomycin. NIH 3T3 (ATCC) cell line is grown in Dulbecco's modified Eagle's medium (DMEM, Gibco BRL, NY) supplemented with 5% calf serum.

Nuclear extracts and EMSA. Nuclear extract preparation and electrophoretic mobility shift assays (EMSAs) are performed essentially as described earlier (Yu, et al., 1995, Science. 15 269:S1-83, Garcia, et al, 1997, Cell Growth Differ. 8:1267-1276, Catlett-Falcone, R., et al., 1999, Immunity 10:105-115).

Plasmids.

The construction and characterization of pIRES-Stat3b has been described (Catlett-Falcone, R., et al., 1999, Immunity 10: 105-115). STAT3b cDNA is also inserted into the pAd-CMV vector (Quantum Biotechnologies, Montreal, Qc). The ability of pAdCMV-Stat3b to express STAT3b protein is verified by Western blot analysis after transfection into NIH 3T3 cells.

Transfections and flow cytometric analysis. Transfections in vitro are performed by the lipofectamine-mediated method (Gibco BRL, NY). To determine transfection efficiency, relative fluorescence intensity is measured by fluorescence-activated cell sorting (FACS) of both pIRES-EGFP/p$SV_2$neo and pIRES-Stat3b/p$SV_2$neo transfected cells. For stable transfectants, one plate of transfected cells from each group is used for determining the transfection efficiency, and the remaining plates are allowed to grow in medium supplemented with 500 mg/ml G418. Two weeks later, the G418-resistant colonies are fixed in 4% paraformaldehyde and the number of colonies counted. GFP-positive colonies are counted (for B16 cells) or estimated (for NIH 3T3 cells) under fluorescence microscopy.

Mice and tumors. Six-week-old female C57BL mice are purchased from the National Cancer Institute (Frederick, Md.). Mice are shaved in the left flank area and injected subcutaneously (s.c.) with $2\times10_5$ B16 cells in 100 ml PBS. After 7-10 days, B16 tumors with a diameter of 3-6 multiple myeloma are established. Animals are stratified so that the mean tumor sizes in all treatment groups are nearly identical. Tumor volume is calculated according to the formula $V=0.52\times a^2 \times b$ (a, smallest superficial diameter; b, largest superficial diameter).

DNA electroinjection in vivo. The gene delivery procedure is performed after the mice are anesthetized. One hundred µg of plasmid DNA in 100 ml saline is injected directly into the tumor using a 25 gauge, 318 inch length needle. Electric pulses are delivered through custom designed electrodes, which are placed around the tumor, using a PA 4000 DC generator (Cyto Pulse Sciences, Inc., Columbia, Md.). Electroinjection of the tumor cells is accomplished by applying a total of fourteen 100 ms electric pulses at a nominal field strength of 1500 V/cm at 1 second intervals.

Histochemistry and immunohistochemistry. Electroinjection with pIRES-EGFP or pIRES-Stat3b is carried out in 4-5 multiple myeloma B16 tumors. Three days post in vivo transfection, mice are euthanized and the tumors are excised and immediately frozen in liquid $N_2$. Serial sections of tumors are also fixed in formalin, stained with H&E and processed for routine histologic examination. The anti-GFP monoclonal antibody (Clontech, Palo Alto, Calif.) is applied to 3 µM sections from frozen sections of tumors, using the avidin-biotin-peroxidase complex method (Vectastain Elite ABC kit, Vector, Burlingame, Calif.). All slides are lightly counter-stained with Mayer's hematoxylin for 30 s before dehydration and mounting. Non-immune protein (mouse IgG) negative controls are used for each section. For b-gal staining, tumor tissues are excised and fixed in 0.5% gluteraldehyde 3 days after electroinjection of either the b-gal or pcDNA3 plasmids. Cryostat sections are mounted on poly-lysine-coated slides and briefly fixed in 0.5% glutaraldehyde. The X-gal reaction is carried out according to the supplier's instructions (Boehringer Mannheim, Indianapolis, Ind.).

Terminal deoxynucleotidyl transferase-mediated dUTP-Digoxigenin nick-end-labeling (TUNEL) assay. B16 tumors that receive either p1RES-EGFP or pIRES-Stat3b electro injections are used for this assay. Three µm sections from parafinized tissues are dewaxed and rehydrated according to standard protocols. After incubation with proteinase K (30 min at 21° C.), the TUNEL reaction mixture (Boehringer Mannheim, Indianapolis, Ind.) is added to rinsed slides and incubated in a humidified chamber for 60 s at 37° C. This is followed by incubating with Converter-AP (50 ml) and substrate solution (50 ml). The reaction is visualized by light microscopy.

Results

Stat3 is constitutively-activated in murine tumor cells. Four murine tumor cell lines, comprising melanoma B16, mammary carcinomas TSA and 4T1, and sarcoma MethA, are evaluated for STAT DNA-binding activity in electrophoretic mobility shift assays (EMSA). An oligonucleotide probe corresponding to a high-affinity mutant of the sis-inducible element (hSIE), which binds activated STAT1 and STAT3 is used to determine whether the nuclear extracts from these tumor cells contain constitutively-activated STAT3 protein. With the exception of MethA, all of the other murine tumor cells contain elevated hSIE-binding activity corresponding to STAT3 homodimers (FIG. 24, a and b).

Overexpression of a STAT3 dominant-negative protein, STAT3b, induces cell death in B16 tumor cells in vitro. STAT3b is a naturally-occurring splice variant of STAT3 that lacks the C-terminal transcriptional activation domain and hence functions as a dominant-negative form of STAT3 in many cellular contexts. STAT3β is overexpressed in B16 cells to show that STAT3 signaling is essential for B16 cell survival in vitro. B16 cells are co-transfected with $pSV_2neo$ and either a vector encoding both enhanced green fluorescent protein (EGFP) and human STAT3b (pIRES-Stat3b), or the empty vector encoding only EGFP (pIRES-EGFP). Since the pIRES-Stat3b construct contains an internal ribosomal entry site (IRES) to allow translation of STAT3b and EGFP from a single bicistronic mRNA, detection of EGFP can be used as a marker for STAT3b expression in the same cell.

Transfection efficiencies with pIRES-EGFP or pIRES-Stat3b vectors are very similar as determined by the percentage of cells that exhibit green fluorescence at 36 hours post transfection (FACS analysis). The remaining transfected plates are selected in medium supplemented with G418. Since the transfection efficiencies of the two constructs in each experiment are nearly the same, over 95% of the B16 cells that received the STAT3b construct do not swive (only 6 colonies survive compared to 138 colonies in B16 cells transfected with the empty vector). Of the six surviving colonies, the intensity of green fluorescence is also much dimmer than in those transfected with the empty vector.

To determine whether expression of STAT3b can mediate cell death of other murine tumor cells with activated STAT3, transfection is carried out in the TSA murine breast carcinoma cell line. Consistent with the B16 cells, a marked reduction in the number of viable cells is observed in STAT3b-transfected TSA tumor cells, when compared to empty vector-transfected control cells.

To ensure that the lack of survival in cells that receive STAT3b is not due to non-specific toxicity, the same co-transfection conditions and G418 selection are performed with normal mouse NIH 3T3 fibroblasts. The number of G418-resistant clones are the same in both empty vector and STAT3b-transfected cells, and no differences in the number of GFP-positive clones or intensity of green fluorescence is observed. To assess whether the sensitivity to STAT3b expression in B16 cells is due to transformation in general or requires activated STAT3 signaling, MethA tumor cells that do not harbor constitutively-activated STAT3 are transfected with either pIRES-Stat3b or pIRES-EGFP. While the number of live B16 cells decrease dramatically as a result of STAT3b transient transfection, the number of live MethA cells in both STAT3b and vector control groups remain the same 48 hours post-transfection.

Intratumoral electroinjection of STAT3b vector leads to suppression of tumor growth in vivo. The efficacy of gene delivery into 4-5 multiple myeloma (average) B16 tumors is determined by examining the percentage of tumor cells positive for GFP or b-galactosidase (b-gal) after electroinjection with the respective vectors. Approximately 15% of the tumor cells are scored as positive for b-gal expression (FIG. 25(a)), and similar results are obtained scoring for GFP expression.

To determine the effects of STAT3b expression on in vivo tumor growth, we electroinject 3-6 multiple myeloma B16 tumors with either pIRES-EGFP or pIRES-Stat3b plasmids. Of the fifteen mice that receive the empty vector by electroinjection (pIRES-EGFP, 10 mice; pcDNA3, 5 mice), only one mouse temporarily regresses its tumor (FIG. 25c). In contrast, 11/20 tumors that receive STAT3b expression vectors (either pIRES-Stat3b or pAdCMV-Stat3b) regress (compare FIGS. 25c and d). Five of these eleven tumors demonstrate continue response, as no tumor regrowth is observed at the original tumor site at sacrifice. In all of the experiments, the growth of B16 tumors is clearly inhibited by STAT3b gene therapy in a majority of the mice (FIG. 25b). Injection of pIRES-Stat3b intratumorally without electroporation, however, has no inhibitory effect on tumor growth.

Stat3b-mediated tumor suppression involves apoptosis in Jan. 17, 2000 vivo. To determine the mechanism of tumor cell killing in vivo, B16 tumors (from experiment number 3 of FIG. 25b) treated with either the empty vector or the STAT3b vectors are excised for H&E staining and TUNEL assays. All of the 5 control tumors and 10 of the STAT3b-treated tumors are stained with H&E. While none of the 5 control tumors show more than 10% apoptotic cells, many of the STAT3b-treated tumors undergo massive apoptosis (FIGS. 26a and b). Out of the 10 STAT3b-treated tumors, 5 regressing tumors had more than 50% apoptotic cells (2 of them had greater than 90%). TUNEL/alkaline phosphatase assays for apoptosis confirm that STAT3b treatment induces extensive apoptosis in B16 tumors (FIGS. 26c and d). In addition to apoptosis, infiltrating inflammatory cells in the apoptotic tumors are observed in STAT3b-treated tumors.

Discussion

In this study, a syngeneic mouse tumor model system is used involving the poorly-immunogenic murine B16 tumor to show that constitutively-activated STAT3 is a valid molecular target for novel cancer gene therapy. Inhibition of activated STAT3 by its dominant-negative variant, STAT3b, leads to a significant inhibition of tumor growth mediated by tumor cell apoptosis in vivo.

The high incidence of STAT3 activation in human cancers from diverse origins implicates STAT3 signaling in neoplastic transformation. Results indicate that STAT3 is also constitutively activated with high incidence in murine tumors, highlighting the importance of STAT3 signaling in oncogenesis. Compared to the human myeloma line, U266, the levels of activated STAT3 in the B16 tumor cell line are relatively low (FIG. 24). Such low levels of STAT3 activation have also been observed in human tumor lines and tissues, including myeloma and breast cancer. The fact that expression of STAT3b kills nearly all of the B16 tumor cells in vitro suggests that low levels of constitutively-activated STAT3 is sufficient to maintain tumor cell survival. These results also imply that human tumors with low levels of constitutively-activated STAT3 are potential candidates for STAT3-targeted therapy. In contrast to B16 and TSA tumor cells, expression of STAT3b has no detectable effect on the survival of normal NIH 3T3 fibroblasts or the STAT3-negative MethA tumor cells, suggesting that cells lacking constitutively-activated STAT3 are resistant to STAT3-targeted therapy.

Recent studies described herein using human myeloma cells demonstrates that STAT3b inhibits expression of the Bcl-$x_L$ protein. These experiments show that STAT3b can be a pro-apoptosis regulator in cells that require STAT3 function for survival.

In the case of B16 tumors treated with the STAT3b gene via electroinjection, the number of apoptotic cells also exceeds the number of cells transfected, consistent with antitumor bystander effects. It is also notable that tumor infiltration by acute and chronic inflammatory cells is observed after STAT3b expression. Not to be limited by theory, these inflammatory cells may participate in killing of residual tumor cells. The bystander effect augments the usefulness of the present invention by killing tumor cells that surround transfected cells.

Example 12

The Antitumor Effect of an Inhibitor of STAT3 Signaling, the Tyrosine Kinase Inhibitor AG-490, is Enhanced by Interleukin-12.

This example shows how combining AG-490 and IL-12 is an effective approach for treatment of multiple myeloma as well as for other cancers harboring constitutively-activated JAK-STAT signaling, by demonstrating the effect of blocking JAK-STAT signaling with AG-490 on the survival of myeloma cells and on cytokine-mediated immune responses in syngeneic murine myeloma models. Both murine MOPC and MPC11 myeloma cells form rapidly growing and poorly immunogenic tumors. While in vivo treatment with AG-490 selectively induces apoptosis of myeloma cells, AG-490-induced tumor regression is transient. This transient effect of AG-490 in the syngeneic murine tumor models allows one to determine whether immunotherapy could potentiate AG-490-mediated antitumor effects. However, many cytokines, including IL-12, are known to signal through JAK-STAT pathways, and AG-490 may therefore inhibit cytokine-mediated immune responses, thus interfering with cancer immunotherapy. Our example demonstrates that in vivo administration of AG-490 does not reduce IL-12-mediated activation of macrophage cytotoxicity and IFN-g production by splenocytes. Furthermore, combinational therapy with IL-12 and AG-490 results in prolonged tumor regression. These results show that combining AG-490 and IL-12 may possess clinical potential as an effective approach for treatment of multiple myeloma as well as for other cancers harboring constitutively-activated JAK-STAT signaling.

Materials and Methods

Cell lines. The murine myeloma cell lines MOPC, S194, MPC11, and J558 are obtained from ATCC. All cell lines are maintained in DMEM medium supplemented with 10% fetal bovine serum, and 100 U/ml of penicillin/streptomycin.

Nuclear extracts and eletrophoretic mobility shift assay (EMSA). AG-490 in 0.1% DMSO is diluted to the appropriate concentrations with RPMI medium supplemented with 10% fetal bovine serum and antibiotics as described above. Tumor cells are treated with 50 mM AG-490 before isolation of nuclei. Nuclear extract preparation and EMSA are performed essentially as previously described (supra).

In vitro apoptosis assay. After a 24 hours incubation with LIMEM medium containing 0, 25, or 50 mM AG-490, cells are stained with Annexin V-PE and 7-Amino-actinomycin D (PharMingen, San Diego, Calif.). Dual-color fluorescence is measured on a FACScan flow cytometer and analyzed using CellQuest software (Becton Dickinson, Mountain View, Calif.).

Splenocytes and Interferon-Gamma (IFN-g) Production.

Mice are treated daily with i.p. injections of 100 ml of AG-490 (0.5 mg) or DMSO vehicle (50%) for a total of 4 days. During the last two days of AG-490 or DMSO treatment, daily i.p. injection of 400 ng of recombinant IL-12 (rIL-12) (Genetics Institute, Cambridge, Mass.) is also given simultaneously with either AG-490 or DMSO. Two days after the last treatment of AG-490, single cell suspensions of splenocytes are prepared from individual mice. The splenocytes are treated with 100 U/ml rIL-2 to induce IFN-g production. IFN-g ELISA (Genzyme, Cambridge, Mass.) is performed as described previously (Tan, et al., 1996, Cancer Res 56:3399).

Peritoneal macrophage preparation and cytostatic test. Peritoneal cells are prepared from the same mice treated with either AG-490/rIL-12 or DMSO/rIL-12 as described above. The peritoneal macrophage population is enriched by adhesion on plastic plates followed by washing and aspiration of non-adherent cells. The percentage of macrophages among adherent cells is estimated by morphological criteria using Giemsa staining (>95%). Antitumor cytostatic activity of macrophages is determined by inhibition of DNA synthesis of target tumor cells (J558 myeloma cells). Briefly, macrophage-sensitive J558 cells ($2\times10^4$/well) are co-cultured for 48 hours with and without macrophages ($2\times10^5$/well) prepared from individual mice. To estimate DNA synthesis, the cells are pulsed with $^3$H-thymidine ($^3$H-TdR) (0.25 mCi/well) during the last 6 hours of incubation. $^3$H-TdR incorporation is determined using a liquid scintillation b-counter (Pharmacia Wallac, Finland). Results are expressed as percentage of inhibition of $^3$H-TdR incorporation by J558 cells incubated with macrophages compared to $^3$H-TdR incorporation by J558 cells incubated in medium alone.

Nitric oxide production. Peritoneal macrophages ($2\times10^5$/0.2 ml/well) from mice with various treatments are incubated 48 hours. Nitrite accumulation in macrophage supernatants were determined using Griess reagent.

In vitro IL-12 activation and AG-490 treatment of macrophages. Peritoneal macrophages ($2\times105$/well) are incubated in medium supplemented with either PBS, or rIL-12 (2 ng/ml), or AG-490 (50 mM). Forty-eight hours later, the cultures are renewed by addition of fresh medium with either AG-490 or rIL-12 or PBS. Activation of macrophages is determined by nitric oxide production. Macrophage viability is determined by cleavage of tetrazolium salt in an MTT assay.

Mice and tumor formation in vivo. Six- to eight-week old female BALB/c mice are obtained from the National Cancer Institute (Frederick, Md.). Cohorts of 3-5 mice per group are used for these experiments. Mice are shaved on the right flank and injected subcutaneously (s.c.) with $5\times10^5$ of either MOPC or MPC11 cells in 100 mL of PBS to induce tumors.

In vivo treatment with AG-490 and IL-12. When tumors reach about 5 multiple myeloma in diameter, AG-490 treatment of tumors is initiated and continued daily for 7-10 days. For MOPC tumors, injections of 0.85 mg/day of AG-490 are given intratumorally, supplemented with 0.5 mg/day of AG-490 i.p. For MPC11 tumors, the intratumoral treatment is halved while the i.p. dose remains the same. Control mice receive 50% DMSO vehicle alone in the same volume as the AG-490 treatment group. Recombinant IL-12 is given s.c. at either 100 ng or 200 ng every other day. Tumor growth is monitored daily by measuring two perpendicular tumor diameters with a caliper, and tumor volume was calculated according to the formula V=0.52*a*b(a+b)/2 (a=smallest superficial diameter; b=largest superficial diameter).

Terminal deoxynucleotidyltransferase-mediated dUTP-Digoxigenin nick-end-labeling (TUNEL) assay. MOPC tumors that receive either AG-490 or 50% DMSO treatment are used for this assay. Three-μm sections from paraffinized tissues are dewaxed and rehydrated according to standard protocols. After incubation with proteinase K (30 min at 21° C.), the TUNEL reaction mixture (Boehringer Mannheim, Indianapolis, Ind.) is added to rinsed slides, which are incubated in a humidified chamber for 60 seconds at 37° C. This is followed by incubating with Converter-AP (50 ml) and substrate solution (50 ml). The reaction is visualized by light microscopy.

Results

AG-490 treatment results in inhibition of MOPC and MPC11 tumor growth and induction of apoptosis in vivo. Both MOPC and MPC11 myeloma cells are rapidly growing, poorly immunogenic tumors in vivo. Mice with 5-mm pre-existing MOPC tumors are treated with either AG-490 or DMSO vehicle subcutaneously for 3 days followed by intra-tumoral injections, and supplemented with daily i.p. injection (see MATERIALS AND METHODS for dosing). All of the AG-490 treated tumors completely regress within 3-8 days (FIG. 27A). However, tumor regrowth is observed in all of the AG-490 treated mice except for one, which develops metastatic foci 2 months after the treatment. Mice with 5 multiple myeloma pre-existing MPC11 tumors are also treated with either AG-490 or DMSO. AG-490 treatment induces rapid rejection of MPC11 tumors in all treated mice (FIG. 28C). However, tumor regrowth or metastasis is observed within 4-7 days after termination of AG-490 treatment (FIG. 28C).

To determine whether AG-490-induced tumor growth inhibition is associated with tumor cell apoptosis, regressing MOPC tumors are examined by TUNEL assay to detect apoptotic tumor cells. As shown in FIG. 27B, while control tumor specimens has no clearly apoptotic cells (panel a), tumor specimens prepared from AG-490-treated mice contain high numbers of apoptotic cells (panel b).

AG-490 does not inhibit in vivo IL-12-induced activation of splenocytes and peritoneal macrophages. While the antitumor effect of AG-490 is transient, cytokine-based immunotherapy can lead to long-term antitumor immune responses. To demonstrate the potential of combining JAK inhibitors with cytokine treatment in order to achieve a prolonged antitumor effect, we analyze the effect of AG-490 on 1L-12-activated immune responses. In vivo treatment of mice with IL-12 has been shown to induce IFN-g production by T lymphocytes and NK cells ex vivo. Whether AG-490 administration would affect rIL-12-induced IFN-g production by splenocytes ex vivo is examined. Although a slight suppression of IL-12-induced IFN-g production by splenocytes from AG-490 treated mice is observed in all experiments, the increase in IFN-g production by splenocytes as a result of rIL-12 administration is the same in both the AG-490- and DMSO-treated animals.

IL-12 is also known to stimulate macrophages. Therefore the effect of in vivo treatment with AG-490 on the ability of peritoneal macrophages to suppress proliferation of tumor cells is examined. Daily i.p., in vivo treatment of AG-490 does not influence IL-2-induced cytostatic activity of peritoneal macrophages against target tumor cells, since the percentages of inhibition of tumor cell proliferation by macrophages derived from AG-490- or DMSO-treated mice are similar.

AG-490 does not induce cell death of IL-12-activated macrophages in vitro. In contrast to in vivo treatment with AG-490, in vitro treatment of macrophages with the inhibitor prevents or suppressed IL-12-mediated nitric oxide production (Table 3). However, whereas AG-490 causes efficient apoptosis of myeloma cells with activated STAT3 (Table 1), no cell death is detected in IL-12-activated peritoneal macrophages treated with 50 mM AG-490 (Table 3).

Recombinant IL-I2 augments the AG-490-mediated antitumor effect. As shown in FIG. 28C, AG-490-mediated tumor regression in the MPC11 model is transient. Simultaneous administration of AG-490 and rIL-12 at the same location (i.p.) does not interfere with IL-12-induced activation of macrophages and splenocytes (Table 2). Whether treatment with low doses of rIL-12 would prolong the AG-490-mediated antitumor effect is then determined. While treatment with rIL-12 alone only slightly inhibits tumor growth (FIG. 28B), dual treatment with AG-490 and rIL-12 results in a significant delay of tumor regrowth and/or development of metastasis compared to treatment with AG-490 alone (FIG. 28D).

Discussion

Syngeneic murine models of myeloma show that combining AG-490 treatment with immunotherapy has therapeutic potential especially in view of the fact that the immunotherapy can help eliminate minimal residual disease and/or induce long-term antitumor immunity. Our current example demonstrates that treatment with AG-490 does not affect IL-12's ability to activate resident peritoneal macrophages and splenocytes in vivo. In addition, the partial response to AG-490 in the murine myeloma models demonstrates that IL-12 treatment significantly enhances the AG-490-mediated antitumor effects.

The present example illustrates a synergism between AG-490 and IL-12 for tumor treatment. Because the majority of hematopoietic malignancies harbor constitutively activated JAK-STAT, administration of AG-490, or other STAT3 inhibitor, in conjunction with immunotherapy represents an attractive novel approach for the treatment of these diseases, and is an embodiment of the present invention.

Example 13

Peptides that Bind to STAT3

In this example, small peptides that bind to full-length STAT3, bind the SH2 domain of STAT3, and/or disrupt STAT3 DNA-binding activity, are disclosed. Also disclosed are novel methods for high-throughput screening of such peptides. Such peptides are useful in the present invention as possible inhibitors of STAT3 signaling, and as lead compounds in the development of such inhibitory pharmaceuticals. Promising small molecule disrupters of STAT3 are tested for their abilities to block STAT3 signaling in intact cells transformed by Src. The activities assayed in NIH3T3 fibroblasts are: (a) inhibition of STAT3-mediated DNA-binding activity, (b) inhibition of STAT3-specific transcriptional activation, (c) reversal of cell transformation and (d) toxicity to normal cells. Methods for rapidly screening such compounds are advantageous in the present invention, because conventional assays, such as EMSA, require large amounts of radioactivity and cumbersome gel electrophoresis. Therefore these conventional assays are slow and expensive compared to the novel assays disclosed herein.

The major mechanisms of action assayed in high throughput in vim assays are: (a) disruption of STAT3 DNA-binding activity and (b) disruption of STAT3 SH2 domain-phosphotyrosine interactions. These assays determine the potential of peptides to disrupt STAT3 function. assess the selectivity of these disrupters for STAT3 relative to other STATs, and define the molecular mechanism of this disruption.

Methods

Phage display peptide libraries are used because of two powerful features. First, phage libraries generate an enormous diversity of peptides that can be subjected to affinity selection by panning. Second, phage display libraries provide a direct physical link between the peptide being displayed on the phage and the DNA sequence encoding it. These combinatorial libraries are based on random short peptide sequences fused to a coat protein of bacteriophage, herein pIII of the filamentous coliphage MI3. Panning of the peptide library using an immobilized target, herein STAT3 fusion proteins bound onto beads, is used to select for peptide sequences that bind to STAT3. Round phage are eluted, subjected to more rounds of affinity selection to enrich for specific binding to STAT3, and then the phage DNAs encoding the displayed peptides are sequenced. Peptide sequences that occur at elevated frequencies are good candidates for ST4T3-specific binding peptides. Two types of phage display peptide libraries are used: a linear peptide library, where the displayed peptide is at the N-terminus of the fusion protein, and libraries based on cyclic peptides. In the latter case, the displayed peptide is a short random sequence flanked by two cysteine residues that form a disulfide link and cyclize the peptide. These cyclic peptides have the advantage of reducing entropic freedom, thereby potentially increasing binding specificity and affinity relative to linear peptides. Another variation on this approach is to combine "affinity maturation" with the phage display peptide library [Scott & Smith, 1990, Science, 249:386-390].

The GST-Stat3 fusion protein is purified on glutathione-Sepharose beads according to standard methods. The first library screened is obtained from a commercial source (New England Biolabs) and consists of random 12 amino acid sequences with a complexity of $1.9 \times 10^9$ independent transformants, each theoretically represented approximately 70 times in $1.4 \times 10^{11}$ phage particles. The displayed 12-mers are at the extreme N-terminus of the mature pIII protein of MI3 phage, and are followed by a spacer (Gly-Gly-Gly-Ser) linking it to the pIII sequence. Extensive sequence analysis of the library, prior to selection, reveals a lack of positional biases except for the expected lack of proline in the first position. This is due to the inability of peptidases to cleave adjacent to proline residues in the peptide leader sequence, which is required for secretion. The titer of the original phage library after one round of amplification is $1.4 \times 10^{13}$ pfu/ml (plaque forming units per ml).

For panning phage with the STAT3 fusion protein, 50 ul of glutathione-Sepharose beads bound to purified GST-Stat3 fusion protein are washed with phosphate buffered saline (PBS). The beads are then incubated with 10 ul of phage suspension ($1.4 \times 10^{11}$ virions) in 200 ul final volume of PBS for 30 min at room temperature with occasional mixing. The beads are gently pelleted in a microcentrifuge, and washed 10 times with 1 ml of PBS to remove unbound phage. Background of non-specifically bound phage is reduced by a variety of methods, including pre-blocking the beads with bovine serum albumin, pre-clearing the phage library with GST-glutathione-Sepharose beads, and washing the beads with increasing salt concentrations. Bound phage virions are eluted from the beads by incubation with a molar excess of glutathione for 30 min at room temperature. A small aliquot of the phage eluate is titered and the rest is amplified on the E. coli ER2537 host strain. Following amplification, the phage are purified by polyethylene glycol (PEG) precipitation and then the titer is determined again. Using $1-2 \times 10^{11}$ phage particles from the amplified eluate as input, the above binding and amplification steps are repeated a total of 3 to 4 times. After the final titering step, 40-100 isolated plaques are amplified for DNA sequencing to identify a consensus binding sequence. Sequence analysis is performed by automated sequencing on a Pharmacia ALF sequencer.

Different STAT3 deletion mutants (FIG. 29) are used as targets together with different phage display peptide libraries. It should be noted that, due to the lack of tyrosine phosphorylation in bacterial cells, all of the STAT3 targets are in the monomeric form (as opposed to dimeric form). This monomeric form has the important advantage that all surfaces which could potentially interact with the peptide libraries are exposed. This includes STAT3 surfaces that mediate protein-protein interactions involved in dimerization as well as the surfaces involved in protein-DNA interactions.

The strategies of affinity maturation are used to improve combinatorial screening. One such strategy involves generation of a secondary phage display library by mutagenesis of the "best" (but still sub-optimal) sequence selected from the initial library, followed by further selection. This mutagenesis-selection strategy is repeated several times to generate a family of related sequences with improved binding affinity. However, this strategy has the disadvantage of starting with only one sub-optimal sequence, which may not ultimately lead to the very best sequence. A preferred strategy, therefore, is to initially select a mixture of sub-optimal sequences with diverse affinities by low stringency selection. This mixture is then mutagenized and subjected to several rounds of selection with increasing stringency. At the final round of mutagenesis, the best sequence in the pool is isolated by the most stringent selection.

A more directed approach is to identify a consensus sequence from screening the initial library as described above, and then fix two or more residues in the consensus while varying the other residues in a secondary library. This significantly increases the probability of finding the very best sequence in terms of STAT3-binding affinity from the library. Another advantage of this more directed approach is that a six amino acid sequence is better suited for designing peptidomimetics.

In the present example, we construct a fusion protein of full-length STAT3 and bacterial glutathione S-transferase (GST) to achieve large-scale expression in E. coli and easy purification using affinity chromatography. In addition to the full-length STAT3 construct, we also fuse the GST protein to various STAT3 mutants, including N-terminal and C-terminal deletion mutants, as well as the isolated SH2 and DNA-binding domains (FIG. 29). Constructs are generated by PCR, and proteins are expressed in bacteria and purified by glutathione-sepharose.

High Throughput Screening.

A novel non-radioactive, 96-well plate based assay is used for measuring STAT3 DNA-binding activity (FIG. 30). In this high throughput assay, a biotinylated hSIE probe is used in place of the $^{32}$P-labeled hSIE probe used for EMSA to detect binding of STAT3 dimers. The hSIE oligonucleotide is a high-affinity mutant of the original sis-inducible element in the C-fos gene promoter that binds STAT3. The biotinylated hSIE probe is immobilized onto a streptavidin-coated 96-well plate, permitting a large number of compounds and concentrations to be tested in a single experiment. The source of activated STAT3 is extracts derived from Sf9 insect cells co-infected with baculoviruses encoding STAT3 and either the Src or Fes tyrosine kinases. Using this baculovirus expression system, high levels of activated STAT3 dimers are produced as a result of phosphorylation by the co-expressed tyrosine kinases. Activated STAT3 is added to the 96-well plate in the presence or absence of the compounds to be screened. After incubation for 30 min with compounds, STAT3 dimers that bind to the biotinylated hSIE probe are detected with an anti-Stat3 primary antibody (Santa Cruz Biotechnology) followed by a horseradish-peroxidase conjugated secondary antibody. Immune complexes are detected by colorimetric conversion of the substrate, 3,3',5,5'-tetramethylbenzidine (TMB) peroxidase, using a conventional ELISA plate reader. Epitope tagged versions of STAT3 expressed from baculoviruses have also been generated that are detected using the cognate primary antibodies. We find these anti-tag antibodies to be more sensitive and/or specific.

To facilitate these high throughput, 96-well plate assays, the screening is automated using an available Beckman 2000 Biotek robotics workstation coupled to an ELISA plate reader. The computer-programmed robotics workstation has multi-volume, multi-component mixing capability that greatly accelerates all of the high throughput assays. Inhibition of STAT3 DNA-binding activity in this assay is readily detected as a loss of signal relative to the controls without added compound. As a positive control and to establish the DNA-binding specificity, activated STAT3 is added in the presence of either excess free hSIE oligonucleotide for competition or a non-binding oligonucleotide, FIRE. Our results show that this 96-well plate assay is specific for detecting STAT3 DNA-binding activity. As a negative control, extracts from IFNa-stimulated cells are used as a source of STAT1, which also binds the hSIE. Initial screens are performed at high concentrations of compounds (e.g., 100 uM), and active compounds are further tested in concentration-response studies.

A second assay specifically designed to detect disruption of phosphotyrosine-SH2 interactions is shown in (FIG. 31). This high throughput assay is based on a synthetic peptide corresponding to the tyrosine phosphorylation site in STAT3 and surrounding sequence, EADPGSAAPY*LKTK (where Y* is phosphotyrosine), which mediates STAT3 homodimer formation. The phosphopeptide is biotinylated and immobilized on streptavidin-coated 96-well plates. Purified, bacterially-expressed GST fusion protein containing the isolated SH2 domain of STAT3 that binds this phosphotyrosine is then added in the presence or absence of compounds. GST-SH2 fusion protein bound to the immobilized phosphopeptide are assayed by addition of a primary anti-GST antibody, followed by a horseradish peroxidase-conjugated secondary antibody. Again, immune complexes are detected by colorimetric conversion of the substrate, 3,3',5,5'-tetramethylbenzidine (TMB) peroxidase, using a conventional ELISA plate reader. Inhibition of phosphotyrosine-SH2 interactions is detected as a decrease in GST-SH2 binding to the immobilized phosphopeptide. To confirm that disruption of dimerization can be detected by this assay, we introduce an excess of soluble phosphorylated or unphosphorylated STAT3 peptide containing the SH2-binding tyrosine. A variation of this assay is also employed with the phosphopeptides and SH2 domains derived from other STAT family members, including STAT1 and STAT5, as a control for specificity of active compounds towards STAT3.

Results

Full-length GST-Stat3, immobilized to glutathione-Sepharose beads, is used to screen a display peptide library containing $1.9 \times 10^9$ random 12-mer peptides positioned at the N-terminus of a minor coat protein (pIII) of the M13 filamentous bacteriophage. Based on their frequencies shown in Table 1, the five most promising peptides from a 12-mer peptide library that bind to full-length STAT3 are listed.

TABLE 1

Peptides that Bind to Full length STAT3 (12-mer Peptide Library).

| Motif | Peptide Sequence | | Frequency (out of 100 clones) |
|---|---|---|---|
| 1 | HY(S/P)PILVYQPSW | (SEQ ID NO: 12) | 25% |
| 2 | QDVHLTQQSRYT | (SEQ ID NO: 13) | 13% |
| 3 | SHPWNAQRELSV | (SEQ ID NO: 14) | 9% |
| 4 | YPAPQPLVTKTS | (SEQ ID NO: 15) | 8% |
| 5 | FSYPLTRAPLNM | (SEQ ID NO: 16) | 8% |

As a second approach, the SH2 domain of STAT3 is isolated as a target for screening 7-mer peptide phage display libraries. These screens identify three additional peptides that bind the SH2 domain with elevated frequencies (Table 2).

TABLE 2

Peptides that Bind the SH2 Domain of STAT3 (7-mer Peptide Library).

| Motif | Peptide Sequence | | Frequency (out of 100 clones) |
|---|---|---|---|
| 1 | HAIYPRN | (SEQ ID NO: 17) | 16% |
| 2 | ASTLPKA | (SEQ ID NO: 18) | 7% |
| 3 | IQSPHFF | (SEQ ID NO: 19) | 6% |

A total of 19 synthetic peptides are tested based on the PY*LKTK sequence (Y*=phosphotyrosine) and their $IC_{50}$ is determined in terms of disruption of STAT3 DNA-binding activity in vitro (Table 3). These results represent important leads because they show disruption of STAT3 DNA-binding activity with peptides containing as few as 3 or 4 amino acids, which is ideal for the synthesis of peptidomimetic combinatorial libraries.

TABLE 3

Disruption of STAT3 DNA-binding Activity.

| Peptide | | $IC_{50}$ (mM) |
|---|---|---|
| PY*LKTK | (SEQ ID NO: 20) | 280 |
| PYLKTK | (SEQ ID NO: 21) | ne |
| AY*LKTK | (SEQ ID NO: 22) | 204 |
| PY*AKTK | (SEQ ID NO: 23) | ne |
| PY*LATK | (SEQ ID NO: 24) | 289 |
| PY*LKAK | (SEQ ID NO: 25) | 300 |
| PY*LKTA | (SEQ ID NO: 26) | 320 |
| PY*LK | (SEQ ID NO: 27) | 410 |
| PY*FK | (SEQ ID NO: 28) | 1000 |
| Y*LK | (SEQ ID NO: 29) | ne |
| AY*LK | (SEQ ID NO: 30) | 365 |
| Ac-Y*LK | (SEQ ID NO: 31) | 421 |
| Ac-PY*LKTK | (SEQ ID NO: 32) | 212 |
| PFLKTK | (SEQ ID NO: 33) | ne |

TABLE 3-continued

Disruption of STAT3 DNA-binding Activity.

| Peptide | | IC$_{50}$ (mM) |
|---|---|---|
| Ac-PY*LK | (SEQ ID NO: 34) | 156 |
| PY*LA | (SEQ ID NO: 35) | 326 |
| Ac-PY*LA | (SEQ ID NO: 36) | 288 |
| PY*L | (SEQ ID NO: 37) | 182 |
| AY*L | (SEQ ID NO: 38) | 147 |

(Y* = phosphotyrosine; ne = no effect; Ac = acetylation

Example 14

Luciferase-Based In Vivo Screening System for Small Molecules that Disrupt STAT3 Signaling Rapid and inexpensive screening to identify compounds that specifically inhibit STAT signaling is an object of the present invention. Such compounds may include peptides or other low molecular weight compounds. In this example it is shown that a cell line suitable for rapid screening of such compounds may be constructed using spectroscopic detection whereby specific inhibition of STAT3 signaling by a test compound results in a change in the relative intensities of light emission from two spectrally distinguishable variants of luciferase, where one variant is linked to a STAT3-responsive promoter and the other variant is linked to a non-STAT3-responsive promoter. A cell line is constructed by conventional techniques of molecular biology and cell biology well known to those of skill in the art, which comprises a first reporter gene such as a gene encoding a luciferase protein having a distinct emission spectrum, and transcription of the mRNA is controlled by a STAT3-responsive promoter. Most preferably, v-Src transformed cell lines possessing constitutive STAT3 DNA binding activity and overexpressing the STAT3-dependent luciferase reporter are used. A second gene, encoding a second luciferase protein with a different emission spectrum to the first luciferase is also incorporated into the cell line such that transcription of the mRNA corresponding to the second luciferase is controlled by a promoter that is not responsive to STAT3 signaling.

Light emission from such a cell line may be recorded before and after addition of a test compound. Specific inhibition of STAT3 signaling is detected by a decrease over a suitable time of light emission from the luciferase gene product linked to the STAT3-responsive promoter, without a corresponding decrease in light emission corresponding to the second luciferase.

The cell line is preferably eucaryotic. The assay may be conveniently carried out in 25 microtitre plates in a conventional plate reader. Robotic control of screening permits rapid and reproducible screening of large numbers of compounds.

Several references to publications within the scientific literature appear in the forgoing description of the present invention, which are hereby incorporated in their respective entireties by reference.

The invention may be embodied in other forms or carried out in other ways without departing from the spirit of the invention or the essential characteristics thereof. The present disclosure is therefore to be considered in all respects illustrative and not restrictive, the scope of the invention being indicated by the appended Claims, and all changes that come within the range and meaning of equivalency are intended to be embraced therein.

What is claimed is:

1. An isolated peptide 3 to 12 amino acids in length that disrupts SH2-phosphotyrosine (pY) interactions between the SH2 domain of one STAT (signal transducer and activator of transcription) 3 polypeptide monomer and a pY on another STAT3 polypeptide monomer, or antagonizes STAT3 DNA binding, wherein said peptide comprises an amino acid sequence selected from the group consisting of SEQ ID NO:17, SEQ ID NO:18, SEQ ID NO:19, SEQ ID NO:20, SEQ ID NO:22, SEQ ID NO:24, SEQ ID NO:25, SEQ ID NO:26, SEQ ID NO:28, SEQ ID NO:30, SEQ ID NO:32, SEQ ID NO:34, SEQ ID NO:35, and SEQ ID NO:36.

2. An isolated peptide 3 to 12 amino acids in length that disrupts SH2-phosphotyrosine (pY) interactions between the SH2 domain of one STAT (signal transducer and activator of transcription) 3 polypeptide monomer and a pY on another STAT3 polypeptide monomer, or antagonizes STAT3 DNA binding, wherein said peptide consists of an amino acid sequence selected from the group consisting of SEQ ID NO:17, SEQ ID NO:18, SEQ ID NO:19, SEQ ID NO:20, SEQ ID NO:22, SEQ ID NO:24, SEQ ID NO:25, SEQ ID NO:26, SEQ ID NO:27, SEQ ID NO:28, SEQ ID NO:30, SEQ ID NO:31, SEQ ID NO:32, SEQ ID NO:34, SEQ ID NO:35, SEQ ID NO:36, SEQ ID NO:37, and SEQ ID NO:38.

3. The isolated peptide of claim 1, wherein said peptide comprises an amino acid sequence selected from the group consisting of SEQ ID NO:17, SEQ ID NO:19, SEQ ID NO:22, SEQ ID NO:24, SEQ ID NO:25, SEQ ID NO:26, SEQ ID NO:30, SEQ ID NO:32, SEQ ID NO:34, and SEQ ID NO:36.

4. The isolated peptide of claim 2, wherein said peptide consists of an amino acid sequence selected from the group consisting of SEQ ID NO:17, SEQ ID NO:19, SEQ ID NO:22, SEQ ID NO:24, SEQ ID NO:25, SEQ ID NO:26, SEQ ID NO:30, SEQ ID NO:31, SEQ ID NO:32, SEQ ID NO:34, and SEQ ID NO:36.

5. A composition comprising said isolated peptide of claim 1 and a pharmaceutically acceptable carrier.

6. A composition comprising said isolated peptide of claim 2 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,345,682 B2 | Page 1 of 1 |
| APPLICATION NO. | : 11/512049 | |
| DATED | : May 24, 2016 | |
| INVENTOR(S) | : Richard Jove et al. | |

It is certified that error appears in the above-identified patent and that said Letters Patent is hereby corrected as shown below:

Specification

Column 1, Lines 16-21, please delete, "The present invention was made with in whole or in part with financial support from the Federal Government under grants CA77859, CA55652, and CA75243 from the National Cancer Institute. The Federal Government may have certain rights in this invention." and insert -- This invention was made with government support CA77859, CA55652 and CA75243 awarded by the National Cancer Institute. The government has certain rights to the invention. --

Signed and Sealed this
Eleventh Day of October, 2016

Michelle K. Lee
*Director of the United States Patent and Trademark Office*

UNITED STATES PATENT AND TRADEMARK OFFICE
CERTIFICATE OF CORRECTION

PATENT NO. : 9,345,682 B2  
APPLICATION NO. : 11/512049  
DATED : May 24, 2016  
INVENTOR(S) : Richard Jove et al.

Page 1 of 1

It is certified that error appears in the above-identified patent and that said Letters Patent is hereby corrected as shown below:

In the Specification

Column 1, Lines 16-18, please delete, "This invention was made with government support CA77859, CA55652 and CA75243 awarded by the National Institutes of Health. The government has certain rights in the invention" and insert -- This invention was made with government support CA077859, CA055652 and CA075243 awarded by the National Cancer Institute. The Government has certain rights in the invention. --, thereof.

Signed and Sealed this  
Nineteenth Day of March, 2019

Andrei Iancu  
*Director of the United States Patent and Trademark Office*

UNITED STATES PATENT AND TRADEMARK OFFICE
CERTIFICATE OF CORRECTION

PATENT NO. : 9,345,682 B2
APPLICATION NO. : 11/512049
DATED : May 24, 2016
INVENTOR(S) : Richard Jove et al.

Page 1 of 1

It is certified that error appears in the above-identified patent and that said Letters Patent is hereby corrected as shown below:

In the Specification

Column 1, Lines 16-18, please delete, "This invention was made with government support CA077859, CA055652 and CA075243 awarded by the National Cancer Institute. The Government has certain rights in the invention." and insert -- This invention was made with government support CA077859, CA055652 and CA075243 awarded by the National Institutes of Health. The Government has certain rights in the invention. --.

This certificate supersedes the Certificate of Correction issued October 11, 2016.

Signed and Sealed this
Sixth Day of October, 2020

Andrei Iancu
*Director of the United States Patent and Trademark Office*

SEQUENCE LISTING

```
<160> NUMBER OF SEQ ID NOS: 38

<210> SEQ ID NO 1
<211> LENGTH: 24
<212> TYPE: DNA
<213> ORGANISM: Homo sapiens

<400> SEQUENCE: 1
agcttcattt cccgtaaatc ccta                                                24

<210> SEQ ID NO 2
<211> LENGTH: 24
<212> TYPE: DNA
<213> ORGANISM: Homo sapiens

<400> SEQUENCE: 2
agcttcattt cccgtaaatc ccta                                                24

<210> SEQ ID NO 3
<211> LENGTH: 22
<212> TYPE: DNA
<213> ORGANISM: Homo sapiens

<400> SEQUENCE: 3
gtcccccggc cggggaggcg ct                                                  22

<210> SEQ ID NO 4
<211> LENGTH: 25
```

```
<212> TYPE: DNA
<213> ORGANISM: Homo sapiens

<400> SEQUENCE: 4
cgacgacttc tcccgccgct accgc                                              25

<210> SEQ ID NO 5
<211> LENGTH: 25
<212> TYPE: DNA
<213> ORGANISM: Homo sapiens

<400> SEQUENCE: 5
ccgcatgctg gggccgtaca gttcc                                              25

<210> SEQ ID NO 6
<211> LENGTH: 20
<212> TYPE: DNA
<213> ORGANISM: Homo sapiens

<400> SEQUENCE: 6
cgggcattca gtgacctgac                                                    20

<210> SEQ ID NO 7
<211> LENGTH: 20
<212> TYPE: DNA
<213> ORGANISM: Homo sapiens

<400> SEQUENCE: 7
tcaggaacca gcggttgaag                                                    20

<210> SEQ ID NO 8
<211> LENGTH: 20
<212> TYPE: DNA
<213> ORGANISM: Homo sapiens

<400> SEQUENCE: 8
ccactgaact tctgattcgc                                                    20

<210> SEQ ID NO 9
<211> LENGTH: 21
<212> TYPE: DNA
<213> ORGANISM: Homo sapiens

<400> SEQUENCE: 9
gcgtgctagc tggatgctct t                                                  21

<210> SEQ ID NO 10
<211> LENGTH: 9
<212> TYPE: DNA
<213> ORGANISM: Homo sapiens

<400> SEQUENCE: 10 ttcggagaa                                                                 9

<210> SEQ ID NO 11
<211> LENGTH: 9
<212> TYPE: DNA
<213> ORGANISM: Homo sapiens

<400> SEQUENCE: 11 tgaggataa                                                                 9

<210> SEQ ID NO 12
```

```
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = Ser or Pro

<400> SEQUENCE: 12

His Tyr Xaa Pro Ile Leu Val Tyr Gln Pro Ser Trp
1               5                   10

<210> SEQ ID NO 13
<211> LENGTH: 12
<212> TYPE: PRT
<213> ORGANISM: Homo sapiens

<400> SEQUENCE: 13

Gln Asp Val His Leu Thr Gln Gln Ser Arg Tyr Thr
1               5                   10

<210> SEQ ID NO 14
<211> LENGTH: 12
<212> TYPE: PRT
<213> ORGANISM: Homo sapiens

<400> SEQUENCE: 14

Ser His Pro Trp Asn Ala Gln Arg Glu Leu Ser Val
1               5                   10

<210> SEQ ID NO 15
<211> LENGTH: 12
<212> TYPE: PRT
<213> ORGANISM: Homo sapiens

<400> SEQUENCE: 15

Tyr Pro Ala Pro Gln Pro Leu Val Thr Lys Thr Ser
1               5                   10

<210> SEQ ID NO 16
<211> LENGTH: 12
<212> TYPE: PRT
<213> ORGANISM: Homo sapiens

<400> SEQUENCE: 16

Phe Ser Tyr Pro Leu Thr Arg Ala Pro Leu Asn Met
1               5                   10

<210> SEQ ID NO 17
<211> LENGTH: 7
<212> TYPE: PRT
<213> ORGANISM: Homo sapiens

<400> SEQUENCE: 17

His Ala Ile Tyr Pro Arg Asn
1               5

<210> SEQ ID NO 18
<211> LENGTH: 7
<212> TYPE: PRT
<213> ORGANISM: Homo sapiens

<400> SEQUENCE: 18

Ala Ser Thr Leu Pro Lys Ala
1               5
```

```
<210> SEQ ID NO 19
<211> LENGTH: 7
<212> TYPE: PRT
<213> ORGANISM: Homo sapiens

<400> SEQUENCE: 19

Ile Gln Ser Pro His Phe Phe
1               5

<210> SEQ ID NO 20
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 20

Pro Xaa Leu Lys Thr Lys
1               5

<210> SEQ ID NO 21
<211> LENGTH: 6
<212> TYPE: PRT
<213> ORGANISM: Homo sapiens

<400> SEQUENCE: 21

Pro Tyr Leu Lys Thr Lys
1               5

<210> SEQ ID NO 22
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 22

Ala Xaa Leu Lys Thr Lys
1               5

<210> SEQ ID NO 23
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 23

Pro Xaa Ala Lys Thr Lys
1               5

<210> SEQ ID NO 24
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 24
```

```
Pro Xaa Leu Ala Thr Lys
1               5

<210> SEQ ID NO 25
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 25

Pro Xaa Leu Lys Ala Lys
1               5

<210> SEQ ID NO 26
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 26

Pro Xaa Leu Lys Thr Ala
1               5

<210> SEQ ID NO 27
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 27

Pro Xaa Leu Lys
1

<210> SEQ ID NO 28
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 28

Pro Xaa Phe Lys
1

<210> SEQ ID NO 29
<211> LENGTH: 3
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Phosphotyrosine

<400> SEQUENCE: 29

Xaa Leu Lys
1
```

```
<210> SEQ ID NO 30
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 30

Ala Xaa Leu Lys
1

<210> SEQ ID NO 31
<211> LENGTH: 3
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Phosphotyrosine
<220> FEATURE:
<221> NAME/KEY: MOD_RES
<222> LOCATION: (1)..(1)
<223> OTHER INFORMATION: ACETYLATION

<400> SEQUENCE: 31

Xaa Leu Lys
1

<210> SEQ ID NO 32
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa = Proline
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: Xaa = Phosphotyrosine

<400> SEQUENCE: 32

Xaa Xaa Leu Lys Thr Lys
1               5

<210> SEQ ID NO 33
<211> LENGTH: 6
<212> TYPE: PRT
<213> ORGANISM: Homo sapiens

<400> SEQUENCE: 33

Pro Phe Leu Lys Thr Lys
1               5

<210> SEQ ID NO 34
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Proline
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 34

Xaa Xaa Leu Lys
 1

<210> SEQ ID NO 35
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 35

Pro Xaa Leu Ala
 1

<210> SEQ ID NO 36
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa = Proline
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 36

Xaa Xaa Leu Ala
 1

<210> SEQ ID NO 37
<211> LENGTH: 3
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 37

Pro Xaa Leu
 1

<210> SEQ ID NO 38
<211> LENGTH: 3
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Phosphotyrosine

<400> SEQUENCE: 38

Ala Xaa Leu
 1
```